US012742010B2

(12) United States Patent
Kehry et al.

(10) Patent No.: US 12,742,010 B2
(45) Date of Patent: Sep. 22, 2026

(54) PD-1 AGONIST AND METHOD OF USING SAME

(71) Applicant: First Tracks Biotherapeutics, Inc., San Diego, CA (US)

(72) Inventors: Marilyn Kehry, San Diego, CA (US); Stephen Parmley, San Diego, CA (US); Robert P. Morse, San Diego, CA (US); Gregory N. Gold, San Diego, CA (US); Janean Fisher, San Diego, CA (US); Martin Edward Dahl, San Diego, CA (US); Margaret Habash Marino, San Diego, CA (US); Rupal Kalapanda, San Diego, CA (US)

(73) Assignee: First Tracks Biotherapeutics, Inc., San Diego, CA (US)

( * ) Notice: Subject to any disclaimer, the term of this patent is extended or adjusted under 35 U.S.C. 154(b) by 1116 days.

(21) Appl. No.: 17/616,567

(22) PCT Filed: Jun. 4, 2020

(86) PCT No.: PCT/US2020/036143

§ 371 (c)(1),
(2) Date: Dec. 3, 2021

(87) PCT Pub. No.: WO2020/247648

PCT Pub. Date: Dec. 10, 2020

(65) Prior Publication Data

US 2022/0235132 A1 Jul. 28, 2022

Related U.S. Application Data

(60) Provisional application No. 62/983,512, filed on Feb. 28, 2020, provisional application No. 62/863,193, filed on Jun. 18, 2019, provisional application No. 62/857,699, filed on Jun. 5, 2019.

(51) Int. Cl.
*C07K 16/28* (2006.01)
*A61P 37/06* (2006.01)

(52) U.S. Cl.
CPC .......... *C07K 16/2818* (2013.01); *A61P 37/06* (2018.01); *C07K 2317/52* (2013.01); *C07K 2317/565* (2013.01)

(58) Field of Classification Search
None
See application file for complete search history.

(56) References Cited

U.S. PATENT DOCUMENTS 6,180,370 B1 * 1/2001 Queen .................... A61P 19/02 435/69.6
7,488,802 B2 2/2009 Collins et al.
8,008,449 B2 * 8/2011 Korman .................... A61P 7/06 530/388.15
8,088,905 B2 1/2012 Collins et al.
8,993,731 B2 3/2015 Tyson
9,683,048 B2 6/2017 Freeman et al.
9,701,749 B2 7/2017 Shibayama et al.
9,815,898 B2 11/2017 Freeman et al.
9,982,052 B2 5/2018 Pantaleo et al.
9,982,053 B2 5/2018 Pantaleo et al.
9,987,500 B2 6/2018 Papadopoulos et al.
10,239,942 B2 3/2019 Amirina et al.
10,294,299 B2 5/2019 Pantaleo et al.
10,323,091 B2 6/2019 Van Dijk et al.
10,390,522 B2 8/2019 Burova et al.
10,450,373 B2 10/2019 Van Dijk et al.
10,493,148 B2 12/2019 Yachi et al.
10,494,436 B2 12/2019 Van Eenennaam et al.
10,544,217 B2 1/2020 Amirina et al.
10,647,770 B2 5/2020 Shibayama et al.
10,737,113 B2 8/2020 Papadopoulos et al.
10,752,687 B2 8/2020 Freeman et al.
10,961,310 B2 3/2021 Viney et al.
10,995,149 B2 5/2021 Chen et al.
11,072,658 B2 7/2021 Fayadat-Dilman et al.
11,130,807 B2 9/2021 Pantaleo et al.
11,136,392 B2 10/2021 Brentjens et al.
11,214,617 B2 1/2022 Pantaleo et al.
11,312,771 B2 4/2022 Edwards et al.
11,591,398 B2 2/2023 Hayes et al.
11,746,161 B2 9/2023 Chen et al.
11,814,429 B2 11/2023 Edwards et al.

(Continued)

FOREIGN PATENT DOCUMENTS

CN 102892785 B 5/2016
CN 108473977 A 8/2018

(Continued)

OTHER PUBLICATIONS

Zhu, Hao-Xian et al. "Targeting pathogenic CD8+ tissue-resident T cells with chimeric antigen receptor therapy in murine autoimmune cholangitis." Nature communications vol. 15,1 2936. Apr. 5, 2024, doi: 10.1038/s41467-024-46654-5 (Year: 2024).*
Bossi, Giovanna, et al. "β-cell targeted Immune Suppressive PD-1 Bispecific Agonists-a Novel Approach to Treat Type 1 Diabetes." Target 15 (2021): 24 (Year: 2021).*
Willemsen, Marcella et al. "Targeting the PD-1/PD-L1 Axis in Human Vitiligo." Frontiers in immunology vol. 11 579022. Nov. 6, 2020, doi:10.3389/fimmu.2020.579022 (Year: 2020).*
Quinn, Joel, et al. "Combined agonism of immune checkpoint receptors, PD-1 and TIGIT, suppresses development of experimental autoimmune uveitis." Investigative Ophthalmology & Visual Science 65.7 (2024): 2988-2988 (Year: 2024).*
Sun, Michel Muzi, et al. "Treatment of IRBP-induced Uveitis via PD-1 Blockade is Mediated Through Regulatory T cell Activation." Investigative Ophthalmology & Visual Science 59.9 (2018): 2538-2538 (Year: 2018).*

(Continued)

*Primary Examiner* — Misook Yu
*Assistant Examiner* — Lia E Taylor
(74) *Attorney, Agent, or Firm* — Leydig, Voit & Mayer, Ltd.

(57) ABSTRACT

Provided is a PD-1-binding agent comprising an immunoglobulin heavy chain polypeptide and immunoglobulin light chain polypeptide, as well as related compositions and methods for making and using same.

24 Claims, 44 Drawing Sheets

Specification includes a Sequence Listing.

(56) References Cited

U.S. PATENT DOCUMENTS

| | | | |
|---|---|---|---|
| 11,981,715 | B2 | 5/2024 | Rios et al. |
| 12,030,945 | B2 | 7/2024 | Chen et al. |
| 12,122,834 | B2 | 10/2024 | Fayadat-Dilman et al. |
| 12,168,687 | B2 | 12/2024 | Mkrtichyan et al. |
| 2012/0269806 | A1 | 10/2012 | Sykes |
| 2014/0220021 | A1 | 8/2014 | Shibayama et al. |
| 2015/0203579 | A1 | 7/2015 | Papadopoulos et al. |
| 2015/0366174 | A1 | 12/2015 | Burova et al. |
| 2017/0044259 | A1 | 2/2017 | Tipton et al. |
| 2017/0044260 | A1 | 2/2017 | Baruah et al. |
| 2018/0127502 | A1 | 5/2018 | Brentjens et al. |
| 2018/0222982 | A1 | 8/2018 | Dranoff et al. |
| 2018/0355061 | A1 | 12/2018 | Chen et al. |
| 2018/0371093 | A1 | 12/2018 | Bilic et al. |
| 2019/0106493 | A1 | 4/2019 | Pantaleo et al. |
| 2019/0144543 | A1 | 5/2019 | Chen et al. |
| 2019/0233518 | A1 | 8/2019 | Fayadat-Dilman et al. |
| 2019/0322749 | A1 | 10/2019 | Edwards et al. |
| 2020/0164071 | A1 | 5/2020 | Sheng et al. |
| 2020/0239570 | A1 | 7/2020 | Edwards et al. |
| 2020/0239573 | A1 | 7/2020 | Hayes et al. |
| 2021/0002369 | A1 | 1/2021 | Ahmed et al. |
| 2021/0032342 | A1 | 2/2021 | Fayadat-Dilman et al. |
| 2021/0206856 | A1 | 7/2021 | Higginson-Scott et al. |
| 2021/0269496 | A1 | 9/2021 | Rios et al. |
| 2021/0347907 | A1 | 11/2021 | Glennie et al. |
| 2021/0363216 | A1 | 11/2021 | Bossi et al. |
| 2021/0380696 | A1 | 12/2021 | Blair et al. |
| 2022/0002409 | A1 | 1/2022 | Viney et al. |
| 2022/0040298 | A1 | 2/2022 | Green et al. |
| 2022/0249659 | A1 | 8/2022 | Kroog et al. |
| 2022/0252599 | A1 | 8/2022 | Lim et al. |
| 2022/0378909 | A1 | 12/2022 | Xu |
| 2023/0022045 | A1 | 1/2023 | Piwnica-Worms et al. |
| 2023/0183347 | A1 | 6/2023 | Honjo et al. |
| 2023/0203157 | A1 | 6/2023 | Torchia et al. |
| 2023/0212291 | A1 | 7/2023 | Jiang et al. |
| 2023/0212293 | A1 | 7/2023 | Keyt et al. |
| 2023/0235004 | A1 | 7/2023 | Viney et al. |
| 2023/0374160 | A1 | 11/2023 | Hermann et al. |
| 2023/0391862 | A1 | 12/2023 | Busfield et al. |
| 2023/0399404 | A1 | 12/2023 | Lim et al. |
| 2024/0052034 | A1 | 2/2024 | Higginson-Scott et al. |
| 2024/0092909 | A1 | 3/2024 | Greving et al. |
| 2024/0132591 | A1 | 4/2024 | Rios et al. |
| 2024/0166745 | A1 | 5/2024 | Lin et al. |
| 2024/0182574 | A1 | 6/2024 | Mkrtichyan et al. |
| 2024/0262905 | A1 | 8/2024 | Mande et al. |
| 2024/0301064 | A1 | 9/2024 | Viney et al. |
| 2024/0316012 | A1 | 9/2024 | Choi et al. |
| 2024/0317859 | A1 | 9/2024 | Honjo et al. |
| 2024/0327493 | A1 | 10/2024 | Carter et al. |
| 2024/0368283 | A1 | 11/2024 | Higginson-Scott et al. |
| 2025/0002582 | A1 | 1/2025 | Higginson-Scott et al. |
| 2025/0019431 | A1 | 1/2025 | Larkin et al. |
| 2025/0034257 | A1 | 1/2025 | Wu et al. |
| 2025/0084168 | A1 | 3/2025 | Wu et al. |
| 2025/0136692 | A1 | 5/2025 | Mkrtichyan et al. |

FOREIGN PATENT DOCUMENTS

| | | | |
|---|---|---|---|
| JP | 2006521783 | A | 9/2006 |
| JP | 2012501669 | A | 1/2012 |
| JP | 2013521769 | A | 6/2013 |
| RU | 2599417 | C2 | 10/2016 |
| WO | WO 2004056875 | A1 | 7/2004 |
| WO | 2010029435 | A1 | 3/2010 |
| WO | WO 2010029434 | A1 | 3/2010 |
| WO | WO 2011110621 | A1 | 9/2011 |
| WO | WO 2018/032793 | A1 | 2/2018 |
| WO | 2018226580 | A2 | 12/2018 |
| WO | 2019206281 | A1 | 10/2019 |
| WO | WO 2019/219709 | A1 | 11/2019 |
| WO | WO 2020/030571 | A1 | 2/2020 |
| WO | WO 2021/011448 | A1 | 1/2021 |
| WO | WO 2021/034890 | A1 | 2/2021 |
| WO | WO 2021/091960 | A1 | 5/2021 |
| WO | WO 2021168192 | A2 | 8/2021 |
| WO | WO 2021216756 | A3 | 10/2021 |
| WO | WO 2021241523 | A1 | 12/2021 |
| WO | WO 2021243028 | A1 | 12/2021 |
| WO | WO 2022040409 | A1 | 2/2022 |
| WO | 2022082019 | A2 | 4/2022 |
| WO | WO 2022082014 | A3 | 4/2022 |
| WO | WO 2022082019 | A3 | 4/2022 |
| WO | 2022124866 | A1 | 6/2022 |
| WO | 2022130206 | A1 | 6/2022 |
| WO | 2023089377 | A2 | 5/2023 |
| WO | 2023224912 | A1 | 11/2023 |
| WO | 2024010861 | A2 | 1/2024 |
| WO | 2024040206 | A2 | 2/2024 |
| WO | 2024091999 | A1 | 5/2024 |
| WO | 2024137731 | A2 | 6/2024 |
| WO | 2024196694 | A2 | 9/2024 |
| WO | 2025042732 | A1 | 2/2025 |
| WO | 2025146662 | A1 | 7/2025 |
| WO | 2025151607 | A1 | 7/2025 |

OTHER PUBLICATIONS

Miao, Xiao et al. "PD-L1 reverses depigmentation in Pmel-1 vitiligo mice by increasing the abundance of Tregs in the skin." Scientific reports vol. 8,1 1605. Jan. 25, 2018, doi: 10.1038/s41598-018-19407-w (Year: 2018).*

Stryer, Biochemistry 4th, WH Freeman, New York. 1995 (Year: 1995).*

Colman, Research in Immunology 145.1 (1994): 33-36 (Year: 1994).*

Aqeel, Faten, Jose Monroy-Trujillo, and Duvuru Geetha. "Immune checkpoint inhibitors as potential triggers for ANCA vasculitis." RMD open 8.2 (2022): e002500 (Year: 2022).*

Angel A. Justiz Vaillant; Sarah Sabir; Arif Jan., "Physiology, Immune Response", [Updated Jul. 27, 2024]. In: StatPearls [Internet]. Treasure Island (FL): StatPearls Publishing; Jan. 2025-) (Year: 2025).*

Waldman, Alex D., Jill M. Fritz, and Michael J. Lenardo. "A guide to cancer immunotherapy: from T cell basic science to clinical practice." Nature Reviews Immunology 20.11 (2020): 651-668 (Year: 2020).*

De Taeye, Steven W et al. "The Ligands for Human IgG and Their Effector Functions." Antibodies (Basel, Switzerland) vol. 8,2 30. Apr. 25, 2019, doi:10.3390/antib8020030 (Year: 2019).*

Janeway, Charles A. "Immunobiology: The Immune System in Health and Disease." 2001 (Year: 2001).*

Kipriyanov, Sergey M., and Fabrice Le Gall. "Generation and production of engineered antibodies." Molecular biotechnology 26.1 (2004): 39-60. (Year: 2004).*

Search Report in Singapore Application No. 11202113394Q dated Aug. 14, 2024.

International Search Report and the Written Opinion in International Application No. PCT/US2020/036143 (Dec. 14, 2020).

Dong, Y., et al., "The research progress on the application of PD-1 in immune regulation," Chemistry of Life, vol. 35, Issue 06, pp. 709-714, Dec. 31, 2015.

Suzanne, L., et al., "Safety, Activity, and Immune Correlates of Anti-PD-1 Antibody in Cancer," N.Engl.J.Med., vol. 366, pp. 2443-2454, Jun. 28, 2012.

Search Report, dated Jan. 5, 2026, in Eurasian Application No. 202591170.

He, J., et al., "Development of PD-1/PD-L1 pathway in tumor immune microenvironment and thereapy for non-small cell lung cancer," Sci. Rpts. Aug. 2015, Article No. 13110.

* cited by examiner

Human PD-1 HEK 293 cells

| 437M5-112 | Description | % IFNγ Inihibition Mean +/- SEM | Donors (N) |
|---|---|---|---|
| APE11844 | CDR-grafted 437M5-112 R71A,T73K,I75S/Parental | 53.39 ± 7.92 | 8 |
| APE11937 | 437M5-112 N31S,T33S,R71A,T73K,I75S,G99R/parental | 47.83 ± 14.72 | 3 |
| APE11944 | 437M5-112 N31S,T33S,R71A,T73K,I75S,G99R,V100cA/parental | 48.48 ± 10.61 | 3 |
| APE11954 | 437M5-112 N31S,R71A,T73K,I75S,G99R/parental | 75.09 ± 7.91 | 3 |
| APE11958 | 437M5-112 N31D,Y32H,R71A,T73K,I75S,G99R/parental | 49.09 ± 9.38 | 4 |
| APE11960 | 437M5-112 N31D,Y32H,M34L,R71A,T73K,I75S,G99R,V100cA/parental | 51.42 ± 13.29 | 3 |
| APE12043 | 437M5-112; N31S,T33S,R71A,T73K,I75S,G99R/Y32F | 83.14 ± 5.72 | 7 |

Figure 10B

| 3.7C6 | Description | % IFNγ Inihibition Mean +/- SEM | Donors (N) |
|---|---|---|---|
| APE11845 | CDR-grafted 3.7C6 V68A/Parental | 76.34 ± 4.34 | 4 |
| APE11980 | 3.7C6 V68A/G100Q,K103R,V104L | 79.52 ± 7.09 | 4 |
| APE12093 | 3.7C6 A52aV,D62Q,V68A/G100Q,K103R,V104L | 87.46 ± 5.16 | 4 |
| APE12095 | 3.7C6 A52aI,D62Q,V68Q/parental | 76.88 ± 7.00 | 6 |
| APE1047.13 | PD-L1-msIgG1-Fc | 83.13 ± 2.79 | 10 |

Figure 11C

Graft vs. Host Disease Model

Intravenous Injection of $3x10^6$ Human PBMC

Endpoints:

- Weight loss
- Death
- GvHD scores: weight loss, activity, fur texture, paleness, posture Median Time to 10% Body Weight Loss

| 3.7C6 IgG1 | IgG1 Isotype | belatacept biosim |
|---|---|---|
| 31 days | 25 days | Not defined |

| 437M5-112 IgG1 | IgG1 Isotype | belatacept biosim |
|---|---|---|
| 29.5 days | 25 days | Not defined |

437M5-112

Single Dose PK Receptor Occupancy

Figure 18A 3.7C6

Figure 18B:
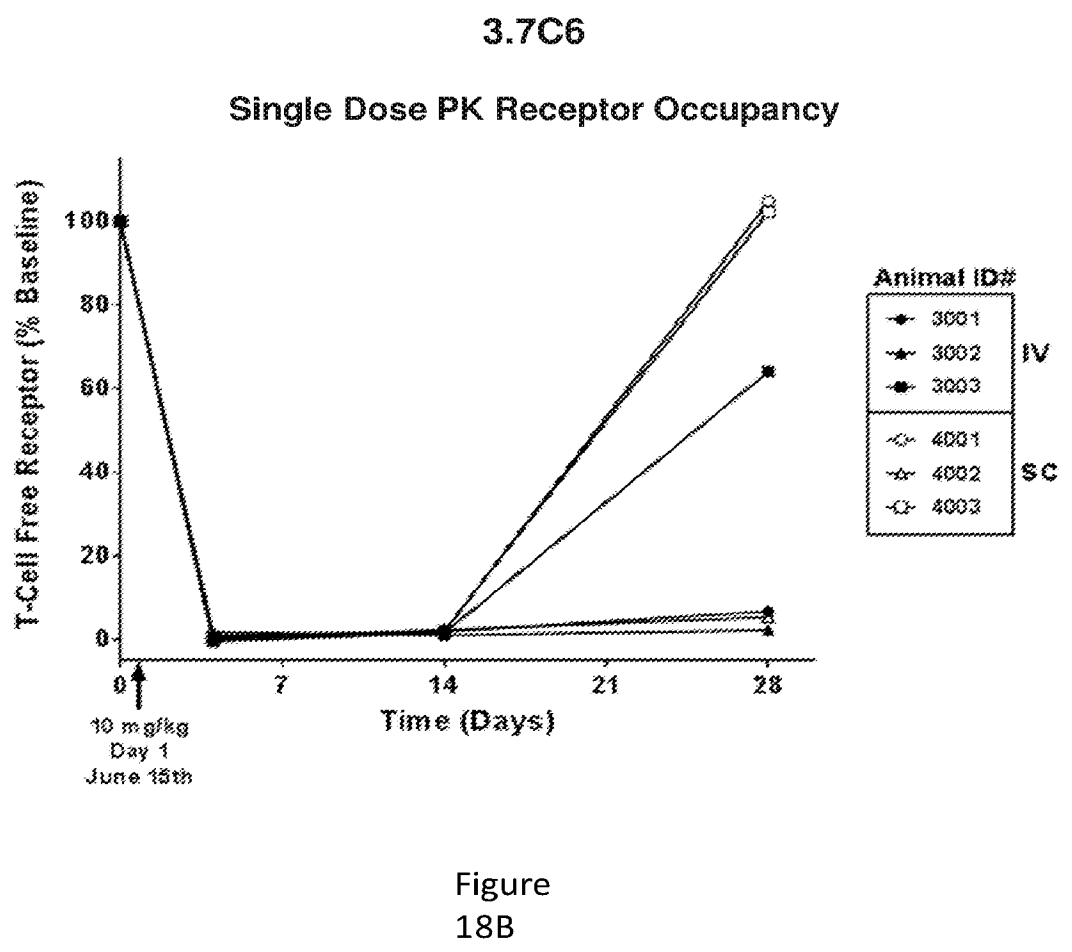

Single Dose PK Receptor Occupancy

T-Cell Free Receptor (% Baseline)

100
80
60
40
20
0

0
7
14
21
28

Time (Days)

10 mg/kg
Day 1
June 15th

Animal ID#

3.7C6 Antibody Induces SHP2 but not SHP1 Recruitment to PD-1 after Activation of Jurkat PD-1 Cells

Mapping of the Epitope on PD-1 Bound by the 3.7C6 Antibody by Hydrogen/Deuterium Exchange and PD-1 Mutational Analyses

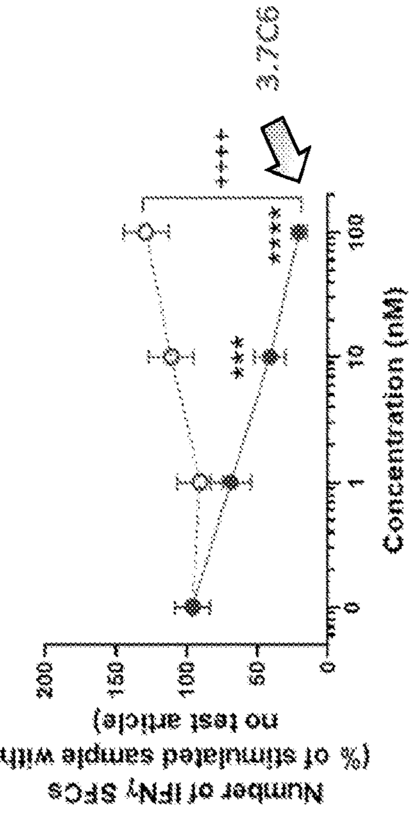
Figure 23C
Melanocyte Antigen Pool 3
Number of IFNγ SFCs (Day 5 + 20 hours)
Normalized Results from 12 Donors
Number of IFNγ SFCs
(% of stimulated sample with
no test article)
150
100
50
0
0
1
10
100
Concentration (nM)
****
++++
PD-L1 IgG1-Fc
Tetramer
Figure 23D

Figure 24A

| Treatment | Median Survival |
|---|---|
| Isotype Control | 20 days |
| 3.7C6 30mg/kg | 39.5 days |
| 3.7C6 10mg/kg | 31 days |
| 3.7C6 3mg/kg | 37 days |
| CTLA-4-Ig | Not defined |

Isotype Control 30mg/kg

% Body Weight Change for Individual Mice

Group 1: Isotype Control

Body Weight Change (%)

Day of Study

SEQUENCE LISTING

```
<160> NUMBER OF SEQ ID NOS: 87

<210> SEQ ID NO 1
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: wherein Xaa is N, S, or D
<220> FEATURE:
<221> NAME/KEY: MISC_FEATURE
<222> LOCATION: (7)..(7)
<223> OTHER INFORMATION: wherein Xaa is Y or H
<220> FEATURE:
<221> NAME/KEY: MISC_FEATURE
<222> LOCATION: (8)..(8)
<223> OTHER INFORMATION: wherein Xaa is T or S
<220> FEATURE:
<221> NAME/KEY: MISC_FEATURE
<222> LOCATION: (9)..(9)
<223> OTHER INFORMATION: wherein Xaa is M or L

<400> SEQUENCE: 1

Gly Tyr Thr Phe Thr Xaa Xaa Xaa Xaa His
1               5                   10


<210> SEQ ID NO 2
<211> LENGTH: 17
<212> TYPE: PRT
<213> ORGANISM: Artificial Sequence
<220> FEATURE:
<223> OTHER INFORMATION: synthetic

<400> SEQUENCE: 2

Tyr Ile Asn Pro Ser Ser Gly Phe Thr Asn Tyr Ile Gln Lys Phe Arg
1               5                   10                  15

Asp


<210> SEQ ID NO 3
<211> LENGTH: 14
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: wherein Xaa is G or R
<220> FEATURE:
<221> NAME/KEY: MISC_FEATURE
<222> LOCATION: (11)..(11)
<223> OTHER INFORMATION: wherein Xaa is V or A

<400> SEQUENCE: 3

Ala Arg Asp Tyr Tyr Gly Xaa Tyr Tyr Tyr Xaa Met Asp Tyr
1               5                   10


<210> SEQ ID NO 4
<211> LENGTH: 12
<212> TYPE: PRT
```

<213> ORGANISM: Artificial Sequence
<220> FEATURE:
<223> OTHER INFORMATION: synthetic
<220> FEATURE:
<221> NAME/KEY: MISC_FEATURE
<222> LOCATION: (10)..(10)
<223> OTHER INFORMATION: wherein Xaa is Y or F

<400> SEQUENCE: 4

Thr Ala Ser Ser Ser Val Ser Ser Ser Xaa Leu His
1 5 10

<210> SEQ ID NO 5
<211> LENGTH: 7
<212> TYPE: PRT
<213> ORGANISM: Artificial Sequence
<220> FEATURE:
<223> OTHER INFORMATION: synthetic

<400> SEQUENCE: 5

Ser Thr Ser Asp Leu Ala Ser
1 5

<210> SEQ ID NO 6
<211> LENGTH: 9
<212> TYPE: PRT
<213> ORGANISM: Artificial Sequence
<220> FEATURE:
<223> OTHER INFORMATION: synthetic

<400> SEQUENCE: 6

His Gln Tyr His Arg Ser Pro Leu Thr
1 5

<210> SEQ ID NO 7
<211> LENGTH: 10
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: wherein Xaa is G or N
<220> FEATURE:
<221> NAME/KEY: MISC_FEATURE
<222> LOCATION: (3)..(3)
<223> OTHER INFORMATION: wherein Xaa is Q or T

<400> SEQUENCE: 7

Xaa Tyr Xaa Phe Thr Asp Tyr Ser Met His
1 5 10

<210> SEQ ID NO 8
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: wherein Xaa is A, I, or V
<220> FEATURE:
<221> NAME/KEY: MISC_FEATURE
<222> LOCATION: (14)..(14)
<223> OTHER INFORMATION: wherein Xaa is D or Q

<400> SEQUENCE: 8

Trp Ile Asn Xaa Glu Thr Tyr Tyr Pro Thr Tyr Ala Asp Xaa Phe Lys 1               5                   10                  15

Gly

<210> SEQ ID NO 9
<211> LENGTH: 14
<212> TYPE: PRT
<213> ORGANISM: Artificial Sequence
<220> FEATURE:
<223> OTHER INFORMATION: Synthetic

<400> SEQUENCE: 9

Ala Arg Asp Tyr Tyr Gly Arg Phe Tyr Tyr Ala Met Asp Tyr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: synthetic

<400> SEQUENCE: 10

Thr Ala Ser Ser Ser Val Ser Ser Ser Tyr Phe His
1               5                   10

<210> SEQ ID NO 11
<211> LENGTH: 7
<212> TYPE: PRT
<213> ORGANISM: Artificial Sequence
<220> FEATURE:
<223> OTHER INFORMATION: synthetic

<400> SEQUENCE: 11

Ser Thr Ser Asn Leu Ala Ser
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic

<400> SEQUENCE: 12

His Gln Tyr His Arg Ser Pro Leu Thr
1               5

<210> SEQ ID NO 13
<211> LENGTH: 10
<212> TYPE: PRT
<213> ORGANISM: Artificial Sequence
<220> FEATURE:
<223> OTHER INFORMATION: synthetic

<400> SEQUENCE: 13

Gly Tyr Thr Phe Thr Asn Tyr Thr Met His
1               5                   10

<210> SEQ ID NO 14
<211> LENGTH: 10
<212> TYPE: PRT
<213> ORGANISM: Artificial Sequence
<220> FEATURE:
<223> OTHER INFORMATION: synthetic

<400> SEQUENCE: 14

Gly Tyr Thr Phe Thr Ser Tyr Thr Met His
1 5 10

<210> SEQ ID NO 15
<211> LENGTH: 10
<212> TYPE: PRT
<213> ORGANISM: Artificial Sequence
<220> FEATURE:
<223> OTHER INFORMATION: Synthetic

<400> SEQUENCE: 15

Gly Tyr Thr Phe Thr Ser Tyr Ser Met His
1 5 10

<210> SEQ ID NO 16
<211> LENGTH: 10
<212> TYPE: PRT
<213> ORGANISM: Artificial Sequence
<220> FEATURE:
<223> OTHER INFORMATION: synthetic

<400> SEQUENCE: 16

Gly Tyr Thr Phe Thr Asn Tyr Ser Met His
1 5 10

<210> SEQ ID NO 17
<211> LENGTH: 10
<212> TYPE: PRT
<213> ORGANISM: Artificial Sequence
<220> FEATURE:
<223> OTHER INFORMATION: Synthetic

<400> SEQUENCE: 17

Gly Tyr Thr Phe Thr Asp His Thr Met His
1 5 10

<210> SEQ ID NO 18
<211> LENGTH: 10
<212> TYPE: PRT
<213> ORGANISM: Artificial Sequence
<220> FEATURE:
<223> OTHER INFORMATION: synthetic

<400> SEQUENCE: 18

Gly Tyr Thr Phe Thr Asp His Thr Leu His
1 5 10

<210> SEQ ID NO 19
<211> LENGTH: 14
<212> TYPE: PRT
<213> ORGANISM: Artificial Sequence
<220> FEATURE:
<223> OTHER INFORMATION: Synthetic

<400> SEQUENCE: 19

Ala Arg Asp Tyr Tyr Gly Gly Tyr Tyr Tyr Val Met Asp Tyr
1 5 10

<210> SEQ ID NO 20
<211> LENGTH: 14
<212> TYPE: PRT
<213> ORGANISM: Artificial Sequence
<220> FEATURE:
<223> OTHER INFORMATION: Synthetic

<400> SEQUENCE: 20

Ala Arg Asp Tyr Tyr Gly Arg Tyr Tyr Tyr Val Met Asp Tyr 1 5 10

<210> SEQ ID NO 21
<211> LENGTH: 14
<212> TYPE: PRT
<213> ORGANISM: Artificial Sequence
<220> FEATURE:
<223> OTHER INFORMATION: Synthetic

<400> SEQUENCE: 21

Ala Arg Asp Tyr Tyr Gly Arg Tyr Tyr Tyr Ala Met Asp Tyr
1 5 10

<210> SEQ ID NO 22
<211> LENGTH: 12
<212> TYPE: PRT
<213> ORGANISM: Artificial Sequence
<220> FEATURE:
<223> OTHER INFORMATION: Synthetic

<400> SEQUENCE: 22

Thr Ala Ser Ser Ser Val Ser Ser Ser Tyr Leu His
1 5 10

<210> SEQ ID NO 23
<211> LENGTH: 12
<212> TYPE: PRT
<213> ORGANISM: Artificial Sequence
<220> FEATURE:
<223> OTHER INFORMATION: Synthetic

<400> SEQUENCE: 23

Thr Ala Ser Ser Ser Val Ser Ser Ser Phe Leu His
1 5 10

<210> SEQ ID NO 24
<211> LENGTH: 122
<212> TYPE: PRT
<213> ORGANISM: Artificial Sequence
<220> FEATURE:
<223> OTHER INFORMATION: Synthetic

<400> SEQUENCE: 24

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Thr Met His Trp Val Arg Gln Ala Pro Gly Gln Gly Leu Glu Trp Met
35 40 45

Gly Tyr Ile Asn Pro Ser Ser Gly Phe Thr Asn Tyr Ile Gln Lys Phe
50 55 60

Arg Asp Arg Val Thr Met Thr Ala Asp Lys Ser Ser Ser Thr Ala Tyr
65 70 75 80

Met Glu Leu Ser Arg Leu Arg Ser Asp Asp Thr Ala Val Tyr Tyr Cys
85 90 95

Ala Arg Asp Tyr Tyr Gly Gly Tyr Tyr Tyr Val Met Asp Tyr Trp Gly
100 105 110

Gln Gly Thr Thr Val Thr Val Ser Ser Ala
115 120

<210> SEQ ID NO 25
<211> LENGTH: 122
<212> TYPE: PRT

<213> ORGANISM: Artificial Sequence
<220> FEATURE:
<223> OTHER INFORMATION: Synthetic

<400> SEQUENCE: 25

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ser Ser Gly Phe Thr Asn Tyr Ile Gln Lys Phe
    50                  55                  60

Arg Asp Arg Val Thr Met Thr Ala Asp Lys Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Tyr Gly Gly Tyr Tyr Tyr Val Met Asp Tyr Trp Gly
            100                 105                 110

Gln Gly Thr Thr Val Thr Val Ser Ser Ala
        115                 120
```

<210> SEQ ID NO 26
<211> LENGTH: 122
<212> TYPE: PRT
<213> ORGANISM: Artificial Sequence
<220> FEATURE:
<223> OTHER INFORMATION: synthetic

<400> SEQUENCE: 26

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ser Met His Trp Val Arg Gln Ala Pro Gly Gln Gly Leu Glu Trp Met
        35                  40                  45

Gly Tyr Ile Asn Pro Ser Ser Gly Phe Thr Asn Tyr Ile Gln Lys Phe
    50                  55                  60

Arg Asp Arg Val Thr Met Thr Ala Asp Lys Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Tyr Gly Gly Tyr Tyr Tyr Val Met Asp Tyr Trp Gly
            100                 105                 110

Gln Gly Thr Thr Val Thr Val Ser Ser Ala
        115                 120
```

<210> SEQ ID NO 27
<211> LENGTH: 122
<212> TYPE: PRT
<213> ORGANISM: Artificial Sequence
<220> FEATURE:
<223> OTHER INFORMATION: synthetic

<400> SEQUENCE: 27

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

```
Thr Met His Trp Val Arg Gln Ala Pro Gly Gln Gly Leu Glu Trp Met
        35                  40                  45

Gly Tyr Ile Asn Pro Ser Ser Gly Phe Thr Asn Tyr Ile Gln Lys Phe
    50                  55                  60

Arg Asp Arg Val Thr Met Thr Ala Asp Lys Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Tyr Gly Arg Tyr Tyr Tyr Val Met Asp Tyr Trp Gly
            100                 105                 110

Gln Gly Thr Thr Val Thr Val Ser Ser Ala
        115                 120


<210> SEQ ID NO 28
<211> LENGTH: 122
<212> TYPE: PRT
<213> ORGANISM: Artificial Sequence
<220> FEATURE:
<223> OTHER INFORMATION: Synthetic

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Tyr Ile Asn Pro Ser Ser Gly Phe Thr Asn Tyr Ile Gln Lys Phe
    50                  55                  60

Arg Asp Arg Val Thr Met Thr Ala Asp Lys Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Tyr Gly Gly Tyr Tyr Tyr Val Met Asp Tyr Trp Gly
            100                 105                 110

Gln Gly Thr Thr Val Thr Val Ser Ser Ala
        115                 120


<210> SEQ ID NO 29
<211> LENGTH: 122
<212> TYPE: PRT
<213> ORGANISM: Artificial Sequence
<220> FEATURE:
<223> OTHER INFORMATION: synthetic

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Tyr Ile Asn Pro Ser Ser Gly Phe Thr Asn Tyr Ile Gln Lys Phe
    50                  55                  60

Arg Asp Arg Val Thr Met Thr Ala Asp Lys Ser Ser Ser Thr Ala Tyr
65                  70                  75                  80

Met Glu Leu Ser Arg Leu Arg Ser Asp Asp Thr Ala Val Tyr Tyr Cys
```

```
                85                  90                  95

Ala Arg Asp Tyr Tyr Gly Arg Tyr Tyr Tyr Val Met Asp Tyr Trp Gly
            100                 105                 110

Gln Gly Thr Thr Val Thr Val Ser Ser Ala
        115                 120


<210> SEQ ID NO 30
<211> LENGTH: 122
<212> TYPE: PRT
<213> ORGANISM: Artificial Sequence
<220> FEATURE:
<223> OTHER INFORMATION: Synthetic

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Tyr Ile Asn Pro Ser Ser Gly Phe Thr Asn Tyr Ile Gln Lys Phe
    50                  55                  60

Arg Asp Arg Val Thr Met Thr Ala Asp Lys Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Tyr Gly Arg Tyr Tyr Tyr Ala Met Asp Tyr Trp Gly
            100                 105                 110

Gln Gly Thr Thr Val Thr Val Ser Ser Ala
        115                 120


<210> SEQ ID NO 31
<211> LENGTH: 122
<212> TYPE: PRT
<213> ORGANISM: Artificial Sequence
<220> FEATURE:
<223> OTHER INFORMATION: Synthetic

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Met
        35                  40                  45

Gly Tyr Ile Asn Pro Ser Ser Gly Phe Thr Asn Tyr Ile Gln Lys Phe
    50                  55                  60

Arg Asp Arg Val Thr Met Thr Ala Asp Lys Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Tyr Gly Arg Tyr Tyr Tyr Val Met Asp Tyr Trp Gly
            100                 105                 110

Gln Gly Thr Thr Val Thr Val Ser Ser Ala
        115                 120


<210> SEQ ID NO 32
<211> LENGTH: 122
```

<212> TYPE: PRT
<213> ORGANISM: Artificial Sequence
<220> FEATURE:
<223> OTHER INFORMATION: Synthetic

<400> SEQUENCE: 32

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Thr Met His Trp Val Arg Gln Ala Pro Gly Gln Gly Leu Glu Trp Met
        35                  40                  45

Gly Tyr Ile Asn Pro Ser Ser Gly Phe Thr Asn Tyr Ile Gln Lys Phe
    50                  55                  60

Arg Asp Arg Val Thr Met Thr Ala Asp Lys Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Tyr Gly Arg Tyr Tyr Tyr Val Met Asp Tyr Trp Gly
            100                 105                 110

Gln Gly Thr Thr Val Thr Val Ser Ser Ala
        115                 120
```

<210> SEQ ID NO 33
<211> LENGTH: 122
<212> TYPE: PRT
<213> ORGANISM: Artificial Sequence
<220> FEATURE:
<223> OTHER INFORMATION: Synthetic

<400> SEQUENCE: 33

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Thr Leu His Trp Val Arg Gln Ala Pro Gly Gln Gly Leu Glu Trp Met
        35                  40                  45

Gly Tyr Ile Asn Pro Ser Ser Gly Phe Thr Asn Tyr Ile Gln Lys Phe
    50                  55                  60

Arg Asp Arg Val Thr Met Thr Ala Asp Lys Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Tyr Gly Arg Tyr Tyr Tyr Ala Met Asp Tyr Trp Gly
            100                 105                 110

Gln Gly Thr Thr Val Thr Val Ser Ser Ala
        115                 120
```

<210> SEQ ID NO 34
<211> LENGTH: 109
<212> TYPE: PRT
<213> ORGANISM: Artificial Sequence
<220> FEATURE:
<223> OTHER INFORMATION: Synthetic

<400> SEQUENCE: 34

```
Asp Ile Gln Met Thr Gln Ser Pro Ser Ser Leu Ser Ala Ser Val Gly
1               5                   10                  15

Asp Arg Val Thr Ile Thr Cys Thr Ala Ser Ser Ser Val Ser Ser Ser
```

```
            20                  25                  30

Tyr Leu His Trp Tyr Gln Gln Lys Pro Gly Lys Ala Pro Lys Leu Leu
        35                  40                  45

Ile Tyr Ser Thr Ser Asp Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys Arg
            100                 105


<210> SEQ ID NO 35
<211> LENGTH: 109
<212> TYPE: PRT
<213> ORGANISM: Artificial Sequence
<220> FEATURE:
<223> OTHER INFORMATION: Synthetic

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Thr Ala Ser Ser Ser Val Ser Ser Ser
            20                  25                  30

Phe Leu His Trp Tyr Gln Gln Lys Pro Gly Lys Ala Pro Lys Leu Leu
        35                  40                  45

Ile Tyr Ser Thr Ser Asp Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys Arg
            100                 105


<210> SEQ ID NO 36
<211> LENGTH: 451
<212> TYPE: PRT
<213> ORGANISM: Artificial Sequence
<220> FEATURE:
<223> OTHER INFORMATION: Synthetic

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ser Met His Trp Val Arg Gln Ala Pro Gly Gln Gly Leu Glu Trp Met
        35                  40                  45

Gly Tyr Ile Asn Pro Ser Ser Gly Phe Thr Asn Tyr Ile Gln Lys Phe
    50                  55                  60

Arg Asp Arg Val Thr Met Thr Ala Asp Lys Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Tyr Tyr Gly Arg Tyr Tyr Tyr Val Met Asp Tyr Trp Gly
            100                 105                 110
```

```
Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 37
<211> LENGTH: 215
<212> TYPE: PRT
<213> ORGANISM: Artificial Sequence
<220> FEATURE:
<223> OTHER INFORMATION: Synthetic

<400> SEQUENCE: 37

Asp Ile Gln Met Thr Gln Ser Pro Ser Ser Leu Ser Ala Ser Val Gly
1               5                   10                  15
```

```
Asp Arg Val Thr Ile Thr Cys Thr Ala Ser Ser Ser Val Ser Ser Ser
            20                  25                  30

Phe Leu His Trp Tyr Gln Gln Lys Pro Gly Lys Ala Pro Lys Leu Leu
        35                  40                  45

Ile Tyr Ser Thr Ser Asp Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 38
<211> LENGTH: 17
<212> TYPE: PRT
<213> ORGANISM: Artificial Sequence
<220> FEATURE:
<223> OTHER INFORMATION: Synthetic

<400> SEQUENCE: 38

Trp Ile Asn Ala Glu Thr Tyr Tyr Pro Thr Tyr Ala Asp Asp Phe Lys
1               5                   10                  15

Gly


<210> SEQ ID NO 39
<211> LENGTH: 17
<212> TYPE: PRT
<213> ORGANISM: Artificial Sequence
<220> FEATURE:
<223> OTHER INFORMATION: Synthetic

<400> SEQUENCE: 39

Trp Ile Asn Ile Glu Thr Tyr Tyr Pro Thr Tyr Ala Asp Asp Phe Lys
1               5                   10                  15

Gly


<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40
```

Trp Ile Asn Ala Glu Thr Tyr Tyr Pro Thr Tyr Ala Asp Gln Phe Lys
1 5 10 15

Gly

<210> SEQ ID NO 41
<211> LENGTH: 17
<212> TYPE: PRT
<213> ORGANISM: Artificial Sequence
<220> FEATURE:
<223> OTHER INFORMATION: Synthetic

<400> SEQUENCE: 41

Trp Ile Asn Val Glu Thr Tyr Tyr Pro Thr Tyr Ala Asp Gln Phe Lys
1 5 10 15

Gly

<210> SEQ ID NO 42
<211> LENGTH: 17
<212> TYPE: PRT
<213> ORGANISM: Artificial Sequence
<220> FEATURE:
<223> OTHER INFORMATION: Synthetic

<400> SEQUENCE: 42

Trp Ile Asn Ile Glu Thr Tyr Tyr Pro Thr Tyr Ala Asp Gln Phe Lys
1 5 10 15

Gly

<210> SEQ ID NO 43
<211> LENGTH: 122
<212> TYPE: PRT
<213> ORGANISM: Artificial Sequence
<220> FEATURE:
<223> OTHER INFORMATION: Synthetic

<400> SEQUENCE: 43

Gln Val Gln Leu Val Gln Ser Gly Ser Glu Leu Lys Lys Pro Gly Ala
1 5 10 15

Ser Val Lys Val Ser Cys Lys Ala Ser Asn Tyr Thr Phe Thr Asp Tyr
20 25 30

Ser Met His Trp Val Arg Gln Ala Pro Gly Gln Gly Leu Glu Trp Met
35 40 45

Gly Trp Ile Asn Ala Glu Thr Tyr Tyr Pro Thr Tyr Ala Asp Asp Phe
50 55 60

Lys Gly Arg Phe Ala Phe Ser Leu Asp Thr Ser Val Ser Thr Ala Tyr
65 70 75 80

Leu Gln Ile Ser Ser Leu Lys Ala Glu Asp Thr Ala Val Tyr Tyr Cys
85 90 95

Ala Arg Asp Tyr Tyr Gly Arg Phe Tyr Tyr Ala Met Asp Tyr Trp Gly
100 105 110

Gln Gly Thr Thr Val Thr Val Ser Ser Ala
115 120

<210> SEQ ID NO 44
<211> LENGTH: 122
<212> TYPE: PRT
<213> ORGANISM: Artificial Sequence
<220> FEATURE:
<223> OTHER INFORMATION: Synthetic

<400> SEQUENCE: 44

```
Gln Val Gln Leu Val Gln Ser Gly Ser Glu Leu Lys Lys Pro Gly Ala
1               5                   10                  15

Ser Val Lys Val Ser Cys Lys Ala Ser Asn Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Tyr Tyr Pro Thr Tyr Ala Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Tyr Gly Arg Phe Tyr Tyr Ala Met Asp Tyr Trp Gly
            100                 105                 110

Gln Gly Thr Thr Val Thr Val Ser Ser Ala
        115                 120


<210> SEQ ID NO 45
<211> LENGTH: 122
<212> TYPE: PRT
<213> ORGANISM: Artificial Sequence
<220> FEATURE:
<223> OTHER INFORMATION: Synthetic

<400> SEQUENCE: 45

Gln Val Gln Leu Val Gln Ser Gly Ser Glu Leu Lys Lys Pro Gly Ala
1               5                   10                  15

Ser Val Lys Val Ser Cys Lys Ala Ser Asn Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ala Glu Thr Tyr Tyr Pro Thr Tyr Ala Asp Gln Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Tyr Gly Arg Phe Tyr Tyr Ala Met Asp Tyr Trp Gly
            100                 105                 110

Gln Gly Thr Thr Val Thr Val Ser Ser Ala
        115                 120


<210> SEQ ID NO 46
<211> LENGTH: 122
<212> TYPE: PRT
<213> ORGANISM: Artificial Sequence
<220> FEATURE:
<223> OTHER INFORMATION: Synthetic

<400> SEQUENCE: 46

Gln Val Gln Leu Val Gln Ser Gly Ser Glu Leu Lys Lys Pro Gly Ala
1               5                   10                  15

Ser Val Lys Val Ser Cys Lys Ala Ser Asn Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Val Glu Thr Tyr Tyr Pro Thr Tyr Ala Asp Gln Phe
    50                  55                  60
```

```
Lys Gly Arg Phe Ala Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Tyr Gly Arg Phe Tyr Tyr Ala Met Asp Tyr Trp Gly
            100                 105                 110

Gln Gly Thr Thr Val Thr Val Ser Ser Ala
        115                 120


<210> SEQ ID NO 47
<211> LENGTH: 122
<212> TYPE: PRT
<213> ORGANISM: Artificial Sequence
<220> FEATURE:
<223> OTHER INFORMATION: Synthetic

<400> SEQUENCE: 47

Gln Val Gln Leu Val Gln Ser Gly Ser Glu Leu Lys Lys Pro Gly Ala
1               5                   10                  15

Ser Val Lys Val Ser Cys Lys Ala Ser Asn Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Tyr Tyr Pro Thr Tyr Ala Asp Gln Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Tyr Gly Arg Phe Tyr Tyr Ala Met Asp Tyr Trp Gly
            100                 105                 110

Gln Gly Thr Thr Val Thr Val Ser Ser Ala
        115                 120


<210> SEQ ID NO 48
<211> LENGTH: 109
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (101)..(101)
<223> OTHER INFORMATION: wherein Xaa is G or Q
<220> FEATURE:
<221> NAME/KEY: MISC_FEATURE
<222> LOCATION: (104)..(104)
<223> OTHER INFORMATION: wherein Xaa is K or R
<220> FEATURE:
<221> NAME/KEY: MISC_FEATURE
<222> LOCATION: (105)..(105)
<223> OTHER INFORMATION: wherein Xaa is V or L

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Ser Thr Ser Asn Leu Ala Ser Gly Ile Pro Ala Arg Phe Ser
```

```
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Ser Pro
                85                  90                  95

Leu Thr Phe Gly Xaa Gly Thr Xaa Xaa Glu Ile Lys Arg
            100                 105


<210> SEQ ID NO 49
<211> LENGTH: 109
<212> TYPE: PRT
<213> ORGANISM: Artificial Sequence
<220> FEATURE:
<223> OTHER INFORMATION: Synthetic

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Ser Thr Ser Asn Leu Ala Ser Gly Ile Pro Ala Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Ser Pro
                85                  90                  95

Leu Thr Phe Gly Gly Gly Thr Lys Val Glu Ile Lys Arg
            100                 105


<210> SEQ ID NO 50
<211> LENGTH: 109
<212> TYPE: PRT
<213> ORGANISM: Artificial Sequence
<220> FEATURE:
<223> OTHER INFORMATION: Synthetic

<400> SEQUENCE: 50

Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Ser Thr Ser Asn Leu Ala Ser Gly Ile Pro Ala Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Ser Pro
                85                  90                  95

Leu Thr Phe Gly Gln Gly Thr Arg Leu Glu Ile Lys Arg
            100                 105


<210> SEQ ID NO 51
<211> LENGTH: 451
<212> TYPE: PRT
<213> ORGANISM: Artificial Sequence
<220> FEATURE:
```

<223> OTHER INFORMATION: Synthetic

<400> SEQUENCE: 51

```
Gln Val Gln Leu Val Gln Ser Gly Ser Glu Leu Lys Lys Pro Gly Ala
1               5                   10                  15

Ser Val Lys Val Ser Cys Lys Ala Ser Asn Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Tyr Tyr Pro Thr Tyr Ala Asp Gln Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Tyr Gly Arg Phe Tyr Tyr Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 52
<211> LENGTH: 215
<212> TYPE: PRT
<213> ORGANISM: Artificial Sequence
<220> FEATURE:
<223> OTHER INFORMATION: Synthetic

<400> SEQUENCE: 52

Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Ser Ser Ser
            20                  25                  30

Tyr Phe His Trp Tyr Gln Gln Lys Pro Gly Gln Ala Pro Arg Leu Leu
        35                  40                  45

Ile Tyr Ser Thr Ser Asn Leu Ala Ser Gly Ile Pro Ala Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Ser Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 53
<211> LENGTH: 1359
<212> TYPE: DNA
<213> ORGANISM: Artificial Sequence
<220> FEATURE:
<223> OTHER INFORMATION: Synthetic

<400> SEQUENCE: 53

caggtgcagc tggtccagtc cggcgctgag gtcaagaagc ccggcgcctc cgtgaaagtg      60

tcctgtaaag cttccggata tacatttaca tcctattcca tgcattgggt gaggcaggcc     120

cccggacaag gactggaatg gatgggatat attaatcctt cctccggatt tacaaactac     180
```

```
attcaaaaat tccgggatag ggtgacaatg accgctgata agtcctcctc caccgcctac    240

atggagctgt cccggctgag gtccgatgat acagctgtgt attattgtgc tagggattat    300

tacggcaggt attattatgt catggattat tggggacaag gcaccaccgt gaccgtgtcc    360

tccgctagca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggccgt cctacagtcc    540

tcaggactct actccctcag cagcgtggtg accgtgccct ccagcagctt gggcacccag    600

acctacatct gcaacgtgaa tcacaagccc agcaacacca aggtggacaa gaaggttgag    660

cccaaatctt gtgacaaaac tcacacatgc ccaccgtgcc cagcacctga actcctgggg    720

ggaccgtcag tcttcctctt ccccccaaaa cccaaggaca ccctcatgat ctcccggacc    780

cctgaggtca catgcgtggt ggtggacgtg agccacgaag accctgaggt caagttcaac    840

tggtacgtgg acggcgtgga ggtgcataat gccaagacaa agccgcggga ggagcagtac    900

aacagcacgt accgtgtggt cagcgtcctc accgtcctgc accaggactg gctgaatggc    960

aaggagtaca agtgcaaggt ctccaacaaa gccctcccag cccccatcga gaaaaccatc   1020

tccaaagcca aagggcagcc ccgagaacca caggtgtaca ccctgccccc atcccgggac   1080

gagctgacca agaaccaggt cagcctgacc tgcctggtca aaggcttcta tcccagcgac   1140

atcgccgtgg agtgggagag caatgggcag ccggagaaca actacaagac cacgcctccc   1200

gtgctggact ccgacggctc cttcttcctc tacagcaagc tcaccgtgga caagagcagg   1260

tggcagcagg ggaacgtctt ctcatgctcc gtgatgcatg aggctctgca caaccactac   1320

acgcagaaga gcctctccct gtctccgggt aaatgatga                          1359
```

<210> SEQ ID NO 54
<211> LENGTH: 651
<212> TYPE: DNA
<213> ORGANISM: Artificial Sequence
<220> FEATURE:
<223> OTHER INFORMATION: Synthetic

<400> SEQUENCE: 54

```
gacatccaga tgacccagtc cccctcctcc ctgtccgcct ccgtgggcga cagggtgacc     60

atcacctgca ccgcctcctc ctccgtgtcc tccagctttc tgcattggta tcaacaaaaa    120

cctggaaaag ctcctaaact gctgatttat tccacatccg atctggcctc cggcgtgccc    180

tccaggttca gcggatccgg atccggaaca gattttacac tgacaatttc ctccctgcaa    240

cctgaagatt ttgccacata ttactgtcat caatatcata ggtcccctct gacatttgga    300

ggaggaacaa aagtggaaat taaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttgatg a             651
```

<210> SEQ ID NO 55
<211> LENGTH: 1359
<212> TYPE: DNA
<213> ORGANISM: Artificial Sequence
<220> FEATURE:

<223> OTHER INFORMATION: Synthetic

<400> SEQUENCE: 55

```
caggtgcagc tggtgcagag cggctccgag ctgaagaagc ccggcgcttc cgtgaaagtg      60
agctgtaagg cttccaatta tacattcaca gattactcca tgcattgggt gaggcaggcc     120
cccggccagg gactggaatg gatgggatgg attaacattg aaacctatta tcccacatac     180
gctgatcaat ttaaaggaag gtttgctttt tccctggata catccgtgtc cacagcttat     240
ctgcaaattt ccagcctgaa agctgaagat acagctgtct attattgtgc tagggattac     300
tatggcaggt tttattatgc tatggattat tggggacaag gaacaacagt gaccgtgtcc     360
tccgctagca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggccgt cctacagtcc     540
tcaggactct actccctcag cagcgtggtg accgtgccct ccagcagctt gggcacccag     600
acctacatct gcaacgtgaa tcacaagccc agcaacacca aggtggacaa gaaggttgag     660
cccaaatctt gtgacaaaac tcacacatgc ccaccgtgcc cagcacctga actcctgggg     720
ggaccgtcag tcttcctctt ccccccaaaa cccaaggaca ccctcatgat ctcccggacc     780
cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctccaacaaa gccctcccag cccccatcga gaaaaccatc    1020
tccaaagcca aagggcagcc ccgagaacca caggtgtaca ccctgccccc atcccgggac    1080
gagctgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaatgatga                           1359
```

<210> SEQ ID NO 56
<211> LENGTH: 651
<212> TYPE: DNA
<213> ORGANISM: Artificial Sequence
<220> FEATURE:
<223> OTHER INFORMATION: Synthetic

<400> SEQUENCE: 56

```
gagatcgtgc tgacccagtc ccccgccacc ctgagcctgt cccccggcga gagggccacc      60
ctgagctgca ccgcctcctc ctccgtgtcc tcctcctatt ttcattggta tcaacaaaaa     120
cctggacaag ctcccaggct gctgatctac tccacctcca acctggcctc cggcatcccc     180
gccaggttct ccggctccgg atccggaaca gattttacac tgacaatttc caggctggaa     240
cctgaagatt ttgctgtgta ttattgtcat cagtatcata ggtcccctct gacatttgga     300
ggaggaacaa aagtggaaat taaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca aagcagacta cgagaaacac aaagtctacg cctgcgaagt cacccatcag     600
```

ggcctgagct cgcccgtcac aaagagcttc aacaggggag agtgttgatg a 651

<210> SEQ ID NO 57
<211> LENGTH: 10
<212> TYPE: PRT
<213> ORGANISM: Artificial Sequence
<220> FEATURE:
<223> OTHER INFORMATION: Synthetic

<400> SEQUENCE: 57

Asn Tyr Thr Phe Thr Asp Tyr Ser Met His
1 5 10

<210> SEQ ID NO 58
<211> LENGTH: 10
<212> TYPE: PRT
<213> ORGANISM: Artificial Sequence
<220> FEATURE:
<223> OTHER INFORMATION: Synthetic

<400> SEQUENCE: 58

Gly Tyr Thr Phe Thr Asp Tyr Ser Met His
1 5 10

<210> SEQ ID NO 59
<211> LENGTH: 10
<212> TYPE: PRT
<213> ORGANISM: Artificial Sequence
<220> FEATURE:
<223> OTHER INFORMATION: Synthetic

<400> SEQUENCE: 59

Asn Tyr Gln Phe Thr Asp Tyr Ser Met His
1 5 10

<210> SEQ ID NO 60
<211> LENGTH: 10
<212> TYPE: PRT
<213> ORGANISM: Artificial Sequence
<220> FEATURE:
<223> OTHER INFORMATION: Synthetic

<400> SEQUENCE: 60

Gly Tyr Gln Phe Thr Asp Tyr Ser Met His
1 5 10

<210> SEQ ID NO 61
<211> LENGTH: 122
<212> TYPE: PRT
<213> ORGANISM: Artificial Sequence
<220> FEATURE:
<223> OTHER INFORMATION: Synthetic

<400> SEQUENCE: 61

Gln Val Gln Leu Val Gln Ser Gly Ser Glu Leu Lys Lys Pro Gly Ala
1 5 10 15

Ser Val Lys Val Ser Cys Lys Ala Ser Gly Tyr Thr Phe Thr Asp Tyr
20 25 30

Ser Met His Trp Val Arg Gln Ala Pro Gly Gln Gly Leu Glu Trp Met
35 40 45

Gly Trp Ile Asn Ile Glu Thr Tyr Tyr Pro Thr Tyr Ala Asp Gln Phe
50 55 60

Lys Gly Arg Phe Ala Phe Ser Leu Asp Thr Ser Val Ser Thr Ala Tyr
65 70 75 80

```
Leu Gln Ile Ser Ser Leu Lys Ala Glu Asp Thr Ala Val Tyr Tyr Cys
                85                  90                  95

Ala Arg Asp Tyr Tyr Gly Arg Phe Tyr Tyr Ala Met Asp Tyr Trp Gly
            100                 105                 110

Gln Gly Thr Thr Val Thr Val Ser Ser Ala
        115                 120


<210> SEQ ID NO 62
<211> LENGTH: 122
<212> TYPE: PRT
<213> ORGANISM: Artificial Sequence
<220> FEATURE:
<223> OTHER INFORMATION: Synthetic

<400> SEQUENCE: 62

Gln Val Gln Leu Val Gln Ser Gly Ser Glu Leu Lys Lys Pro Gly Ala
1               5                   10                  15

Ser Val Lys Val Ser Cys Lys Ala Ser Asn Tyr Gln Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Tyr Tyr Pro Thr Tyr Ala Asp Gln Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Tyr Gly Arg Phe Tyr Tyr Ala Met Asp Tyr Trp Gly
            100                 105                 110

Gln Gly Thr Thr Val Thr Val Ser Ser Ala
        115                 120


<210> SEQ ID NO 63
<211> LENGTH: 122
<212> TYPE: PRT
<213> ORGANISM: Artificial Sequence
<220> FEATURE:
<223> OTHER INFORMATION: Synthetic

<400> SEQUENCE: 63

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Gln Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Tyr Tyr Pro Thr Tyr Ala Asp Gln Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Tyr Gly Arg Phe Tyr Tyr Ala Met Asp Tyr Trp Gly
            100                 105                 110

Gln Gly Thr Thr Val Thr Val Ser Ser Ala
        115                 120
```

<210> SEQ ID NO 64
<211> LENGTH: 5
<212> TYPE: PRT
<213> ORGANISM: Artificial Sequence
<220> FEATURE:
<223> OTHER INFORMATION: Synthetic

<400> SEQUENCE: 64

Asp Tyr Ser Met His
1 5

<210> SEQ ID NO 65
<211> LENGTH: 17
<212> TYPE: PRT
<213> ORGANISM: Artificial Sequence
<220> FEATURE:
<223> OTHER INFORMATION: Synthetic

<400> SEQUENCE: 65

Trp Ile Asn Ile Glu Thr Tyr Tyr Pro Thr Tyr Ala Asp Gln Phe Lys
1 5 10 15

Gly

<210> SEQ ID NO 66
<211> LENGTH: 12
<212> TYPE: PRT
<213> ORGANISM: Artificial Sequence
<220> FEATURE:
<223> OTHER INFORMATION: Synthetic

<400> SEQUENCE: 66

Asp Tyr Tyr Gly Arg Phe Tyr Tyr Ala Met Asp Tyr
1 5 10

<210> SEQ ID NO 67
<211> LENGTH: 12
<212> TYPE: PRT
<213> ORGANISM: Artificial Sequence
<220> FEATURE:
<223> OTHER INFORMATION: Synthetic

<400> SEQUENCE: 67

Thr Ala Ser Ser Ser Val Ser Ser Ser Tyr Phe His
1 5 10

<210> SEQ ID NO 68
<211> LENGTH: 7
<212> TYPE: PRT
<213> ORGANISM: Artificial Sequence
<220> FEATURE:
<223> OTHER INFORMATION: Synthetic

<400> SEQUENCE: 68

Ser Thr Ser Asn Leu Ala Ser
1 5

<210> SEQ ID NO 69
<211> LENGTH: 9
<212> TYPE: PRT
<213> ORGANISM: Artificial Sequence
<220> FEATURE:
<223> OTHER INFORMATION: Synthetic

<400> SEQUENCE: 69

His Gln Tyr His Arg Ser Pro Leu Thr
1 5

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Asn Tyr Thr Phe Thr Asp Tyr Ser
1 5

<210> SEQ ID NO 71
<211> LENGTH: 8
<212> TYPE: PRT
<213> ORGANISM: Artificial Sequence
<220> FEATURE:
<223> OTHER INFORMATION: Synthetic

<400> SEQUENCE: 71

Ile Asn Ile Glu Thr Tyr Tyr Pro
1 5

<210> SEQ ID NO 72
<211> LENGTH: 14
<212> TYPE: PRT
<213> ORGANISM: Artificial Sequence
<220> FEATURE:
<223> OTHER INFORMATION: Synthetic

<400> SEQUENCE: 72

Ala Arg Asp Tyr Tyr Gly Arg Phe Tyr Tyr Ala Met Asp Tyr
1 5 10

<210> SEQ ID NO 73
<211> LENGTH: 7
<212> TYPE: PRT
<213> ORGANISM: Artificial Sequence
<220> FEATURE:
<223> OTHER INFORMATION: Synthetic

<400> SEQUENCE: 73

Ser Ser Val Ser Ser Ser Tyr
1 5

<210> SEQ ID NO 74
<211> LENGTH: 3
<212> TYPE: PRT
<213> ORGANISM: Artificial Sequence
<220> FEATURE:
<223> OTHER INFORMATION: Synthetic

<400> SEQUENCE: 74

Ser Thr Ser
1

<210> SEQ ID NO 75
<211> LENGTH: 9
<212> TYPE: PRT
<213> ORGANISM: Artificial Sequence
<220> FEATURE:
<223> OTHER INFORMATION: Synthetic

<400> SEQUENCE: 75

His Gln Tyr His Arg Ser Pro Leu Thr
1 5

```
<210> SEQ ID NO 76
<211> LENGTH: 5
<212> TYPE: PRT
<213> ORGANISM: Artificial Sequence
<220> FEATURE:
<223> OTHER INFORMATION: Synthetic

<400> SEQUENCE: 76

Ser Tyr Ser Met His
1               5


<210> SEQ ID NO 77
<211> LENGTH: 17
<212> TYPE: PRT
<213> ORGANISM: Artificial Sequence
<220> FEATURE:
<223> OTHER INFORMATION: Synthetic

<400> SEQUENCE: 77

Tyr Ile Asn Pro Ser Ser Gly Phe Thr Asn Tyr Ile Gln Lys Phe Arg
1               5                   10                  15

Asp


<210> SEQ ID NO 78
<211> LENGTH: 12
<212> TYPE: PRT
<213> ORGANISM: Artificial Sequence
<220> FEATURE:
<223> OTHER INFORMATION: Synthetic

<400> SEQUENCE: 78

Asp Tyr Tyr Gly Arg Tyr Tyr Tyr Val Met Asp Tyr
1               5                   10


<210> SEQ ID NO 79
<211> LENGTH: 12
<212> TYPE: PRT
<213> ORGANISM: Artificial Sequence
<220> FEATURE:
<223> OTHER INFORMATION: Synthetic

<400> SEQUENCE: 79

Thr Ala Ser Ser Ser Val Ser Ser Ser Phe Leu His
1               5                   10


<210> SEQ ID NO 80
<211> LENGTH: 7
<212> TYPE: PRT
<213> ORGANISM: Artificial Sequence
<220> FEATURE:
<223> OTHER INFORMATION: Synthetic

<400> SEQUENCE: 80

Ser Thr Ser Asp Leu Ala Ser
1               5


<210> SEQ ID NO 81
<211> LENGTH: 9
<212> TYPE: PRT
<213> ORGANISM: Artificial Sequence
<220> FEATURE:
<223> OTHER INFORMATION: Synthetic

<400> SEQUENCE: 81

His Gln Tyr His Arg Ser Pro Leu Thr
1               5
```

<210> SEQ ID NO 82
<211> LENGTH: 8
<212> TYPE: PRT
<213> ORGANISM: Artificial Sequence
<220> FEATURE:
<223> OTHER INFORMATION: Synthetic

<400> SEQUENCE: 82

Gly Tyr Thr Phe Thr Ser Tyr Ser
1 5

<210> SEQ ID NO 83
<211> LENGTH: 8
<212> TYPE: PRT
<213> ORGANISM: Artificial Sequence
<220> FEATURE:
<223> OTHER INFORMATION: Synthetic

<400> SEQUENCE: 83

Ile Asn Pro Ser Ser Gly Phe Thr
1 5

<210> SEQ ID NO 84
<211> LENGTH: 14
<212> TYPE: PRT
<213> ORGANISM: Artificial Sequence
<220> FEATURE:
<223> OTHER INFORMATION: Synthetic

<400> SEQUENCE: 84

Ala Arg Asp Tyr Tyr Gly Arg Tyr Tyr Tyr Val Met Asp Tyr
1 5 10

<210> SEQ ID NO 85
<211> LENGTH: 7
<212> TYPE: PRT
<213> ORGANISM: Artificial Sequence
<220> FEATURE:
<223> OTHER INFORMATION: Synthetic

<400> SEQUENCE: 85

Ser Ser Val Ser Ser Ser Phe
1 5

<210> SEQ ID NO 86
<211> LENGTH: 3
<212> TYPE: PRT
<213> ORGANISM: Artificial Sequence
<220> FEATURE:
<223> OTHER INFORMATION: Synthetic

<400> SEQUENCE: 86

Ser Thr Ser
1

<210> SEQ ID NO 87
<211> LENGTH: 9
<212> TYPE: PRT
<213> ORGANISM: Artificial Sequence
<220> FEATURE:
<223> OTHER INFORMATION: Synthetic

<400> SEQUENCE: 87

His Gln Tyr His Arg Ser Pro Leu Thr
1 5

PD-1 AGONIST AND METHOD OF USING SAME

CROSS-REFERENCE TO RELATED APPLICATIONS

This patent application claims priority to U.S. provisional patent application 62/857,699 filed Jun. 5, 2019; U.S. provisional patent application 62/863,193 filed Jun. 18, 2019; and U.S. provisional patent application 62/983,512 filed Feb. 28, 2020, the entire disclosures of which are hereby incorporated by reference.

BACKGROUND OF THE INVENTION

Programmed Death 1 (PD-1) (also known as Programmed Cell Death 1) is a type I transmembrane protein of 268 amino acids originally identified by subtractive hybridization of a mouse T cell line undergoing apoptosis (Ishida et al., *Embo J.,* 11: 3887-95 (1992)). PD-1 is a member of the CD28/CTLA-4 family of T-cell regulators, and is reported to be expressed on activated T-cells, B-cells, and myeloid lineage cells (Greenwald et al., *Annu. Rev. Immunol.,* 23: 515-548 (2005); and Sharpe et al., *Nat. Immunol.,* 8: 239-245 (2007)).

Two ligands for PD-1 have been identified, PD ligand 1 (PD-L1) and PD ligand 2 (PD-L2), both of which belong to the B7 protein superfamily (Greenwald et al., supra). PD-L1 is expressed in a variety of cell types, including cells of the lung, heart, thymus, spleen, and kidney (see, e.g., Freeman et al., *J. Exp. Med.,* 192(7): 1027-1034 (2000); and Yamazaki et al., *J. Immunol.,* 169(10): 5538-5545 (2002)). PD-L1 expression is upregulated on macrophages and dendritic cells (DCs) in response to lipopolysaccharide (LPS) and GM-CSF treatment, and on T-cells and B-cells upon signaling via T-cell and B-cell receptors. PD-L1 also is expressed in a variety of murine and human tumor cell lines (see, e.g., Iwai et al., *Proc. Natl. Acad. Sci. USA,* 99(19): 12293-12297 (2002); and Blank et al., *Cancer Res.,* 64(3): 1140-1145 (2004)). In contrast, PD-L2 exhibits a more restricted expression pattern and is expressed primarily by antigen presenting cells (e.g., dendritic cells and macrophages), and some tumor cell lines (see, e.g., Latchman et al., *Nat. Immunol.,* 2(3): 261-238 (2001)).

PD-1 negatively regulates T-cell activation, and this inhibitory function is linked to an immunoreceptor tyrosine-based switch motif (ITSM) in the cytoplasmic domain (see, e.g., Greenwald et al., supra; and Parry et al., *Mol. Cell. Biol.,* 25: 9543-9553 (2005)). PD-L1-induced clustering of PD-1 has been found to induce recruitment of the SHP2 phosphatase which preferentially dephosphorylates CD28, suppressing T cell function (Hui et al., *Science,* 355: 1428-1433 (2017)). PD-1 deficiency can lead to autoimmunity. For example, C57BL/6 PD-1 knockout mice have been shown to develop a lupus-like syndrome (see, e.g., Nishimura et al., *Immunity,* 11: 141-1151 (1999)). In humans, a single nucleotide polymorphism in the PD-1 gene is associated with higher incidences of systemic lupus erythematosus, type 1 diabetes, rheumatoid arthritis, and progression of multiple sclerosis (see, e.g., Nielsen et al., *Tissue Antigens,* 62(6): 492-497 (2003); Bertsias et al., *Arthritis Rheum.,* 60(1): 207-218 (2009); Ni et al., *Hum. Genet.,* 121(2): 223-232 (2007); Tahoori et al., *Clin. Exp. Rheumatol.,* 29(5): 763-767 (2011); and Kroner et al., *Ann. Neurol.,* 58(1): 50-57 (2005)).

Despite recent advances in inhibiting PD-1 activity to treat various types of cancer and for immunopotentiation (e.g., to treat infectious diseases) there is a need for a PD-1-binding agent (e.g., an antibody) that binds PD-1 with high affinity which promotes negative signaling and functions as a PD-1 agonist.

BRIEF SUMMARY OF THE INVENTION

The invention provides an agonistic PD-1 binding agent. In one embodiment, the PD-1 binding agent comprises an immunoglobulin heavy chain variable region and an immunoglobulin light chain variable region, wherein the immunoglobulin heavy chain variable region comprises: a CDR1 comprising SEQ ID NO: 1; a CDR2 comprising SEQ ID NO: 2; and a CDR3 comprising SEQ ID NO: 3; and the immunoglobulin light chain variable region comprises a CDR1 comprising SEQ ID NO: 4; a CDR2 comprising SEQ ID NO: 5; and a CDR3 comprising SEQ ID NO: 6.

Also provided is an anti-PD-1 binding agent comprising an immunoglobulin heavy chain variable region with at least 80%, 85% or 90% sequence identity to any one of SEQ ID NOs: 24-33, or a heavy chain variable region comprising at least the CDR regions of SEQ ID NOs: 24-33, and/or an immunoglobulin light chain variable region with at least 80%, 85% or 90% sequence identity to SEQ ID NO: 34 or 35, or a light chain variable region comprising at least the CDR regions of SEQ ID NO: 34 or 35.

In another aspect, the PD-1 binding agent comprises an immunoglobulin heavy chain variable region and an immunoglobulin light chain variable region, wherein the immunoglobulin heavy chain variable region comprises: a CDR1 comprising SEQ ID NO: 7; a CDR2 comprising SEQ ID NO: 8; and a CDR3 comprising SEQ ID NO: 9; and the immunoglobulin light chain variable region comprises a CDR1 comprising SEQ ID NO: 10; a CDR2 comprising SEQ ID NO: 11; and a CDR3 comprising SEQ ID NO: 12.

Also provided is an anti-PD-1 binding agent comprising an immunoglobulin heavy chain variable region with at least 80%, 85% or 90% sequence identity to any one of SEQ ID NOs: 43-47 or 61-63, or a heavy chain variable region comprising at least the CDR regions thereof, and/or an immunoglobulin light chain variable region with at least 80%, 85% or 90% sequence identity to SEQ ID NOs: 48-50, or a light chain variable region comprising at least the CDR regions thereof.

In addition, the invention provides isolated or purified nucleic acid sequences encoding the foregoing immunoglobulin polypeptides, vectors comprising such nucleic acid sequences, isolated PD-1-binding agents comprising the foregoing immunoglobulin polypeptides, nucleic acid sequences encoding such PD-1-binding agents, vectors comprising such nucleic acid sequences, isolated cells comprising such vectors, compositions comprising such PD-1-binding agents or such vectors with a pharmaceutically acceptable carrier, and methods inhibiting an immune response and treating inflammatory or autoimmune disorders in mammals by administering effective amounts of such compositions to mammals.

BRIEF DESCRIPTION OF THE SEVERAL VIEWS OF THE DRAWING(S)

FIG. 4 is a graph depicting the results of a competition assay, which illustrates the ability of anti-PD-1 antibodies to compete with PD-L1-Fc for binding to CHO-K1 cells stably transfected with human PD-1.

FIG. 5 is a graph depicting the results of a competition assay, which illustrates the ability of anti-PD-1 antibodies to compete with PD-L1-Fc for binding to CHO-K1 cells stably transfected with human PD-1.

FIG. 6 is a graph depicting the results of a competition assay, which illustrates the ability of anti-PD-1 antibodies to compete with PD-L2-Fc for binding to CHO-K1 cells stably transfected with human PD-1.

FIG. 7 is a graph depicting the results of a competition assay, which illustrates the ability of anti-PD-1 antibodies to compete with PD-L2-Fc for binding to CHO-K1 cells stably transfected with human PD-1.

FIG. 10B is a chart providing a description of anti-PD-1 antibodies, % inhibition of IFNγ, and number of donors included in FIG. 10A.

FIG. 11C is a chart providing the candidate antibodies, description of the antibodies, % inhibition of IFNγ, and number of donors included in FIGS. 11A and 11B.

FIG. 18A is a graph depicting the $CD3^+$ T-cell PD-1 receptor occupancy in cynomolgus monkeys after a 10 mg/kg intravenous or subcutaneous single dose of an anti-PD-1 antibody.

FIG. 18B is a graph depicting the $CD3^+$ T-cell PD-1 receptor occupancy in cynomolgus monkeys after a 10 mg/kg intravenous or subcutaneous single dose of an anti-PD-1 antibody.

Figures 20A, 20B:
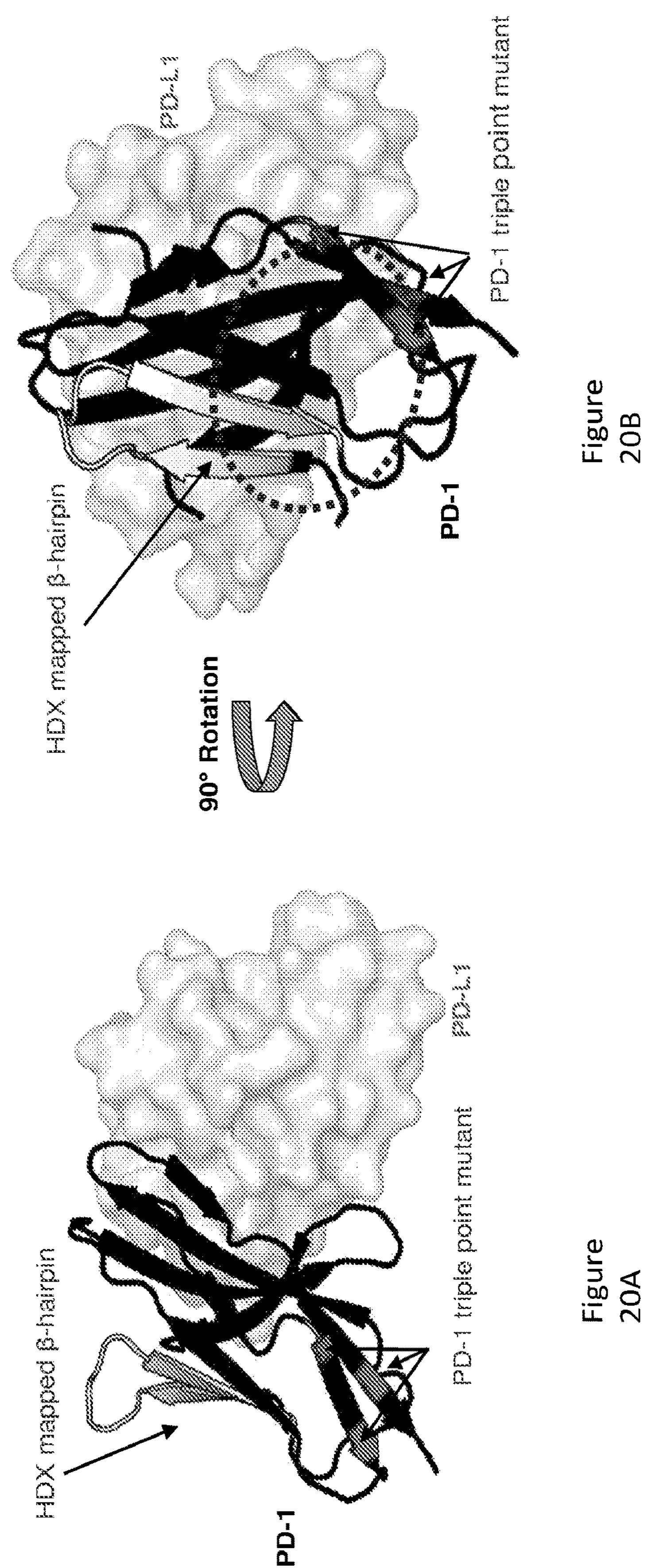

FIG. 20A is a ribbon-model illustration of the crystal structure of human PD-1 extracellular domain (black) docked with a space-filling model of the crystal structure of human PD-L1 extracellular binding domain (gray). The molecule is oriented with the membrane-proximal region of PD-1 at the bottom left, FIG. 20B is a ribbon-model illustration of the crystal structure of human PD-1 extracellular domain (black)

docked with a space-filling model of the crystal structure of human PD-L1 extracellular binding domain (gray). The molecule is rotated by 900 as compared to the view of the molecule shown in FIG. 20A, showing the membrane-proximal region of PD-1 at the bottom center.

Figure 21B:
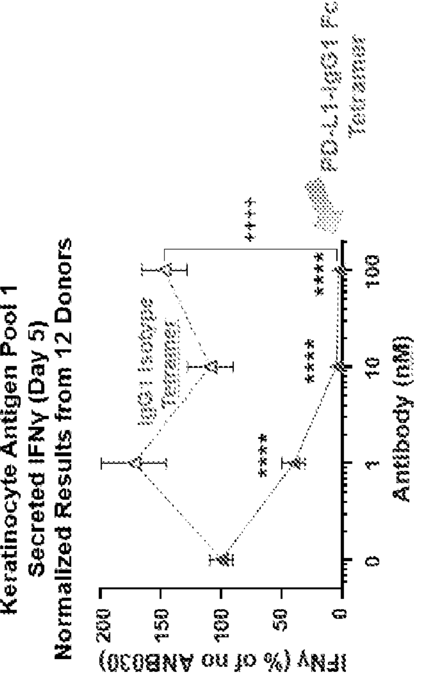
Figure 21A:
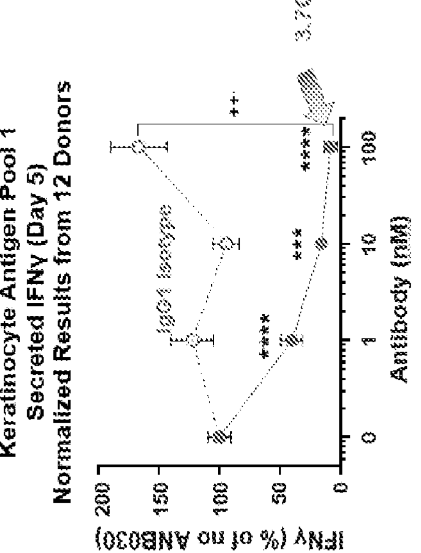

FIG. 21A is a graph depicting the effect of IgG1 3.7C6 anti-PD-1 antibody on secreted IFNγ in PBMCs from alopecia areata donors stimulated with keratinocyte antigens as compared to IgG1 isotype.

FIG. 21B is a graph depicting the effect of PD-L1-IgG1 Fc tetramer on secreted IFNγ in PBMCs from alopecia areata donors stimulated with keratinocyte antigens as compared to IgG1 isotype tetramer.

Figure 21D:
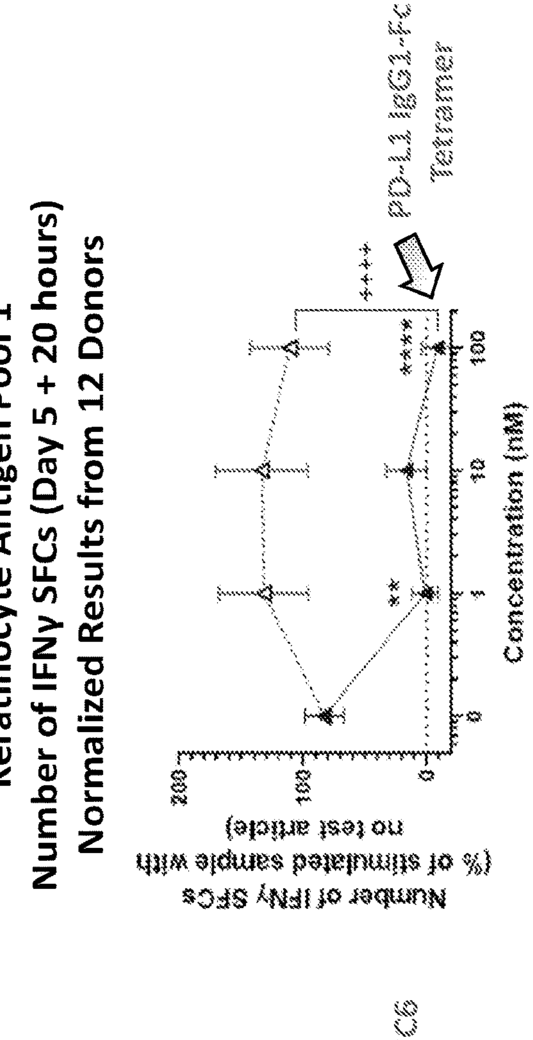
Figure 21C:
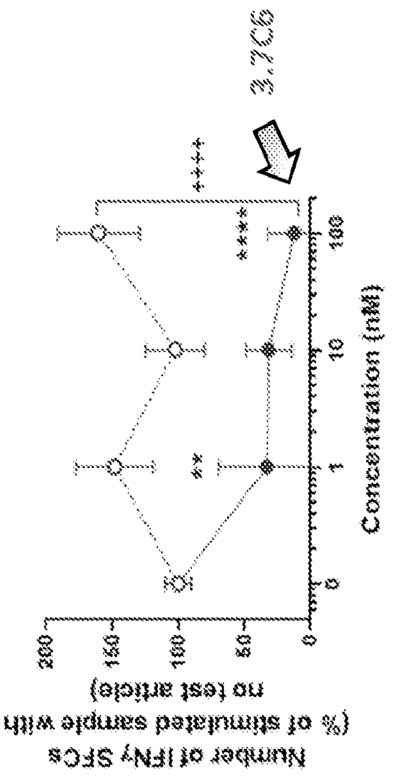

FIG. 21C is a graph depicting the effect of IgG1 3.7C6 anti-PD-1 antibody on the number of IFNγ spotforming cells (SFCs) in PBMCs isolated from alopecia areata donors stimulated with keratinocyte antigens.

FIG. 21D is a graph depicting the effect of PD-L1 IgG1-Fc tetramer on the number of IFNγ spotforming cells (SFCs) in PBMCs isolated from alopecia areata donors stimulated with keratinocyte antigens.

Figures 22A, 22B:
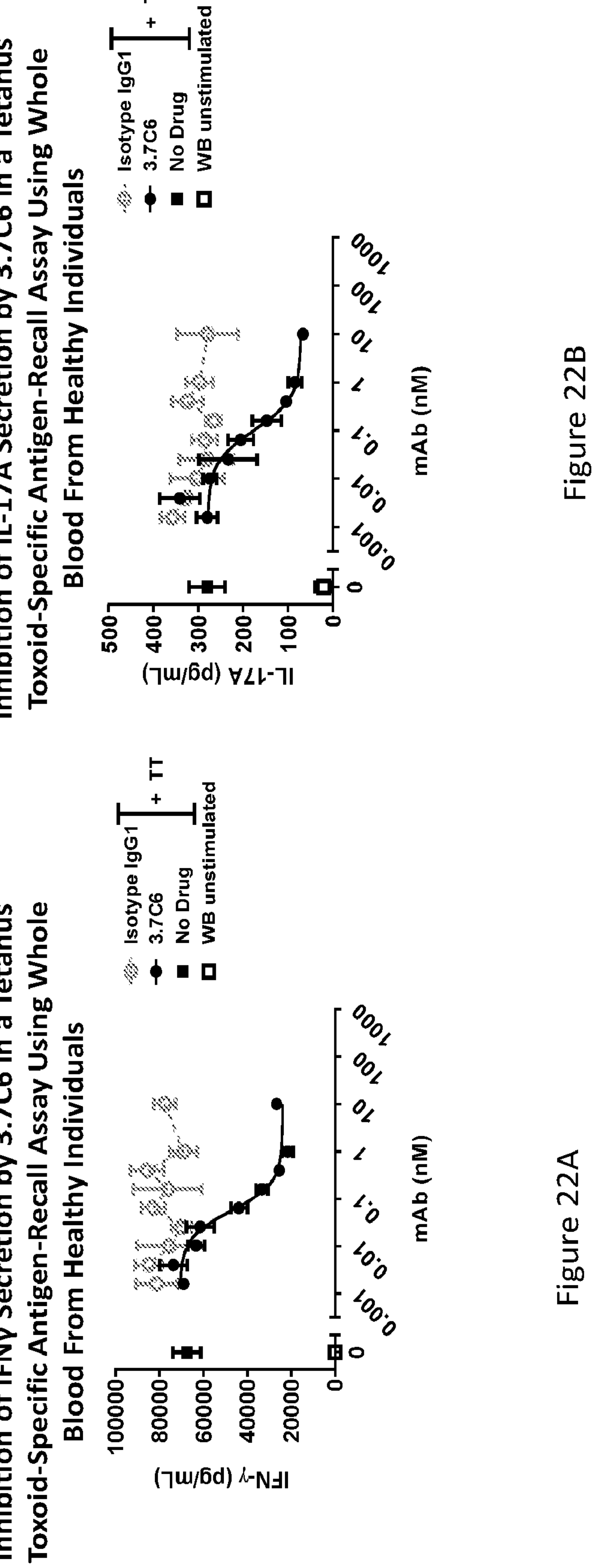

FIG. 22A is a graph depicting the effect of IgG1 3.7C6 anti-PD-1 antibody on secreted INFγ in a Tetanus Toxoid-specific antigen-recall assay as compared to IgG1 isotype.

FIG. 22B is a graph depicting the effect of IgG1 3.7C6 anti-PD-1 antibody on secreted IL-17A in a Tetanus Toxoid-specific antigen-recall assay as compared to IgG1 isotype.

Figure 23B:
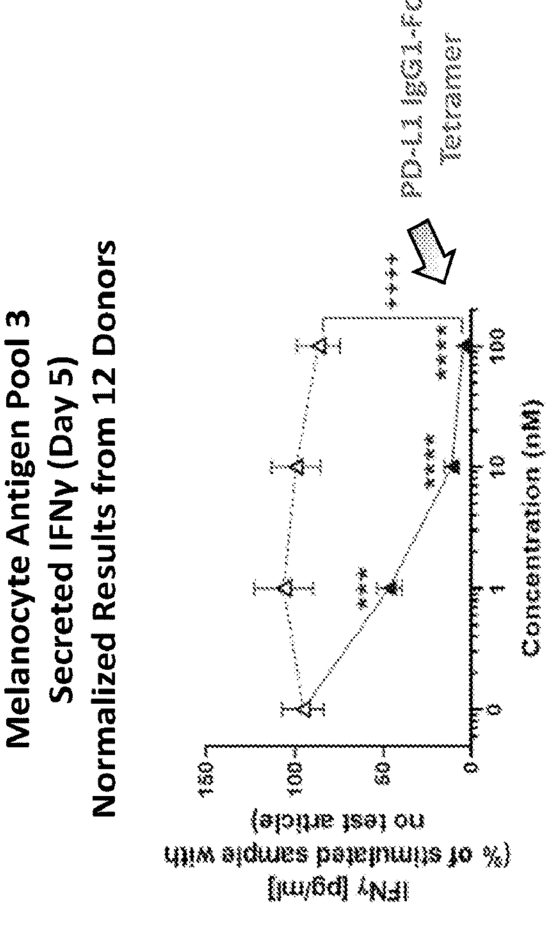
Figure 23A:
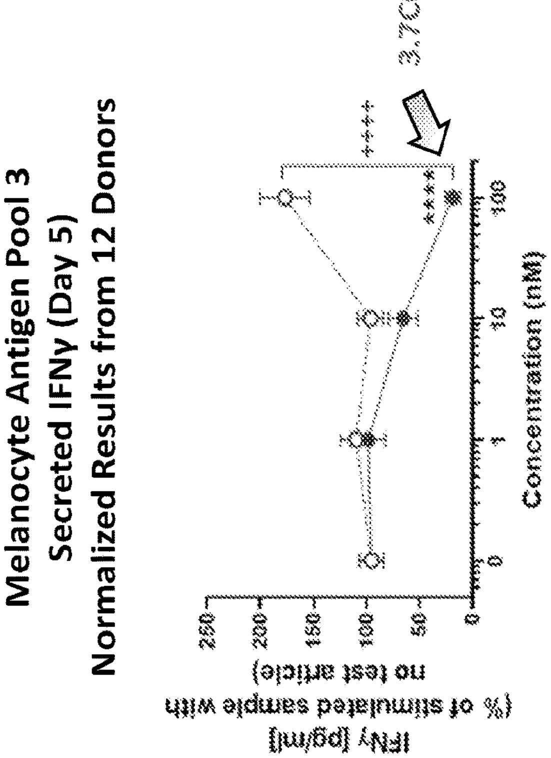

FIG. 23A is a graph depicting the effect of IgG1 3.7C6 anti-PD-1 antibody on secreted IFNγ in PBMCs from alopecia areata donors stimulated with melanocyte antigens as compared to igG1 isotype.

FIG. 23B is a graph depicting the effect of PD-L1-IgG1-Fc tetramer on secreted IFNγ in PBMCs from alopecia areata donors stimulated with melanocyte antigens as compared to IgG1 isotype tetramer.

FIG. 23C is a graph depicting the effect of IgG1 3.7C6 anti-PD-1 antibody on the number of IFNγ SFCs in PBMCs isolated from alopecia areata donors stimulated with melanocyte antigens.

FIG. 23D is a graph depicting the effect of PD-L1 IgG1-Fc tetramer on the number of IFNγ SFCs in PBMCs isolated from alopecia areata donors stimulated with melanocyte antigens.

Figure 24A:
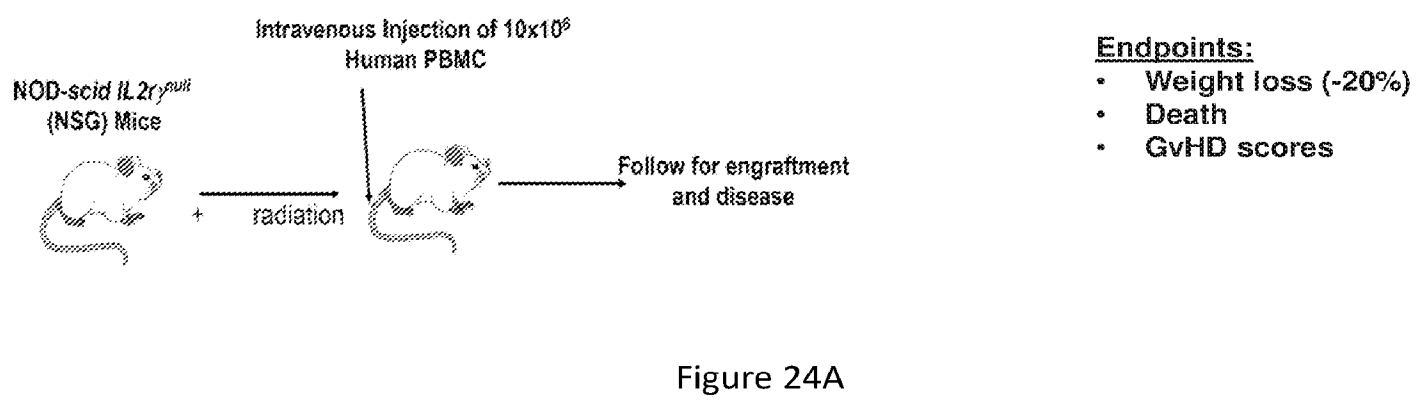

FIG. 24A is a schematic of the xenogeneic NSG/Hu-PBMC mouse model for the Graft vs. Host Disease study described in Example 15, in accordance with the embodiments of the invention.

Figure 24B:
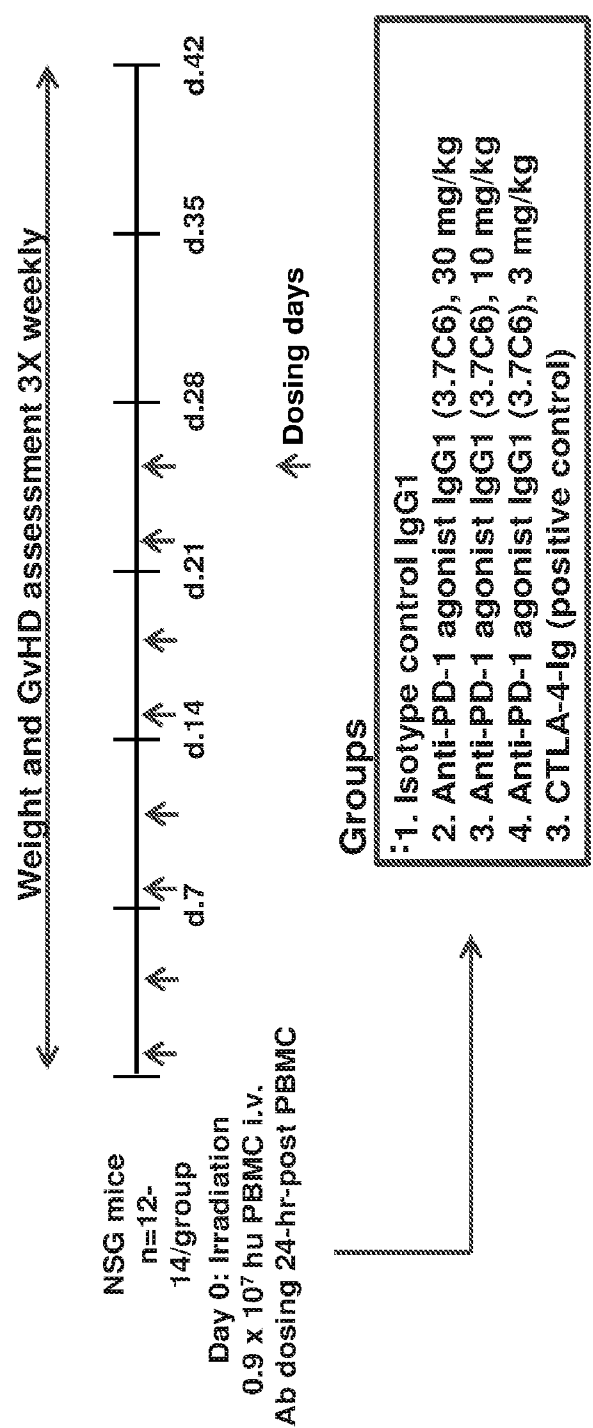

FIG. 24B is a schematic showing the timeline, dosing schedule, and model groups of the NSG/Hu-PBMC Graft vs. Host Disease study described in Example 15, in accordance with the embodiments of the invention.

Figure 24C:
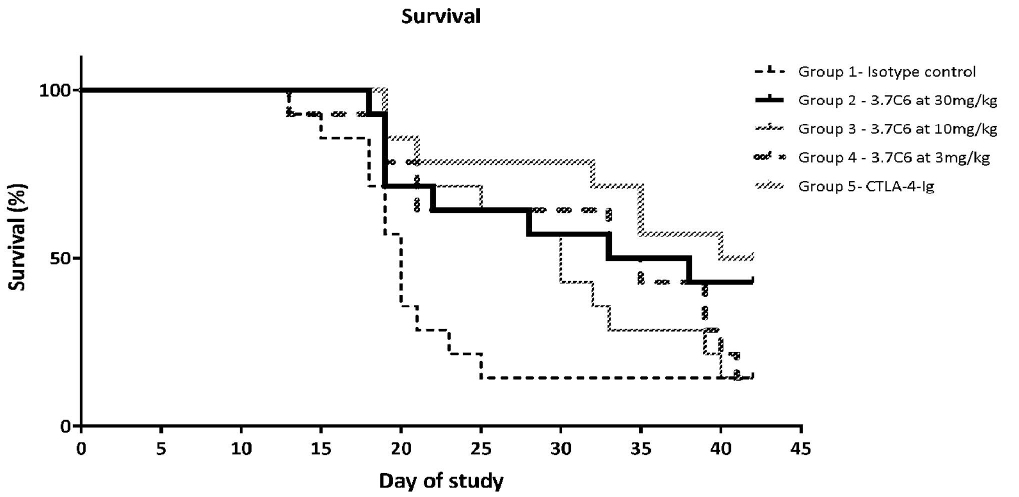
Figure 24C:
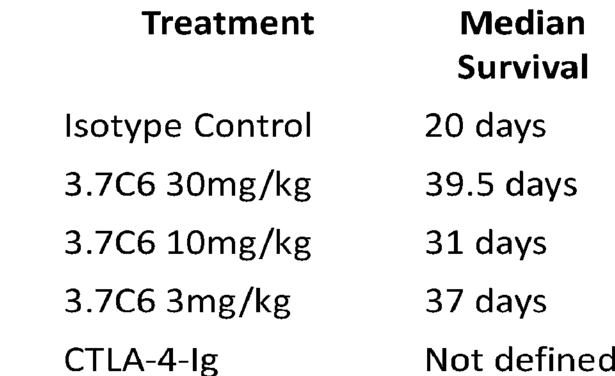
Figure 24C:

FIG. 24C is a graph depicting the results of the time to death of the NSG/Hu-PBMC Graft vs. Host Disease study in Example 15 for anti-PD-1 agonist IgG1 antibody 3.7C6.

Figures 24D, 24E:
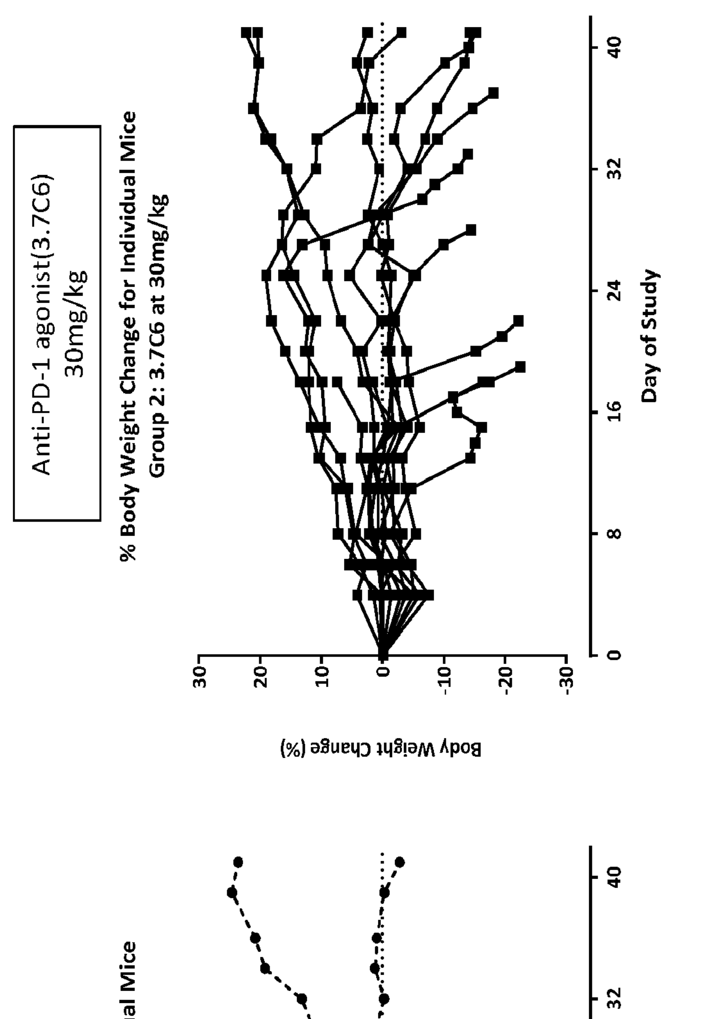

FIG. 24D is a graph depicting the results of the percent body weight change from start of study of individual animals for isotype control during the time of the study.

FIG. 24E is a graph depicting the results of the percent body weight change from start of study of individual animals for anti-PD-1 agonist IgG1 antibody 3.7C6 at 30 mg/kg dosage during the time of the study.

Figure 24G:
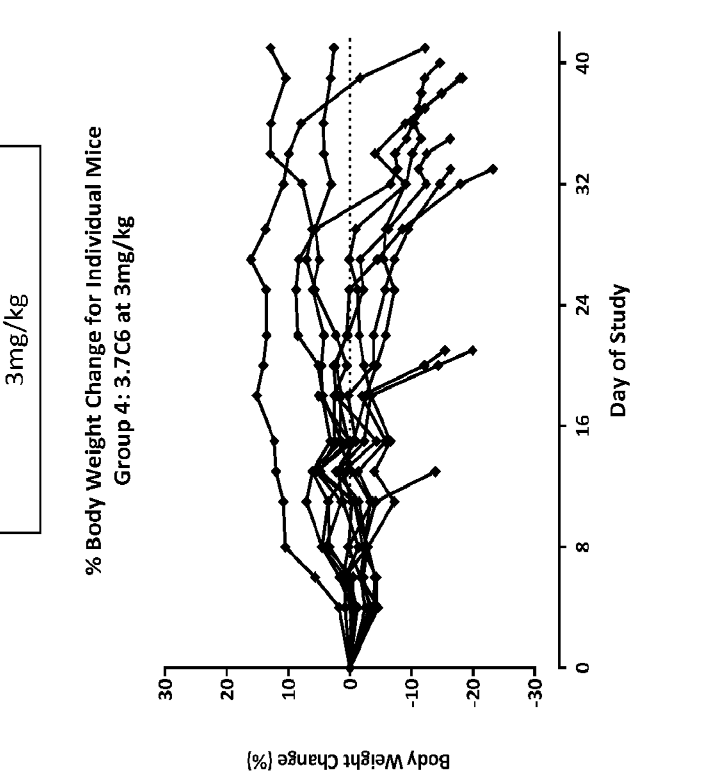
Figure 24F:
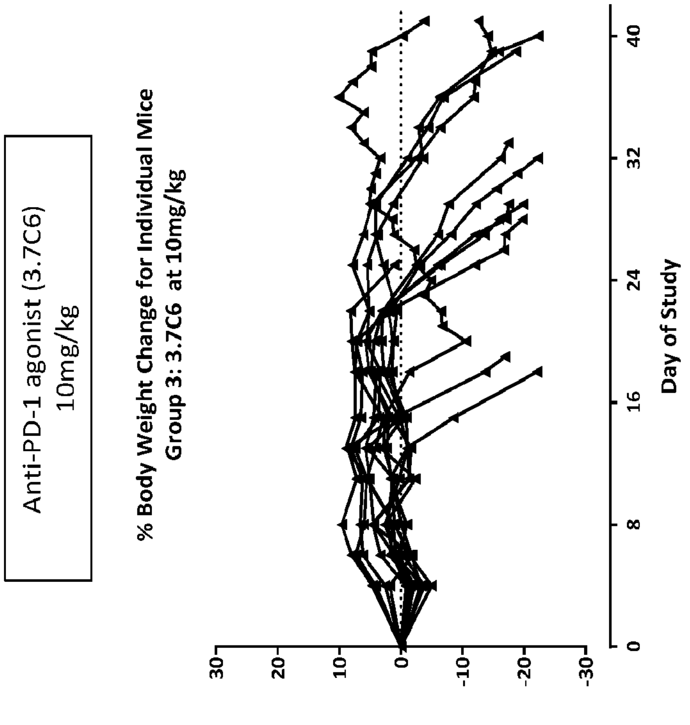

FIG. 24F is a graph depicting the results of the percent body weight change from start of study of individual animals for anti-PD-1 agonist IgG1 antibody 3.7C6 at 10 mg/kg dosage during the time of the study.

FIG. 24G is a graph depicting the results of the percent body weight change from start of study of individual animals for anti-PD-1 agonist IgG1 antibody 3.7C6 at 3 mg/kg dosage during the time of the study.

Figure 24H:
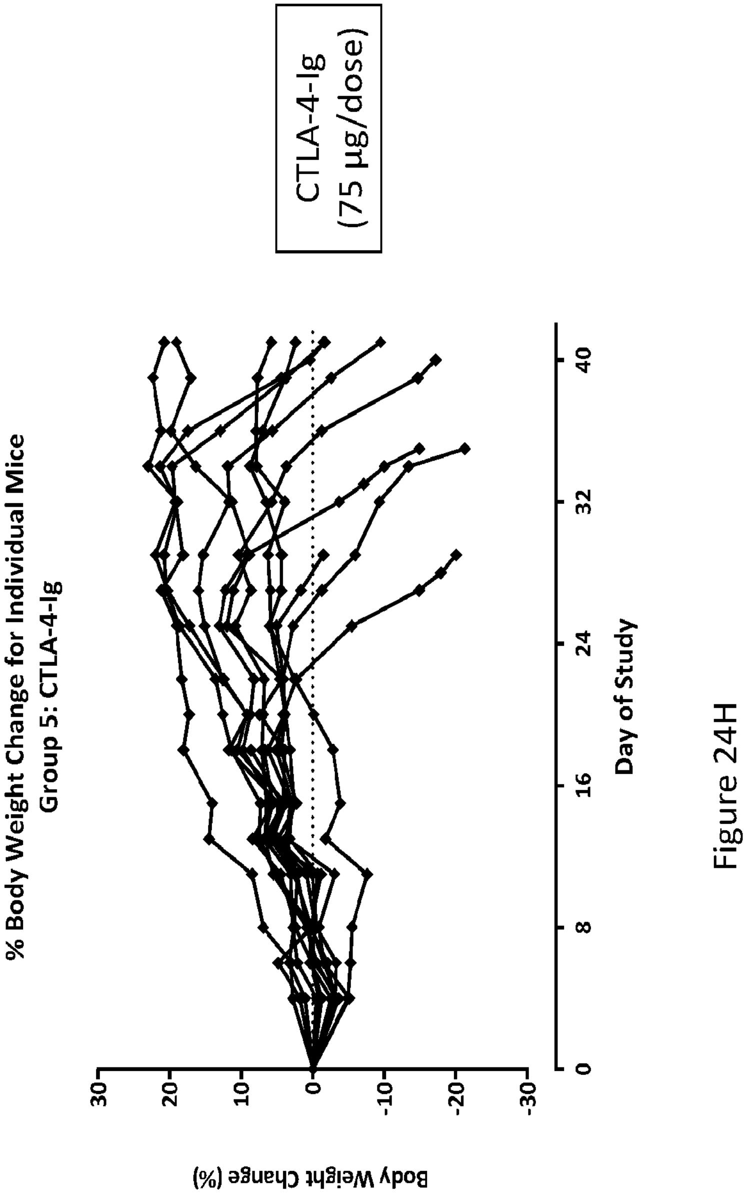

FIG. 24H is a graph depicting the results of the percent body weight change from start of study of individual animals for positive control CTLA-4-Ig during the time of the study.

DETAILED DESCRIPTION OF THE INVENTION

The invention provides a PD-1 binding agent. As discussed above, programmed death 1 (PD-1) (also known as programmed cell death 1) is a 268 amino acid type I transmembrane protein (Ishida et al., supra). PD-1 is a member of the CD28/CTLA-4 family of T-cell regulators and is reported to be expressed on activated T-cells, B-cells, and myeloid lineage cells (Greenwald et al., supra; and Sharpe et al., supra). PD-1 includes an extracellular IgV domain followed by short extracellular stalk, a transmembrane region and an intracellular tail. The PD-1 intracellular tail contains two phosphorylation sites located in an immunoreceptor tyrosine-based inhibitory motif and an immunoreceptor tyrosine-based switch motif, which when phosphorylated function to negatively regulate T-cell receptor signaling (see, e.g., Ishida et al., supra; and Blank et al., supra) by recruiting tyrosine phosphatases.

In some embodiments, the PD-1 binding agent provided herein is agonistic, meaning that the PD-1 binding agent binds to PD-1 but does not significantly inhibit binding of PD-1 to PD-1 ligand, thereby maintaining the ability of PD-1 to negatively regulate T-cell receptor signaling. According to certain embodiments, the PD-1 binding agents provided herein can induce or stimulate the ability of PD-1 to negatively regulate T-cell-receptor signaling and suppress an immune response. In a particular embodiment, there is provided a PD-1 binding agent that binds PD-1 at an epitope comprising, consisting essentially of, or consisting of, residues 33-41 of human PD1 (sequence: NPPTFSPAL) and/or 96-110 of human PD-1 (sequence: RVTQLPNGRDFHMSV).

The PD-1 binding agent comprises an immunoglobulin heavy chain variable region and an immunoglobulin light chain variable region, each of which comprise three complementarity determining regions (CDRs), usually referred to as CDR1, CDR2, or CDR3. The CDR regions also can be referred to using an "H" or "L" in the nomenclature to denote the heavy or light chain, respectively, i.e., CDRH1, CDRH2, CDRH3, CDRL1, CDRL2, or CDRL3. The CDRs of a given Ig sequence can be determined by any of several conventional numbering schemes, such as Kabat, Chothia, Martin (Enhanced Chothia), IGMT, or AHo (see, e.g., Kabat, et al., *Sequences of Proteins of Immunological Interest*, U.S. Department of Health and Human Services, NIH (1991); Chothia, et al., *Canonical Structures for the Hypervariable Regions of Immunoglobulins*, J. Mol. Biol., 196:901-917 (1987); Al-Lazikani et al., *Standard Conformations for the Canonical Structures of Immunoglobulins*, J. Mol. Biol., 273:927-948 (1997); Abhinandan et al., *Analysis and Improvements to Kabat and Structurally Correct Numbering of Antibody Variable Domains*, Mol. Immunol., 45: 3832-3839 (2008); Lefranc et al., *The IMGT unique numbering for immunoglobulins, T cell Receptors and Ig-like domains*, The Immunologist, 7: 132-136 (1999); Lefranc et al., *IMGT unique numbering for immunoglobulin and T cell receptor variable domains and I superfamily V-like domains*, Dev. Comp. Immunol., 27: 55-77 (2003); and Honegger et al., *Yet*

*another numbering scheme for immunoglobulin variable domains: an automatic modeling and analysis tool*, J. Mol. Biol. 309: 657-670 (2001).

According to one aspect of the invention, the immunoglobulin heavy chain variable region of the PD-1 binding agent comprises a CDR1 comprising SEQ ID NO: 1; a CDR2 comprising SEQ ID NO: 2; and a CDR3 comprising SEQ ID NO: 3; and the immunoglobulin light chain variable region comprises a CDR1 comprising SEQ ID NO: 4; a CDR2 comprising SEQ ID NO: 5; and a CDR3 comprising SEQ ID NO: 6. In some embodiments, the heavy chain CDR1 comprises any one of SEQ ID NOs: 13-18. In addition, or alternatively, some embodiments of the heavy chain CDR3 comprises any one of SEQ ID NOs: 19-21. Furthermore, the light chain CDR1 can comprise SEQ ID NO: 22 or 23.

In particular embodiments, the PD-1 binding agent can comprise an immunoglobulin heavy chain variable region of any one of SEQ ID NOs: 24-33, or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) to any one of SEQ ID NOs: 24-33. In other embodiments, the PD-1 binding agent comprises an immunoglobulin heavy chain variable region comprising the CDRs of any of SEQ ID NOs: 24-33, wherein the CDRs are as provided above or as determined in accordance with any of the various known immunoglobulin numbering schemes (e.g., Kabat, Chothia, Martin (Enhanced Chothia), IGMT, or AHo). Optionally, the immunoglobulin heavy chain variable region comprising the CDRs of any of SEQ ID NOs: 24-33 also has an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) to any of SEQ ID NOs: 24-33.

In addition to the Ig heavy chain variable region described above, or alternatively, the anti-PD-1 binding agent can comprise an immunoglobulin light chain variable region of SEQ ID NO: 34 or 35, or an amino acid sequence with at least 80%, 85%, or 90% sequence identity (e.g., at least 91%, at least 92%, at least 93%, at least 94%, at least 95%, at least 96%, at least 97%, at least 98%, at least 99%, or 100% sequence identity) to SEQ ID NOs: 34 or 35. In other embodiments, the PD-1 binding agent comprises an immunoglobulin light chain variable region comprising the CDRs of SEQ ID NO: 34 or 35, wherein the CDRs are as provided above or as determined in accordance with any of the various known immunoglobulin numbering schemes (e.g., Kabat, Chothia, Martin (Enhanced Chothia), IGMT, or AHo). Optionally, the immunoglobulin light chain variable region comprising the CDRs of SEQ ID NO: 34 or 35 also has an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) to SEQ ID NO: 34 or 35.

According to one embodiment, the PD-1 binding agent can comprise an immunoglobulin heavy chain variable region of SEQ ID NO: 29 or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) thereto; or an immunoglobulin heavy chain variable region comprising at least the CDRs of SEQ ID NO: 29, wherein the CDR regions are as provided above (e.g., CDR1—SEQ ID NO: 15, CDR2—SEQ ID NO: 2, and CDR3—SEQ ID NO: 20) or as determined in accordance with any of the various known immunoglobulin numbering schemes (e.g., Kabat, Chothia, Martin (Enhanced Chothia), IGMT, or AHo); and an immunoglobulin light chain variable region of SEQ ID NO: 35 or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) thereto, or an immunoglobulin light chain variable region comprising at least the CDRs of SEQ ID NO: 35; wherein the CDR regions are as provided above (e.g., CDR1—SEQ ID NO: 23, CDR2—SEQ ID NO: 5, and CDR3—SEQ ID NO: 6) or as determined in accordance with any of the various known immunoglobulin numbering schemes (e.g., Kabat, Chothia, Martin (Enhanced Chothia), IGMT, or AHo). In some embodiments, the antibody comprises a heavy chain variable region of SEQ ID NO: 29 and light chain variable region of SEQ ID NO: 35, or at least the CDRs thereof as determined by Kabat. In some embodiments, the antibody comprises a heavy chain variable region of SEQ ID NO: 29 and light chain variable region of SEQ ID NO: 35, or at least the CDRs thereof as determined by Chothia. In some embodiments, the antibody comprises a heavy chain variable region of SEQ ID NO: 29 and light chain variable region of SEQ ID NO: 35, or at least the CDRs thereof as determined by Martin. In some embodiments, the antibody comprises a heavy chain variable region of SEQ ID NO: 29 and light chain variable region of SEQ ID NO: 35, or at least the CDRs thereof as determined by IGMT. In some embodiments, the antibody comprises a heavy chain variable region of SEQ ID NO: 29 and light chain variable region of SEQ ID NO: 35, or at least the CDRs thereof as determined by AHo. By way of further example, the anti-PD-1 binding agent can comprise an immunoglobulin heavy chain comprising SEQ ID NO: 36 and an immunoglobulin light chain comprising SEQ ID NO: 37, or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) to SEQ ID NO: 36 and 37, respectively, optionally wherein the sequence retains the heavy chain and light chain CDRs of SEQ ID NO: 36 and 37, respectively, wherein the CDRs are as provided above or as determined in accordance with any of the various known immunoglobulin numbering schemes (e.g., Kabat, Chothia, Martin (Enhanced Chothia), IGMT, or AHo).

According to another embodiment, the PD-1 binding agent can comprise an immunoglobulin heavy chain variable region of SEQ ID NO: 24 or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) thereto; or an immunoglobulin heavy chain variable region comprising at least the CDRs of SEQ ID NO: 24, wherein the CDR regions are as provided above (e.g., CDR1—SEQ ID NO: 13, CDR2—SEQ ID NO: 2, and CDR3—SEQ ID NO: 19) or as determined in accordance with any of the various known immunoglobulin numbering schemes (e.g., Kabat, Chothia, Martin (Enhanced Chothia), IGMT, or AHo); and an immunoglobulin light chain variable region of SEQ ID NO: 34 or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) thereto, or an immunoglobulin light chain variable region comprising at least the CDRs of SEQ ID NO: 34; wherein the CDR regions are as provided above (e.g., CDR1—SEQ ID NO: 22, CDR2—SEQ ID NO: 5, and CDR3—SEQ ID NO: 6) or as determined in accordance with any of the various known immunoglobulin numbering schemes (e.g., Kabat, Chothia, Martin (Enhanced Chothia), IGMT, or AHo). In some embodiments, the antibody comprises a heavy chain variable region of SEQ ID NO: 24 and light chain variable region of SEQ ID NO: 34, or at least the CDRs thereof as determined by Kabat. In some embodiments, the antibody comprises a heavy chain variable region of SEQ ID NO: 24 and light chain variable region of SEQ ID NO: 34, or at least the CDRs thereof as determined by Chothia. In some embodiments, the antibody comprises a heavy chain variable region of SEQ ID NO: 24 and light chain variable region of SEQ ID NO: 34, or at least the CDRs thereof as determined by Martin. In some embodiments, the antibody comprises a heavy chain variable region of SEQ ID NO: 24 and light chain variable region of SEQ ID NO: 34, or at least the CDRs thereof as determined by IGMT. In some embodiments, the antibody comprises a heavy chain variable region of SEQ ID NO: 24 and light chain variable region of SEQ ID NO: 34, or at least the CDRs thereof as determined by AHo.

According to one embodiment, the PD-1 binding agent can comprise an immunoglobulin heavy chain variable region of SEQ ID NO: 30 or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) thereto; or an immunoglobulin heavy chain variable region comprising at least the CDRs of SEQ ID NO: 30, wherein the CDR regions are as provided above (e.g., CDR1—SEQ ID NO: 15, CDR2—SEQ ID NO: 2, and CDR3—SEQ ID NO: 21) or as determined in accordance with any of the various known immunoglobulin numbering schemes (e.g., Kabat, Chothia, Martin (Enhanced Chothia), IGMT, or AHo); and an immunoglobulin light chain variable region of SEQ ID NO: 35 or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) thereto, or an immunoglobulin light chain variable region comprising at least the CDRs of SEQ ID NO: 35; wherein the CDR regions are as provided above (e.g., CDR1—SEQ ID NO: 23, CDR2—SEQ ID NO: 5, and CDR3—SEQ ID NO: 6) or as determined in accordance with any of the various known immunoglobulin numbering schemes (e.g., Kabat, Chothia, Martin (Enhanced Chothia), IGMT, or AHo). In some embodiments, the antibody comprises a heavy chain variable region of SEQ ID NO: 30 and light chain variable region of SEQ ID NO: 35, or at least the CDRs thereof as determined by Kabat. In some embodiments, the antibody comprises a heavy chain variable region of SEQ ID NO: 30 and light chain variable region of SEQ ID NO: 35, or at least the CDRs thereof as determined by Chothia. In some embodiments, the antibody comprises a heavy chain variable region of SEQ ID NO: 30 and light chain variable region of SEQ ID NO: 35, or at least the CDRs thereof as determined by Martin. In some embodiments, the antibody comprises a heavy chain variable region of SEQ ID NO: 30 and light chain variable region of SEQ ID NO: 35, or at least the CDRs thereof as determined by IGMT. In some embodiments, the antibody comprises a heavy chain variable region of SEQ ID NO: 30 and light chain variable region of SEQ ID NO: 35, or at least the CDRs thereof as determined by AHo.

According to another aspect, the anti-PD-1 binding agent comprises an immunoglobulin heavy chain variable region comprising: a CDR1 comprising SEQ ID NO: 7; a CDR2 comprising SEQ ID NO: 8; and a CDR3 comprising SEQ ID NO: 9; and an immunoglobulin light chain variable region comprising a CDR1 comprising SEQ ID NO: 10; a CDR2 comprising SEQ ID NO: 11; and a CDR3 comprising SEQ ID NO: 12. In some embodiments, the heavy chain CDR1 comprises any of SEQ ID NOs: 57-60. In some embodiments, the heavy chain CDR2 comprises any one of SEQ ID NOs: 38-42.

In some embodiments, the PD-1 binding agent comprises an immunoglobulin heavy chain variable region of any one of SEQ ID NOs: 43-47 or 61-63, or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) to any one of SEQ ID NOs: 43-47 or 61-63. In some embodiments, the PD-1 binding agent comprises an immunoglobulin heavy chain variable region comprising the CDRs of any of SEQ ID NOs: 43-47 or 61-63, wherein the CDRs are as provided above or as determined in accordance with any of the various known immunoglobulin numbering schemes (e.g., Kabat, Chothia, Martin (Enhanced Chothia), IGMT, or AHo). Optionally, the immunoglobulin heavy chain variable region comprising the CDRs of any of SEQ ID NOs: 43-47 or 61-63 also has an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) to any one of SEQ ID NOs: 43-47 or 61-63.

In addition to the Ig heavy chain variable region described above (e.g., SEQ ID NOs: 43-47 or 61-63), or alternatively, the anti-PD-1 binding agent can comprise an immunoglobulin light chain variable region of any of SEQ ID NOs: 48-50, or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) to any one of SEQ ID NOs: 48-50. In other embodiments, the PD-1 binding agent comprises an immunoglobulin light chain variable region comprising the CDRs of any of SEQ ID NOs: 48-50, wherein the CDRs are as provided above or as determined in accordance with any of the various known immunoglobulin numbering schemes (e.g., Kabat, Chothia, Martin (Enhanced Chothia), IGMT, or AHo). Optionally, the immunoglobulin light chain variable region comprising the CDRs of any of SEQ ID NOs: 48-50 also has an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) to any of SEQ ID NOs: 48-50.

In a particular embodiment, the anti-PD-1 binding agent comprises an immunoglobulin heavy chain variable region of SEQ ID NO: 47, or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) to SEQ ID NO: 47; or an immunoglobulin heavy chain variable region comprising at least the CDRs of SEQ ID NO: 47, wherein the CDR regions are as provided above (e.g., CDR1—SEQ ID NO: 57, CDR2—SEQ ID NO: 42, and CDR3—SEQ ID NO: 9) or as determined in accordance with any of the various known immunoglobulin numbering schemes (e.g., Kabat, Chothia, Martin (Enhanced Chothia), IGMT, or AHo); and an immunoglobulin light chain variable region of SEQ ID NO: 49, or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) to SEQ ID NO: 49; or an immunoglobulin heavy chain variable region comprising at least the CDRs of SEQ ID NO: 49; wherein the CDR regions are as provided above (e.g., CDR1—SEQ ID NO: 10, CDR2—SEQ ID NO: 11, and CDR3—SEQ ID NO: 12) or as determined in accordance with any of the various known immunoglobulin numbering schemes (e.g., Kabat, Chothia, Martin (Enhanced Chothia), IGMT, or AHo). In some embodiments, the antibody comprises a heavy chain variable region of SEQ ID NO: 47 and light chain variable region of SEQ ID NO: 49, or at least the CDRs thereof as determined by Kabat. In some embodiments, the antibody comprises a heavy chain variable region of SEQ ID NO: 47 and light chain variable region of SEQ ID NO: 49, or at least the CDRs thereof as determined by Chothia. In some embodiments, the antibody comprises a heavy chain variable region of SEQ ID NO: 47 and light chain variable region of SEQ ID NO: 49, or at least the CDRs thereof as determined by Martin. In some embodiments, the antibody comprises a heavy chain variable region of SEQ ID NO: 47 and light chain variable region of SEQ ID NO: 49, or at least the CDRs thereof as determined by IGMT. In some embodiments, the antibody comprises a heavy chain variable region of SEQ ID NO: 47 and light chain variable region of SEQ ID NO: 49, or at least the CDRs thereof as determined by AHo. By way of further example, the anti-PD-1 binding agent can comprise an immunoglobulin heavy chain comprising SEQ ID NO: 51 and an immunoglobulin light chain comprising SEQ ID NO: 52, or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) to SEQ ID NOs: 51 and 52, optionally wherein the sequence retains the heavy chain and light chain CDRs of SEQ ID NOs: 51 and 52 as provided above or as determined in accordance with any of the various known immunoglobulin numbering schemes (e.g., Kabat, Chothia, Martin (Enhanced Chothia), IGMT, or AHo).

In another embodiment, the anti-PD-1 binding agent comprises an immunoglobulin heavy chain variable region of SEQ ID NO: 46, or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) to SEQ ID NO: 46; or an immunoglobulin heavy chain variable region comprising at least the CDRs of SEQ ID NO: 46, wherein the CDR regions are as provided above (e.g., CDR1—SEQ ID NO: 57, CDR2—SEQ ID NO: 41, and CDR3—SEQ ID NO: 9) or as determined in accordance with any of the various known immunoglobulin numbering schemes (e.g., Kabat, Chothia, Martin (Enhanced Chothia), IGMT, or AHo); and an immunoglobulin light chain variable region of SEQ ID NO: 50, or an amino acid sequence with at least 80%, 85%, or 90% sequence identity (e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity) to SEQ ID NO: 50; or an immunoglobulin heavy chain variable region comprising at least the CDRs of SEQ ID NO: 50; wherein the CDR regions are as provided above (e.g., CDR1—SEQ ID NO: 10, CDR2—SEQ ID NO: 11, and CDR3—SEQ ID NO: 12) or as determined in accordance with any of the various known immunoglobulin numbering schemes (e.g., Kabat, Chothia, Martin (Enhanced Chothia), IGMT, or AHo). In some embodiments, the antibody comprises a heavy chain variable region of SEQ ID NO: 46 and light chain variable region of SEQ ID NO: 50, or at least the CDRs thereof as determined by Kabat. In some embodiments, the antibody comprises a heavy chain variable region of SEQ ID NO: 46 and light chain variable region of SEQ ID NO: 50, or at least the CDRs thereof as determined by Chothia. In some embodiments, the antibody comprises a heavy chain variable region of SEQ ID NO: 46 and light chain variable region of SEQ ID NO: 50, or at least the CDRs thereof as determined by Martin. In some embodiments, the antibody comprises a heavy chain variable region of SEQ ID NO: 46 and light chain variable region of SEQ ID NO: 50, or at least the CDRs thereof as determined by IGMT. In some embodiments, the antibody comprises a heavy chain variable region of SEQ ID NO: 46 and light chain variable region of SEQ ID NO: 50, or at least the CDRs thereof as determined by AHo.

Sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FAS™, and SSEARCH) (for sequence alignment and sequence similarity searches). Sequence alignment algorithms also are disclosed in, for example, Altschul et al., *J. Molecular Biol.,* 215(3): 403-410 (1990), Beigert et al., *Proc. Natl. Acad. Sci. USA,* 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics,* 21(7): 951-960 (2005), Altschul et al., *Nucleic Acids Res.,* 25(17): 3389-3402 (1997), and Gusfield, *Algorithms on Strings, Trees and Sequences*, Cambridge University Press, Cambridge UK (1997)).

Variation in sequence identity can be accomplished through addition, substitution, or deletion of one or more amino acid residues. An amino acid "replacement" or "substitution" refers to the replacement of one amino acid at a given position or residue by another amino acid at the same position or residue within a polypeptide sequence. The amino acid replacement or substitution can be conservative, semi-conservative, or non-conservative depending upon whether the substitution is by an amino acid residue that has similar properties to the residue being replaced. A functional way to define common properties between individual amino acids is to analyze the normalized frequencies of amino acid changes between corresponding proteins of homologous organisms (Schulz and Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Amino acids can be broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —$NH_2$ can be maintained. "Semi-conservative mutations" include amino acid substitutions of amino acids within the same groups listed herein, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

In some embodiments, the PD-1-binding agent can comprise, consist essentially of, or consist of the immunoglobulin heavy and light chain variable region or full heavy and light chain polypeptides provided herein. The isolated PD-1-binding agent can be any type of molecule or construct comprising at least the specified immunoglobulin heavy and light chain variable regions. Thus, the PD-1 binding agent can be, for instance, a whole immunoglobulin or antibody, as described herein, or an antigen-binding (PD-1 binding) immunoglobulin or antibody "fragment." The term "fragment" used with respect to an antibody or immunoglobulin means any molecule or construct that comprises some part of an immunoglobulin or antibody and binds the target antigen. Such a fragment will generally comprise at least the parts of the heavy and light chain variable regions including the CDRs, and may also include parts of the constant regions, optionally along with other elements that are not normally part of an immunoglobulin or antibody (e.g., linkers, etc.). Examples of such "fragments" include, but are not limited to, (i) a Fab fragment, which is a monovalent fragment consisting of the $V_L$, $V_H$, $C_L$, and $CH_1$ domains, (ii) a $F(ab')_2$ fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an $F(ab')_2$ fragment using mild reducing conditions; (v) a diabody; (vi) a single-chain variable region (scFv), and (vii) a disulfide-stabilized Fv fragment (dsFv).

In some embodiments, the PD-1-binding agent comprises an immunoglobulin heavy chain constant region, such as a fragment crystallizable ($F_c$) region or portion thereof. The Fc region can be of any Ig class/subclass (IgA (IgA1, IgA2), IgD, IgE, IgG (IgG1, IgG2, IgG3 and IgG4), IgM, including variants thereof. In a particular embodiment, the PD-1 binding agent comprises an Fc region that binds an Fc receptor of an antigen-presenting cell (e.g., dendritic cell, macrophage, Langerhans cell, or B cell). The Fc receptor can be an Fcγ receptor (FcγR), such as FcγRI (CD64), FcγRIIA (CD32), FcγRIIB (CD32), FcγRIIIA (CD16a), FcγRIIIB (CD16b). In one embodiment, the PD-1 binding agent comprises an Fc region that binds FcγR, such as IgG1. Thus, in some embodiments, the PD-1 binding agent is a "whole" or "complete" Ig (i.e., an antibody). In additional embodiments, the PD-1 binding agent is an IgG antibody, particularly an IgG1 antibody.

The isolated PD-1-binding agent also can be an antibody conjugate. In this respect, the isolated PD-1-binding agent can be a conjugate comprising the PD-1-binding agent (e.g., anti-PD-1 antibody or antibody fragment) and another biologically active moiety. For example, the PD-1-binding agent can be conjugated to a peptide, a fluorescent molecule, or a chemotherapeutic agent, particularly an agent useful in suppressing an immune response.

The isolated PD-1-binding agent can be, or can be obtained from, a human antibody, a non-human antibody, or a chimeric antibody. By "chimeric" is meant an antibody or fragment thereof comprising both human and non-human regions. Preferably, the isolated PD-1-binding agent is a humanized antibody. A "humanized" antibody is a monoclonal antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. In a preferred embodiment of the invention, CDRH3 of the inventive PD-1-binding agent is obtained or derived from a mouse monoclonal antibody, while the remaining variable regions and constant region of the inventive PD-1-binding agent are obtained or derived from a human monoclonal antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents). Methods for generating antibodies are known in the art and are described in, for example, Köhler and Milstein, *Eur. J. Immunol.,* 5: 511-519 (1976); Harlow and Lane (eds.), *Antibodies: A Laboratory Manual*, CSH Press (1988); and Janeway et al. (eds.), *Immunobiology,* 5th Ed., Garland Publishing, New York, NY (2001); Starkie et al., *PLoS One,* 11(3): e0152282 (2016)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin T C MOUSE™, and the Kyowa Kirin K M-MOUSE™ (see, e.g., Lonberg, Nat. Biotechnol., 23(9): 1117-25 (2005), and Lonberg, *Handb. Exp. Pharmacol.,* 181: 69-97 (2008)). A humanized antibody can be generated using any suitable method known in the art (see, e.g., An, Z. (ed.), *Therapeutic Monoclonal Antibodies: From Bench to Clinic*, John Wiley & Sons, Inc., Hoboken, New Jersey (2009)), including, e.g., grafting of non-human CDRs onto a human antibody scaffold (see, e.g., Kashmiri et al., *Methods,* 36(1): 25-34 (2005); and Hou et al., *J. Biochem.,* 144(1): 115-120 (2008)). In one embodiment, a humanized antibody can be produced using the methods described in, e.g., U.S. Patent Application Publication 2011/0287485 A1.

The PD-1 binding agent can have any suitable affinity for human PD-1. The term "affinity" refers to the equilibrium constant for the reversible binding of two agents and is expressed as the dissociation constant ($K_D$). Affinity of a binding agent to a ligand, such as affinity of an antibody for an epitope, can be, for example, from about 1 picomolar (μM) to about 100 micromolar (μM) (e.g., from about 1 picomolar (μM) to about 1 nanomolar (nM), from about 1 nM to about 1 micromolar (μM), or from about 1 μM to about 100 μM). In one embodiment, the PD-1-binding agent can bind to an PD-1 protein with a $K_D$ less than or equal to 1 nM (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In another embodiment, the PD-1-binding agent can bind to PD-1 with a $K_D$ less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values). In some embodiments, the PD-1 binding agent is cross-reactive with cynomolgus PD-1 with an affinity in any of the foregoing ranges discussed with respect to human PD-1. Immunoglobulin affinity for an antigen or epitope of interest can be measured using any art-recognized assay. Such methods include, for example, fluorescence activated cell sorting (FACS), separable beads (e.g., magnetic beads), surface plasmon resonance (SPR), solution phase competition (KinExA®), antigen panning, and/or ELISA (see, e.g., Janeway et al. (eds.), *Immunobiology,* 5th ed., Garland Publishing, New York, NY, 2001).

The PD-1 binding agent binds PD-1, but preferably does not completely inhibit the ability of PD-1 to negatively regulate an immune response or, in some cases, does not substantially inhibit the ability of PD-1 to negatively regulate an immune response or even enhances the ability of PD-1 to negatively regulate an immune response. In some embodiments, the PD-1 binding agent does not completely block binding between PD-1 and PD-L1, or, preferably, does not substantially reduce binding between PD-1 and PD-L1. Assessment of the degree to which a PD-1 binding agent inhibits PD-1 regulation of an immune response or PD-1 binding to PD-L1 can be performed using assays such as those set forth in the examples or other assays known in the art. In some embodiments, the PD-1 binding agent inhibits PD-1 binding to PD-L1 by no more than about 80%, by no more than about 75%, by no more than about 70%, by no more than about 65%, by no more than about 60%, by no more than about 55%, by no more than about 50%, by no more than about 45%, by no more than about 40%, by no more than about 35%, by no more than about 30%, by no more than about 25%, by no more than about 20%, by no more than about 15%, by no more than about 10%.

Methods of Use/Treatment

The invention provides a method of suppressing an immune response, particularly a T-cell mediated immune response, in a mammal by administering to the mammal the PD-1 binding agent described herein. The invention further provides a method of treating a disease or disorder in which a decrease in PD-1 activity (e.g., a decrease in PD-1 signaling through decreased PD-L1 binding, such as a decrease in negative regulation of the immune system) causes or contributes to the pathological effects of the disease, or any disease or disorder in which an increase in PD-1 activity (e.g., an increase in PD-1 signaling through PD-L1 binding, such as an increase in negative regulation of the immune system) would have a therapeutic benefit, which method comprises administering to a mammal the PD-1 binding agent described herein to reduce or eliminate any symptom of the disorder, or prevent or inhibit the onset of such symptoms. Negative regulation of the immune system as used herein in synonymous with immunosuppression. It will be appreciated that the PD-1 binding agent can be administered prior to the onset of symptoms in some instances (e.g., prior to exposure to an antigen that triggers an immune response) so as to prevent, suppress, or reduce the severity of an immune response upon introduction of the antigen.

The disease or disorder can be an inflammatory or autoimmune disorder. Examples of inflammatory or autoimmune disorders include, for example, infections (viral, bacterial, fungal and parasitic), endotoxic shock associated with infection, arthritis, rheumatoid arthritis, asthma, Chronic obstructive pulmonary disease (COPD), pelvic inflammatory disease, Behcet disease, Alzheimer's Disease, inflammatory bowel disease including Crohn's disease and ulcerative colitis, Peyronie's Disease, coeliac disease, gallbladder disease, Pilonidal disease, peritonitis, psoriasis, psoriatic arthritis, vasculitis, antineutrophil cytoplasmic antibody-associated (ANCA) vasculitis, surgical adhesions, stroke, Type I Diabetes, lyme disease, arthritis, meningoencephalitis, autoimmune uveitis, immune mediated inflammatory disorders of the central and peripheral nervous system such as multiple sclerosis, lupus (such as systemic lupus erythematosus and chronic discoid lupus erythematosus) and Guillain-Barr syndrome, Atopic dermatitis, polymyositis, dermatomyositis, autoimmune hepatitis, fibrosing alveolitis, Grave's disease, IgA nephropathy, idiopathic thrombocytopenic purpura, Meniere's disease, pemphigus, pemphigoid, primary biliary cholangitis, hepatitis, sarcoidosis, scleroderma (localized scleroderma, systemic scleroderma, and progressive systemic scleroderma), Ganulomatosis with polyangiitis, other autoimmune disorders, cholangitis, pancreatitis, trauma (surgery), graft-versus-host disease, transplant rejection, heart disease including ischaemic diseases such as myocardial infarction as well as atherosclerosis, periarteritis nodosa (polyarteritis nodosa and microscopic polyangiitis), allergic granulomatous angiitis, hypersensitivity angiitis, aortitis syndrome (Takayasu arteritis), temporal arteritis, intravascular coagulation, bone resorption, osteoporosis, osteoarthritis, periodontitis and hypochlorhydia, Still's disease, Cogan's syndrome, RS3PE, polymyalgia rheumatica, fibromyalgia syndrome, antiphospholipid antibody syndrome, eosinophilic fasciitis, Guillain-Barre syndrome, myasthenia gravis, chronic atrophic gastritis, Goodpasture's syndrome, rapidly progressive glomerulonephritis, megaloblastic anemia, hemolytic anemia, autoimmune neutropenia, Hashimoto's thyroiditis, autoimmune adrenal insufficiency, primary hypothyroidism, idiopathic Addison's disease (chronic adrenal insufficiency), herpes gestationis, linear IgA bullous skin disease, epidermolysis bullosa acquisita, alopecia areata, vitiligo, Harada disease, autoimmune optic neuropathy, idiopathic azoospermia, recurrent fetal loss, or infertility related to lack of fetal-maternal tolerance.

In some embodiments, the disease or disorder is Giant Cell Arteritis, Polymyalgia Rheumatica, Primary Sjögren's Syndrome, TNF-refractory Rheumatoid Arthritis, Alopecia Areata, Primary Biliary Cholangitis (PBC), Graft vs Host Disease (GvHD), Vitiligo, ANCA Vasculitis, Type 1 Diabetes, or Noninfectious Uveitis.

An "immune response" can entail, for example, antibody production and/or the activation of immune effector cells (e.g., T-cells), production of inflammatory cytokines, or any of the indications or disorders described herein or otherwise known in the art. As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the PD-1-binding agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the PD-1-binding agent to elicit a desired response in the individual.

Alternatively, the pharmacologic and/or physiologic effect may be prophylactic, i.e., the effect completely or partially prevents a disease or symptom thereof. In this respect, the inventive method comprises administering a "prophylactically effective amount" of the PD-1-binding agent. A "prophylactically effective amount" refers to an amount effective, at dosages and for periods of time necessary, to achieve a desired prophylactic result (e.g., prevention of disease onset).

The PD-1 binding agent can be part of a composition suitable for administration to a mammal. Preferably, the composition is a pharmaceutically acceptable (e.g., physiologically acceptable) composition, which comprises a carrier, preferably a pharmaceutically acceptable (e.g., physiologically acceptable) carrier, and the inventive amino acid sequences, antigen-binding agent, or vector. Any suitable carrier can be used within the context of the invention, and such carriers are well known in the art. The choice of carrier will be determined, in part, by the particular site to which the composition may be administered and the particular method used to administer the composition. The composition also can comprise any other excipient used in the formulation of therapeutic molecules (e.g., proteins or antibodies), particularly parenteral formulations, including, for instance, buffers, tonicity modifiers, stabilizers, surfactants and the like. The composition optionally can be sterile. The composition can be frozen or lyophilized for storage and reconstituted in a suitable sterile carrier prior to use. The compositions can be generated in accordance with conventional techniques described in, e.g., Remington: *The Science and Practice of Pharmacy,* 21st Edition, Lippincott Williams & Wilkins, Philadelphia, PA (2001).

A typical dose of the PD-1 binding agent can be, for example, in the range of 1 pg/kg to 20 mg/kg of animal or human body weight; however, doses below or above this exemplary range are within the scope of the invention. The daily parenteral dose can be about 0.00001 μg/kg to about 20 mg/kg of total body weight (e.g., about 0.001 μg/kg, about 0.1 μg/kg, about 1 μg/kg, about 5 μg/kg, about 10 μg/kg, about 100 μg/kg, about 500 μg/kg, about 1 mg/kg, about 5 mg/kg, about 10 mg/kg, or a range defined by any two of the foregoing values), preferably from about 0.1 μg/kg to about 10 mg/kg of total body weight (e.g., about 0.5 μg/kg, about 1 μg/kg, about 50 μg/kg, about 150 μg/kg, about 300 μg/kg, about 750 μg/kg, about 1.5 mg/kg, about 5 mg/kg, or a range defined by any two of the foregoing values), more preferably from about 1 μg/kg to 5 mg/kg of total body weight (e.g., about 3 μg/kg, about 15 μg/kg, about 75 μg/kg, about 300 μg/kg, about 900 μg/kg, about 2 mg/kg, about 4 mg/kg, or a range defined by any two of the foregoing values), and even more preferably from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment can be repeated until a desired suppression of disease symptoms occurs.

However, other dosage regimens may be useful and are within the scope of the invention. The desired dosage can be delivered by a single bolus administration of the composition, by multiple bolus administrations of the composition, or by continuous infusion administration of the composition.

The PD-1-binding agent can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

Once administered to a mammal (e.g., a human), the biological activity of the inventive PD-1-binding agent can be measured by any suitable method known in the art. For example, the biological activity can be assessed by determining the stability of a particular PD-1-binding agent. In one embodiment of the invention, the PD-1-binding agent (e.g., an antibody) has an in vivo half-life between about 30 minutes and 45 days (e.g., about 30 minutes, about 45 minutes, about 1 hour, about 2 hours, about 4 hours, about 6 hours, about 10 hours, about 12 hours, about 1 day, about 5 days, about 10 days, about 15 days, about 25 days, about 35 days, about 40 days, about 45 days, or a range defined by any two of the foregoing values). In another embodiment, the PD-1-binding agent has an in vivo half-life between about 2 hours and 20 days (e.g., about 5 hours, about 10 hours, about 15 hours, about 20 hours, about 2 days, about 3 days, about 7 days, about 12 days, about 14 days, about 17 days, about 19 days, or a range defined by any two of the foregoing values). In another embodiment, the PD-1-binding agent has an in vivo half-life between about 10 days and about 40 days (e.g., about 10 days, about 13 days, about 16 days, about 18 days, about 20 days, about 23 days, about 26 days, about 29 days, about 30 days, about 33 days, about 37 days, about 38 days, about 39 days, about 40 days, or a range defined by any two of the foregoing values).

The PD-1-binding agent of the invention may be administered alone or in combination with other active agents or drugs. For example, the PD-1-binding agent can be administered in combination with other agents for the treatment or prevention of the diseases disclosed herein. In this respect, the PD-1-binding agent can be used in combination with at least one other inflammatory or autoimmune disorder inhibiting agent including, for example, other monoclonal antibodies, disease-killing viruses, gene therapy, and adoptive T-cell transfer, and/or surgery. The inventive PD-1-binding agent described herein can also be used in combination with at least one other immunosuppressive agent, including, for example, methotrexate, corticosteroids, and other small molecule agents used to treat autoimmune and inflammatory disease. When the inventive method treats an infectious disease, the PD-1-binding agent can be administered in combination with at least one anti-bacterial agent or at least one anti-viral agent. In this respect, the anti-bacterial agent can be any suitable antibiotic known in the art. The anti-viral agent can be any vaccine of any suitable type that specifically targets a particular virus (e.g., live-attenuated vaccines, subunit vaccines, recombinant vector vaccines, and small molecule anti-viral therapies (e.g., viral replication inhibitors and nucleoside analogs).

In addition to therapeutic uses, the PD-1-binding agent described herein can be used in diagnostic or research applications. In this respect, the PD-1-binding agent can be used in a method to diagnose a cancer or infectious disease. In a similar manner, the PD-1-binding agent can be used in an assay to monitor PD-1 protein levels in a subject being tested for a disease or disorder that is associated with abnormal PD-1 expression. Research applications include, for example, methods that utilize the PD-1-binding agent and a label to detect a PD-1 protein in a sample, e.g., in a human body fluid or in a cell or tissue extract. The PD-1-binding agent can be used with or without modification, such as covalent or non-covalent labeling with a detectable moiety. For example, the detectable moiety can be a radioisotope (e.g., $^{3}H$, $^{14}C$, $^{32}P$, $^{35}S$, or $^{125}I$), a fluorescent or chemiluminescent compound (e.g., fluorescein isothiocyanate, rhodamine, or luciferin), an enzyme (e.g., alkaline phosphatase, beta-galactosidase, or horseradish peroxidase), or prosthetic groups. Any method known in the art for separately conjugating an antigen-binding agent (e.g., an antibody) to a detectable moiety may be employed in the context of the invention (see, e.g., Hunter et al., *Nature,* 194: 495-496 (1962); David et al., *Biochemistry,* 13: 1014-1021 (1974); Pain et al., *J. Immunol. Meth.,* 40: 219-230 (1981); and Nygren, *J. Histochem. Cytochem.,* 30: 407-412 (1982)).

PD-1 protein levels can be measured using the inventive PD-1-binding agent by any suitable method known in the art. Such methods include, for example, radioimmunoassay (RIA), and FACS. Normal or standard expression values of PD-1 protein can be established using any suitable technique, e.g., by combining a sample comprising, or suspected of comprising, a PD-1 polypeptide with a PD-1-specific antibody under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, *Monoclonal Antibodies: A Manual of Techniques*, CRC Press, Inc. (1987)). The amount of PD-1 polypeptide expressed in a sample is then compared with a standard value.

The PD-1-binding agent can be provided in a kit, i.e., a packaged combination of reagents in predetermined amounts with instructions for performing a diagnostic assay. If the PD-1-binding agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

Nucleic Acids, Cells, Methods of Production

The invention also provides one or more isolated or purified nucleic acid sequences that encode the PD-1 binding agent or individual heavy or light chain immunoglobulin polypeptides thereof. Thus, in one embodiment, the nucleic acid encodes an immunoglobulin light chain variable region or full immunoglobulin light chain as provided herein. In another embodiment, the nucleic acid encodes an immunoglobulin heavy chain variable region or full immunoglobulin light chain as provided herein. In yet another embodiment, the nucleic acid encodes both an immunoglobulin light chain variable region or full immunoglobulin light chain, and an immunoglobulin heavy chain variable region or full immunoglobulin heavy chain, as provided herein. Examples of a nucleic acid sequence encoding an immunoglobulin heavy chain are provided by SEQ ID NOs: 53 and 55, which encode the heavy chain variable regions of SEQ ID NOs: 29 and 47, respectively, and the full heavy and light chains of SEQ ID NOs: 36 and 51, respectively. Examples of a nucleic acid sequence encoding an immunoglobulin light chain are provided by SEQ ID NOs: 54 and 56, which encode the light chain variable region of SEQ ID NOs: 35 and 49, respectively, and the full heavy and light chains of SEQ ID NOs: 37 and 52, respectively.

The terms "nucleic acid" and "nucleic acid sequence" are intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

The nucleic acid can be part of a vector. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual,* 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

In addition to the nucleic acid sequence encoding the immunoglobulin heavy and/or light chains, the vector can comprise expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include, for example, the Tet system (U.S. Pat. Nos. 5,464,758 and 5,814,618), the Ecdysone inducible system (No et al., *Proc. Natl. Acad. Sci.,* 93: 3346-3351 (1996)), the T-REX™ system (Invitrogen, Carlsbad, CA), LACSWITCH™ system (Stratagene, San Diego, CA), and the Cre-ERT tamoxifen inducible recombinase system (Indra et al., *Nuc. Acid. Res.,* 27: 4324-4327 (1999); *Nuc. Acid. Res.,* 28: e99 (2000); U.S. Pat. No. 7,112,715; and Kramer & Fussenegger, *Methods Mol. Biol.,* 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences.

The vector also can comprise a selectable marker gene. The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 1992/008796 and WO 1994/028143; Wigler et al., *Proc. Natl. Acad. Sci. USA,* 77: 3567-3570 (1980); O'Hare et al., *Proc. Natl. Acad. Sci. USA,* 78: 1527-1531 (1981); Mulligan & Berg, *Proc. Natl. Acad. Sci. USA,* 78: 2072-2076 (1981); Colberre-Garapin et al., *J. Mol. Biol.,* 150: 1-14 (1981); Santerre et al., *Gene,* 30: 147-156 (1984); Kent et al., *Science,* 237: 901-903 (1987); Wigler et al., *Cell,* 11: 223-232 (1977); Szybalska & Szybalski, *Proc. Natl. Acad. Sci. USA,* 48: 2026-2034 (1962); Lowy et al., *Cell,* 22: 817-823 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy,* 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, CA) and pBK-CMV from Stratagene (La Jolla, CA) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, CA) (e.g., pcDNA™5/FRT), or the cre-lox system, such as can be found in the pExchange-6 Core Vectors from Stratagene (La Jolla, CA). Examples of vectors that randomly integrate into host cell chromosomes include, for example, pcDNA3.3

(when introduced in the absence of T-antigen) from ThermoFisher (Carlsbad, CA), UCOE from Millipore (Billerica, MA), and pCI or pFN10A (ACT) FLEXI™ from Promega (Madison, WI).

Viral vectors also can be used. Representative commercially available viral expression vectors include, but are not limited to, the adenovirus-based Per.C6 system available from Crucell, Inc. (Leiden, The Netherlands), the lentiviral-based pLP1 from ThermoFisher (Carlsbad, CA), and the retroviral vectors pFB-ERV plus pCFB-EGSH from Agilent (Stratagene, La Jolla, CA).

Nucleic acid sequences encoding the inventive amino acid sequences can be provided to a cell on the same vector (i.e., in cis). A unidirectional promoter can be used to control expression of each nucleic acid sequence. In another embodiment, a combination of bidirectional and unidirectional promoters can be used to control expression of multiple nucleic acid sequences. Nucleic acid sequences encoding the inventive amino acid sequences alternatively can be provided to the population of cells on separate vectors (i.e., in trans). Each of the nucleic acid sequences in each of the separate vectors can comprise the same or different expression control sequences. The separate vectors can be provided to cells simultaneously.

The vector(s) comprising the nucleic acid(s) encoding the inventive amino acid sequences can be introduced into a host cell that is capable of expressing the polypeptides encoded thereby, including any suitable prokaryotic or eukaryotic cell. As such, the invention provides an in vitro cell or cell line comprising the inventive vector. The invention also provides an in vitro cell or cell line that expresses the immunoglobulin heavy and/or light chain polypeptides, or expresses the PD-1 binding agent. Preferred host cells are those that can be easily and reliably grown, have reasonably fast growth rates, have well characterized expression systems, and can be transformed or transfected easily and efficiently.

Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella*, and *Erwinia*. Particularly useful prokaryotic cells include the various strains of *Escherichia coli* (e.g., K12, HB101 (ATCC No. 33694), DH5a, DH10, MC1061 (ATCC No. 53338), and CC102).

In some embodiments, the vector is introduced into a eukaryotic cell. Suitable eukaryotic cells are known in the art and include, for example, yeast cells, insect cells, and mammalian cells. Examples of suitable yeast cells include those from the genera *Kluyveromyces, Pichia*, Rhino-sporidium, *Saccharomyces*, and *Schizosaccharomyces*. Preferred yeast cells include, for example, *Saccharomyces* cerivisae and *Pichia pastoris*.

Suitable insect cells are described in, for example, Kitts et al., Biotechniques, 14: 810-817 (1993); Lucklow, *Curr. Opin. Biotechnol.*, 4: 564-572 (1993); and Lucklow et al., *J. Virol.*, 67: 4566-4579 (1993). Preferred insect cells include Sf-9 and HI5 (Invitrogen, Carlsbad, CA).

In some embodiments, mammalian cells are utilized in the invention. A number of suitable mammalian host cells are known in the art, and many are available from the American Type Culture Collection (ATCC, Manassas, VA). Examples of suitable mammalian cells include, but are not limited to, Chinese hamster ovary cells (CHO) (e.g., ATCC No. CCL61), CHO DHFR-cells (e.g., Urlaub et al., *Proc. Natl. Acad. Sci. USA*, 97: 4216-4220 (1980)), human embryonic kidney (HEK) 293 or 293T cells (e.g., ATCC No. CRL1573), and 3T3 cells (e.g., ATCC No. CCL92). Other suitable mammalian cell lines are the monkey COS-1 (e.g., ATCC No. CRL1650) and COS-7 cell lines (e.g., ATCC No. CRL1651), as well as the CV-1 cell line (e.g., ATCC No. CCL70). Further exemplary mammalian host cells include primate cell lines and rodent cell lines, including the mouse cell line NS0 a derivative of the mouse myeloma line MOPC21 (e.g. Tysabri), and transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

In some embodiments, the mammalian cell is a human cell. For example, the mammalian cell can be a human lymphoid or lymphoid derived cell line, such as a cell line of pre-B lymphocyte origin. Examples of human lymphoid cells lines include, without limitation, RAMOS (e.g., CRL-1596), Daudi (e.g., CCL-213), EB-3 (e.g., CCL-85), Raji cells (e.g., CCL-86), and derivatives thereof.

A nucleic acid sequence encoding the inventive amino acid sequence may be introduced into a cell by any suitable technique, such as by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols*, Humana Press (1991)); DEAE-dextran; electroporation; cationic liposome-mediated transfection; tungsten particle-facilitated microparticle bombardment (Johnston, *Nature*, 346: 776-777 (1990)); and strontium phosphate DNA co-precipitation (Brash et al., *Mol. Cell Biol.*, 7: 2031-2034 (1987)). Phage or viral vectors can be introduced into host cells, after growth of infectious particles in suitable packaging cells, many of which are commercially available.

The nucleic acids and cells can be used for any purpose, such as for the manufacture of the PD-1 binding agent described herein. In this respect, the invention provides a method of preparing the PD-1 binding agent comprising culturing a cell comprising a nucleic acid encoding the heavy and/or light immunoglobulin polypeptides of the PD-1 binding agent. Phrased differently, the method comprises expressing a nucleic acid encoding the immunoglobulin heavy and/or light chains of the PD-1 binding agent in a cell. It will be appreciated that the immunoglobulin heavy and light chains can be expressed from a single nucleic acid in a given cell, or the immunoglobulin heavy and light chains can be expressed from separate nucleic acids in the same cells. The method can further comprise harvesting and/or purifying the PD-1 binding agent from the cell or cell culture media using known techniques.

The following examples further illustrate the invention but, of course, should not be construed as in any way limiting its scope.

EXAMPLES

The following examples describe particular anti-PD-1 antibody heavy chain polypeptide and light chain polypeptide sequences, according to embodiments of the invention. The antibodies used in these examples are as set forth below.

437M5-112 antibodies were derived from single cell PCR on sorted PD-1 binding IgG switched B cells from an immunized mouse spleen. 3.7C6 antibodies were derived from a mouse hybridoma generated by standard fusion techniques from spleen cells of an immunized mouse. The antibodies were humanized using standard techniques described herein. The final optimized antibodies were expressed in CHO cells. The antibody sequences are summarized in Tables 1A, 1B, and 1C wherein "H" and "L" chains refer to heavy and light chains, respectively, and CDRs are as determined to include amino acids according to both Kabat and IMGT definitions (Table 1B) or according to Kabat or IMGT for certain antibodies (Tables 1C).

TABLE 1A

| AKA 437M5-112 | Expression Conditions | H Chain Variable Region | L Chain Variable Region |
|---|---|---|---|
| APE12044 | | SEQ ID NO: 30 | SEQ ID NO: 35 |
| APE11844 | | SEQ ID NO: 24 | SEQ ID NO: 34 |
| APE12043 | ExpiCHO-S ™ transient | SEQ ID NO: 29 | SEQ ID NO: 35 |
| APE12538 | CHO-S sorted stable pool | SEQ ID NO: 29 (Full H Chain SEQ ID NO: 36) | SEQ ID NO: 35 (Full L Chain SEQ ID NO: 37) |
| **AKA 3.7C6** | **Expression Conditions** | **H Chain Variable Region** | **L Chain Variable Region** |
| APE12093 | | SEQ ID NO: 46 | SEQ ID NO: 50 |
| APE12095 | ExpiCHO-S ™ transient | SEQ ID NO: 47 | SEQ ID NO: 49 |
| APE12537 | CHO-S sorted stable pool | SEQ ID NO: 47 (Full H Chain SEQ ID NO: 51) | SEQ ID NO: 49 (Full L Chain SEQ ID NO: 52) |
| APE12890 | CHO-S | SEQ ID NO: 47 (Full H Chain SEQ ID NO: 51) | SEQ ID NO: 49 (Full L Chain SEQ ID NO: 52) |

TABLE 1B

| | CDR Sequences (SEQ ID NO) | | | | | |
|---|---|---|---|---|---|---|
| Antibody | CDRH1 | CDRH2 | CDRH3 | CDRL1 | CDRL2 | CDRL3 |
| APE12044 | 15 | 2 | 21 | 23 | 5 | 6 |
| APE11844 | 13 | 2 | 19 | 22 | 5 | 6 |
| APE12043 | 15 | 2 | 20 | 23 | 5 | 6 |
| APE12538 | 15 | 2 | 20 | 23 | 5 | 6 |
| APE12093 | 57 | 41 | 9 | 10 | 11 | 12 |
| APE12095 | 57 | 42 | 9 | 10 | 11 | 12 |
| APE12537 | 57 | 42 | 9 | 10 | 11 | 12 |
| APE12890 | 57 | 42 | 9 | 10 | 11 | 12 |

TABLE 1C

| 3.7C6 (APE12095, APE12537, APE12890) | SEQ ID NO | Kabat Sequence |
|---|---|---|
| CDRH1 | 64 | DYSMH |
| CDRH2 | 65 | WINIETYYPTYADQFKG |
| CDRH3 | 66 | DYYGRFYYAMDY |
| CDRL1 | 67 | TASSSVSSSYFH |
| CDRL2 | 68 | STSNLAS |
| CDRL3 | 69 | HQYHRSPLT |

TABLE 1C-continued

| 3.7C6 (APE12095, APE12537, APE12890) | SEQ ID NO | IMGT Sequence |
|---|---|---|
| CDRH1 | 70 | NYTFTDYS |
| CDRH2 | 71 | INIETYYP |
| CDRH3 | 72 | ARDYYGRFYYAMDY |
| CDRL1 | 73 | SSVSSSY |
| CDRL2 | 74 | STS |
| CDRL3 | 75 | HQYHRSPLT |
| **437M5 (APE12043 and APE12538)** | | **Kabat Sequence** |
| CDRH1 | 76 | SYSMH |
| CDRH2 | 77 | YINPSSGFTNYIQKFRD |
| CDRH3 | 78 | DYYGRYYYVMDY |
| CDRL1 | 79 | TASSSVSSSFLH |
| CDRL2 | 80 | STSDLAS |
| CDRL3 | 81 | HQYHRSPLT |
| **437M5 (APE12043 and APE12538)** | | **IGMT Sequence** |
| CDRH1 | 82 | GYTFTSYS |
| CDRH2 | 83 | INPSSGFT |
| CDRH3 | 84 | ARDYYGRYYYVMDY |
| CDRL1 | 85 | SSVSSSF |
| CDRL2 | 86 | STS |
| CDRL3 | 87 | HQYHRSPLT |

Example 1

This example demonstrates that the antibodies disclosed herein exhibit saturation binding to human and cynomolgus monkey PD-1 expressed in stably transfected HEK 293 cells.

Figure 1:
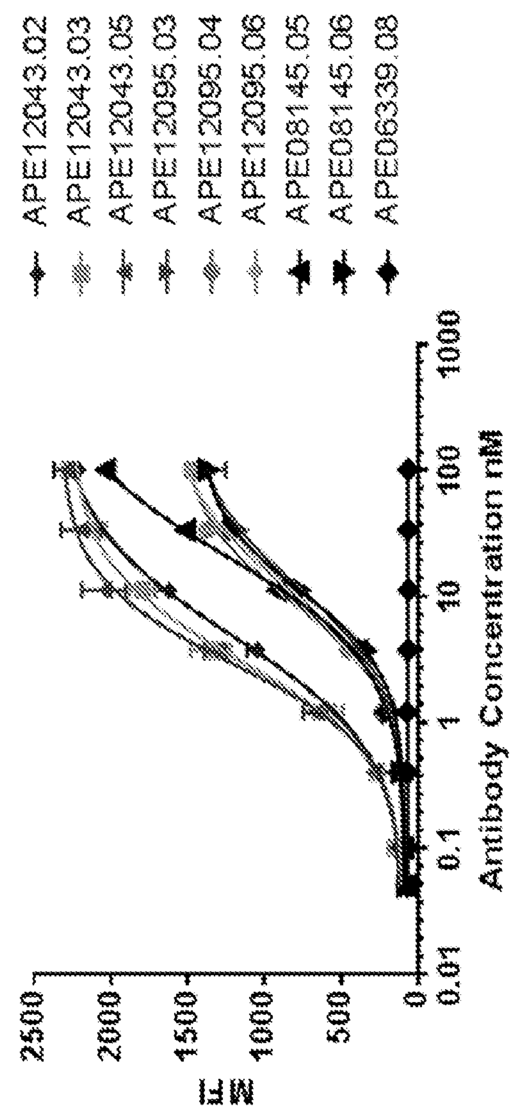
FIG. 1 is a graph depicting the results of binding of anti-PD-1 antibodies to HEK 293 cells stably transfected with human PD-1.
Figure 2:
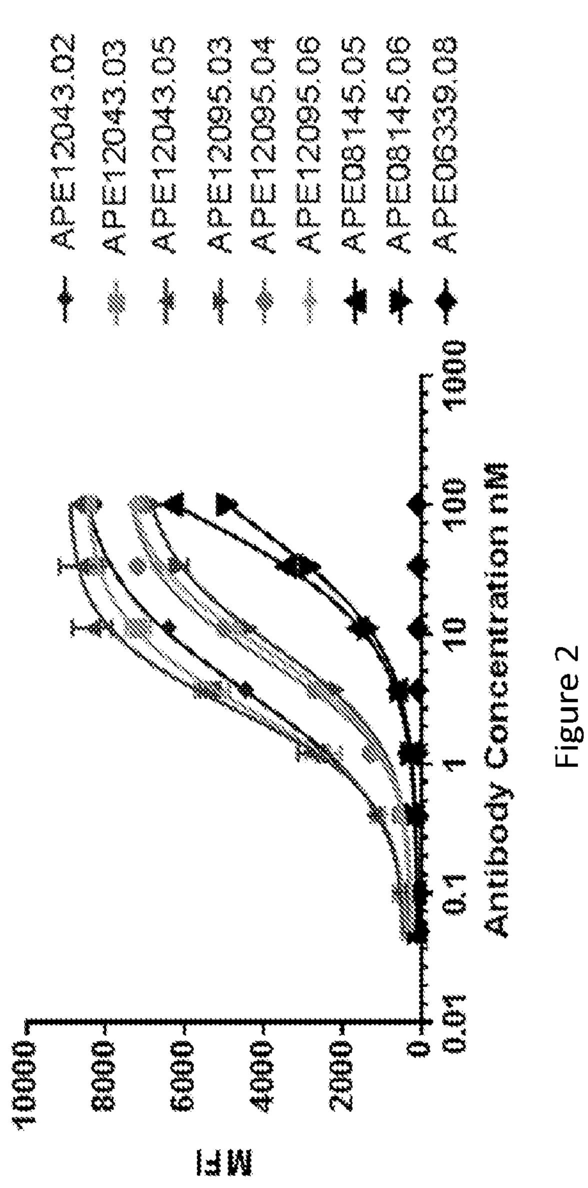
FIG. 2 is a graph depicting the results of binding of anti-PD-1 antibodies to HEK 293 cells stably transfected with cynomolgus monkey PD-1.

HEK 293 cells were stably transfected to express either human PD-1 or cynomolgus monkey PD-1. Cells were harvested by Accutase™ treatment (Innovative Cell Technologies, San Diego, CA), the cells expressing cynomolgus monkey PD-1 were treated with the lipophilic fluorescent dye Vybrant® DiD (ThermoFisher Scientific, Carlsbad, CA), and then mixed with an equal number of unlabeled HEK 293 cells expressing human PD-1. Cells ($2\times10^5$ total per sample) were stained with the indicated concentrations of each antibody for 40 min at 4° C. with gentle shaking, centrifuged and washed once. Cells were fixed in 2% paraformaldehyde in phosphate-buffered saline (PBS) for 10 min at room temperature, washed, and antibodies detected with Phycoerythrin (PE)-conjugated goat anti-human kappa (Southern Biotechnology, Birmingham, AL) for 15 min at 4° C. with gentle shaking. Cells were washed, resuspended, and bound antibody fluorescence quantified on a BD FACSArray™ (BD Biosciences, San Jose, CA). Data were analyzed for median fluorescence intensity (MFI) using FlowJo® analysis software (FlowJo, LLC). ECso values were determined in GraphPad Prism 5.0 (GraphPad Software) using a log(agonist) vs. response—Variable slope (4 parameters) curve fit. The results are shown in FIGS. 1 and 2, and the ECso values are set forth in Table 2 (human) and Table 3 (cynomolgus monkey). APE06339 is a human IgG1 isotype control antibody specific for hen egg lysozyme. APE08145 is a reference anti-PD-iantibody.

TABLE 2

| Antibody | Type | $EC_{50}$ (nM) |
|---|---|---|
| APE12043.02 | 437M5-112 | 4.88 |
| APE12043.03 | 437M5-112 | 3.13 |
| APE12043.05 | 437M5-112 | 2.95 |
| APE12095.03 | 3.7C6 | 11.92 |
| APE12095.04 | 3.7C6 | 9.04 |
| APE12095.06 | 3.7C6 | 11.82 |
| APE08145.05 | Reference Anti-PD1 | 20.80 |
| APE08145.06 | Reference Anti-PD1 | 10.91 |
| APE06339.08 | IgG1 Isotype Control | No binding |

TABLE 3

| Antibody | Type | $EC_{50}$ (nM) |
|---|---|---|
| APE12043.02 | 437M5-112 | 3.69 |
| APE12043.03 | 437M5-112 | 2.69 |
| APE12043.05 | 437M5-112 | 2.59 |
| APE12095.03 | 3.7C6 | 7.99 |
| APE12095.04 | 3.7C6 | 6.17 |
| APE12095.06 | 3.7C6 | 7.47 |
| APE08145.05 | Reference Anti-PD1 | 91.14 |
| APE08145.06 | Reference Anti-PD1 | 65.68 |
| APE06339.08 | IgG1 Isotype Control | No binding |

Example 2

This example demonstrates that the antibodies disclosed herein bind to 2-day anti-CD3/anti-CD28 activated human peripheral blood $CD4^+$ T cells.

Figure 3:
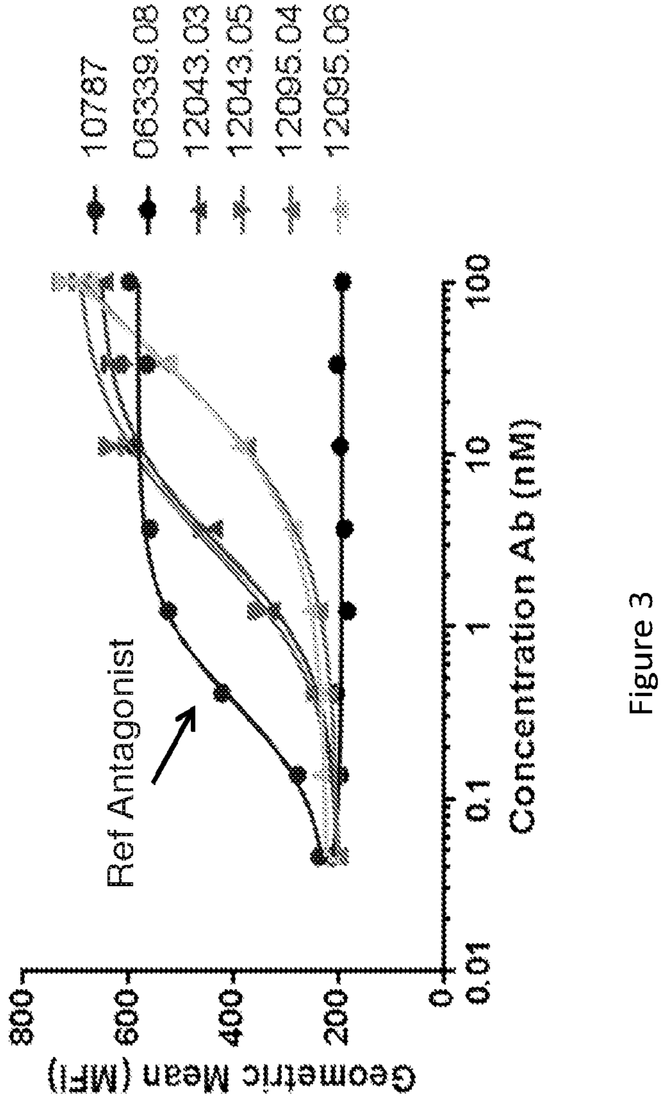
FIG. 3 is a graph depicting the results of binding of anti-PD-1 antibodies to 2-day anti-CD3/anti-CD28 activated human peripheral blood $CD4^+$ T cells.

Primary human peripheral blood $CD4^+$ T cells were prepared using magnetic bead separation ($CD4^+$ T Cell Isolation Kit, Miltenyi Biotec, Auburn, CA) of peripheral blood mononuclear cells (PBMCs) and activated for 48 hours with plastic-coated anti-CD3 and anti-CD28 in 6-well plates. Cells ($1\times10^5$ per sample) were washed and stained in V-bottom 96-well plates with the indicated concentrations of each antibody for 30 min at 4° C. with gentle shaking, centrifuged and washed once. Cells were fixed in 4% paraformaldehyde in PBS for 10 min at room temperature, washed, and antibodies detected with Alexa Fluor 647-conjugated F(ab')2 goat anti-human IgG Fc (Jackson ImmunoResearch, West Grove, PA) for 10 min at 4° C. Cells were washed, resuspended, and bound antibody fluorescence quantified on a BD FACSArray™ (BD Biosciences, San Jose, CA). Data were analyzed for geometric mean fluorescence intensity (MFI) using FlowJo® analysis software (FlowJo, LLC). ECso values were determined in GraphPad Prism 7.02 (GraphPad Software) using a log(agonist) vs. response—Variable slope (4 parameters) curve fit. The results are shown in FIG. 3, and the $EC_{50}$ values are set forth in Table 4. APE10787 is a human IgG1 positive control antibody specific for PD-1, and APE06339 is a human IgG1 isotype control antibody specific for hen egg lysozyme.

TABLE 4

| Antibody | Description | $EC_{50}$ (nM) |
|---|---|---|
| APE10787 | Anti-PD-1 Positive Control | 0.36 |
| APE06339.08 | IgG1 Isotype Control | No binding |
| APE12043.03 | 437M5-112 | 2.99 |
| APE12043.05 | 437M5-112 | 3.06 |
| APE12095.04 | 3.7C6 | 39.07 |
| APE12095.06 | 3.7C6 | 53.87 |

Example 3

This example documents the degree to which the antibodies disclosed herein compete with PD-L1 and PD-L2 for binding to human PD-1 transfected CHO-K1 cells.

Competition assays were performed to test competition for PD-1 binding between anti-PD-1 antibodies and PD-L1-Fc or PD-L2-Fc constructs. As shown in FIGS. 4-7, the tested antibody shows moderate competition with PD-L1 (~70% maximum inhibition) and strong competition with PD-L2; Another tested antibody shows weak/minimal competition with PD-L1 (~15% maximum inhibition) and moderate competition with PD-L2 (~70% maximum inhibition).

Figure 4:
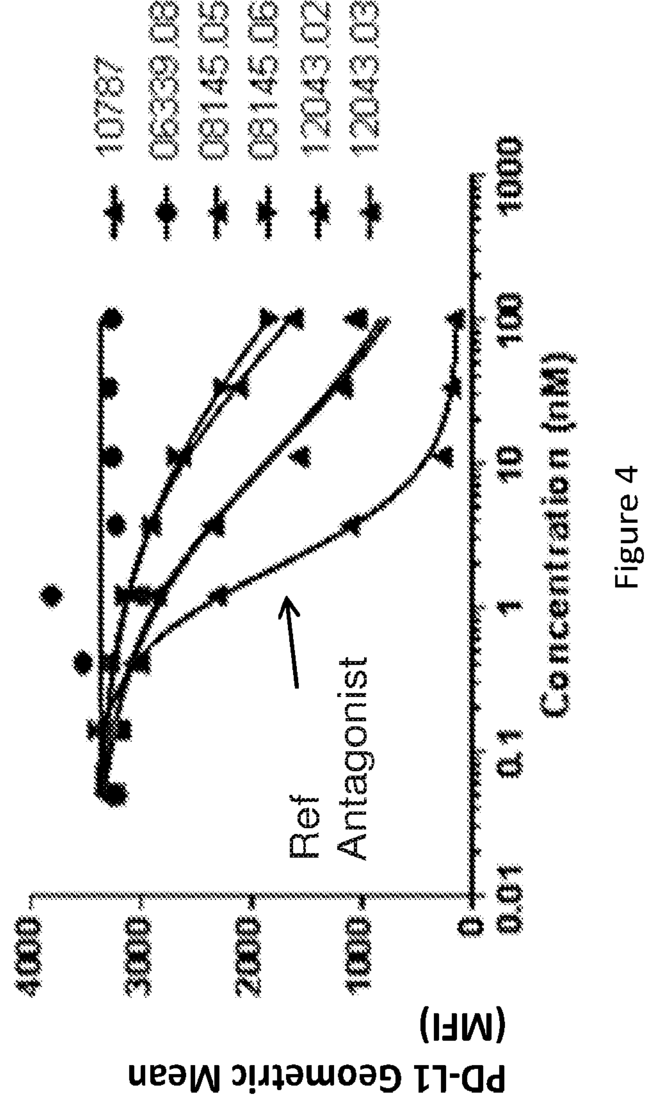
FIGS. 4-7 are graphs showing testing results of anti-PD-1 antibodies competing with either PD-L1-Fc or PD-L2-Fc for binding to PD-1 CHO-K1 cells.
Figure 5:
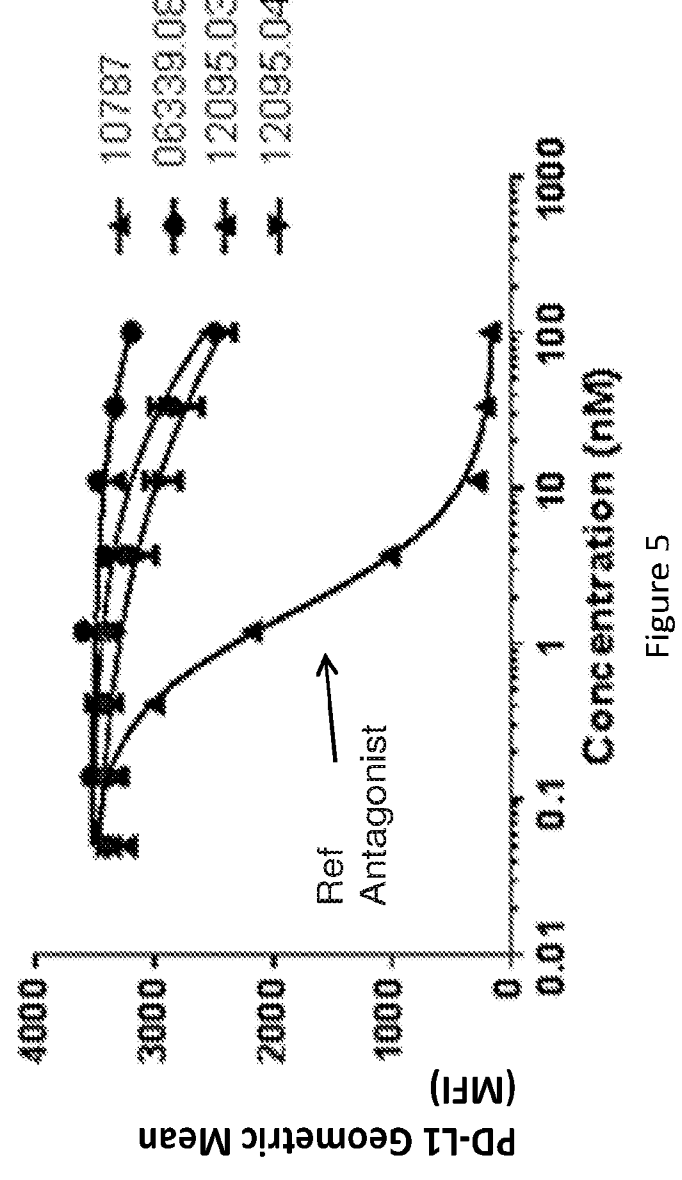

CHO-K1 cells were stably transfected to express human PD-1 and a high level expressing clone was selected. Cells were harvested by Accutase™ treatment (Innovative Cell Technologies, San Diego, CA), and placed in U-bottom 96-well plates ($2\times10^5$ cells/well). For testing PD-L1 competition antibodies were serially diluted and pre-mixed with DyLight 650 (DyL650)-labeled human PD-L1-mouse IgG1 Fc fusion protein (Abcam, Cambridge, MA.) (10 nM final concentration DyL650-PD-L1-Fc and antibody concentrations as indicated in FIGS. 4 and 5). After incubation for 10 min on ice the antibody/DyL650-PD-L1-Fc mixtures were added to the cells for 30 min at 4° C. with gentle shaking. Cells were centrifuged, washed once, resuspended in buffer containing propidium iodide, and bound PD-L1-Fc fluorescence quantified on a BD FACSArray™ (BD Biosciences, San Jose, CA). Data were analyzed for PD-L1 geometric median fluorescence intensity (MFI) using FlowJo® analysis software (FlowJo, LLC). $IC_{50}$ values were determined in GraphPad Prism 7.02 (GraphPad Software) using a log (agonist) vs. response—Variable slope (4 parameters) curve fit. The results are shown in FIGS. 4 and 5, and the resulting $IC_{50}$ values are set forth in Tables 4-5. APE10787 ("10787") is a human IgG1 positive control antagonist antibody specific for PD-1, and APE06339 ("06339.08") is a human IgG1 isotype control antibody specific for hen egg lysozyme. APE08145 ("08145.05" and "08145.06") is a reference antibody. APE12043 ("12043.02" and "12043.03") is the 437M5-112 anti-PD-1 antibody described in Example 1. APE12095 ("12095.03" and "12095.04") is the 3.7C6 anti-PD-1 antibody described in Example 1.

Figure 6:
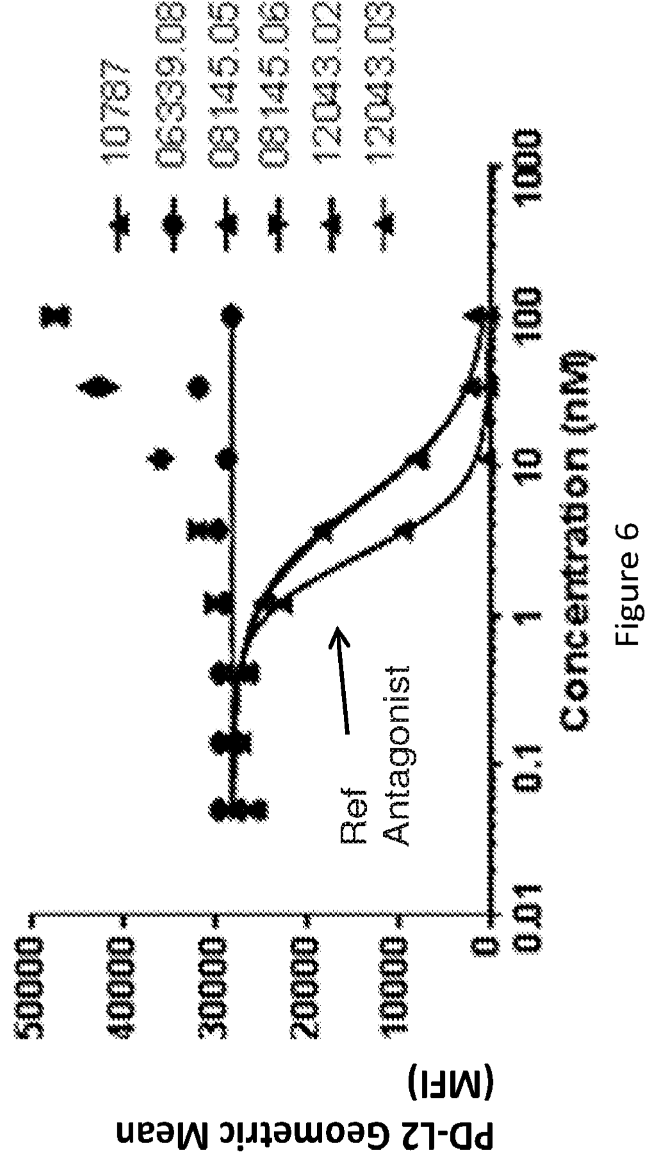
Figure 7:
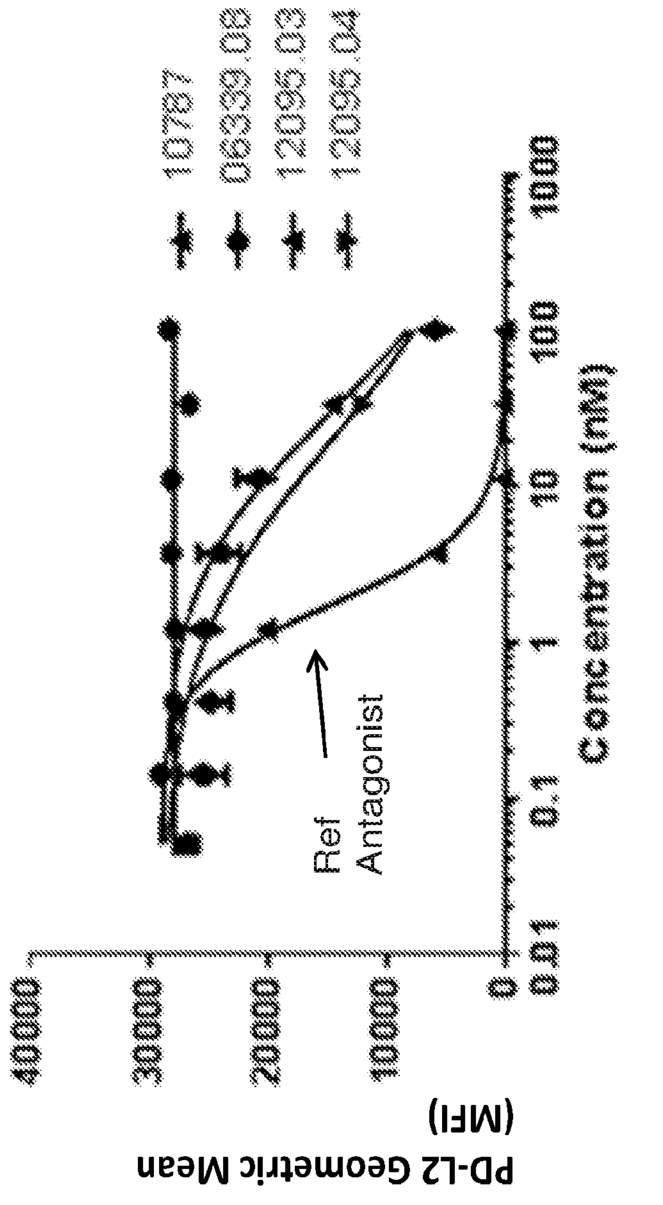

A CHO-K1 cell clone stably expressing high levels of human PD-1 was harvested by Accutase™ treatment (Innovative Cell Technologies, San Diego, CA), and placed in U-bottom 96-well plates ($2\times10^5$ cells/well). For testing PD-L2 competition antibodies were serially diluted and pre-mixed with DyL650-labeled human PD-L2-mouse IgG1 Fc fusion protein (Abcam, Cambridge, MA) (10 nM final concentration DyL650-PD-L2-Fc and antibody concentrations as indicated in FIGS. 6 and 7). After incubation for 10 min on ice the antibody/DyL650-PD-L2-Fc mixtures were added to the cells for 30 min at 4° C. with gentle shaking. Cells were centrifuged, washed once, resuspended in buffer containing propidium iodide, and bound PD-L2-Fc fluorescence quantified on a BD FACSArray™ (BD Biosciences, San Jose, CA). Data were analyzed for PD-L2 geometric median fluorescence intensity (MFI) using FlowJo® analysis software (FlowJo, LLC). $IC_{50}$ values were determined in GraphPad Prism 7.02 (GraphPad Software) using a log (agonist) vs. response—Variable slope (4 parameters) curve fit. The results are shown in FIGS. 6 and 7, and the resulting $IC_{50}$ values are set forth in Tables 6-7. APE10787 ("10787") is a human IgG1 positive control antagonist antibody specific for PD-1, and APE06339 ("06339.08") is a human IgG1 isotype control antibody specific for hen egg lysozyme. APE08145 ("08145.05" and "08145.06") is a reference antibody. APE12043 ("12043.02" and "12043.03") is the 437M5-112 anti-PD-1 antibody described in Example 1. APE12095 ("12095.03" and "12095.04") is the 3.7C6 anti-PD-1 antibody described in Example 1.

TABLE 4

| PD-L1-Fc Competition | | |
|---|---|---|
| Antibody | Type | $IC_{50}$ (nM) |
| APE10787 | Anti-PD-1 Positive Control | 1.89 |
| APE06339.08 | IgG1 Isotype Control | No competition |
| APE08145.05 | Reference Anti-PD-1 | 75.2 |
| APE08145.06 | Reference Anti-PD-1 | 119.1 |
| APE12043.02 | 437M5-11 | 11.6 |
| APE12043.03 | 437M5-11 | 12.2 |

TABLE 5

| PD-L1-Fc Competition | | |
|---|---|---|
| Antibody | Type | $IC_{50}$ (nM) |
| APE10787 | Anti-PD-1 Positive Control | 1.59 |
| APE06339.08 | IgG1 Isotype Control | No competition |
| APE12095.03 | 3.7C6 | 495.1 |
| APE12095.04 | 3.7C6 | 632.1 |

TABLE 6

| PD-L2-Fc Competition | | |
|---|---|---|
| Antibody | Type | $IC_{50}$ (nM) |
| APE10787 | Anti-PD-1 Positive Control | 2.53 |
| APE06339.08 | IgG1 Isotype Control | No competition |
| APE08145.05 | Reference Anti-PD-1 | No competition |
| APE08145.06 | Reference Anti-PD-1 | No competition |
| APE12043.02 | M5-11 | 5.8 |
| APE12043.03 | M5-11 | 5.5 |

TABLE 7

| PD-L2-Fc Competition | | |
|---|---|---|
| Antibody | Type | $IC_{50}$ (nM) |
| APE10787 | Anti-PD-1 Positive Control | 1.78 |
| APE06339.08 | IgG1 Isotype Control | No competition |
| APE12095.03 | 3.7C6 | 30.4 |
| APE12095.04 | 3.7C6 | 20.0 |

Example 4

This example demonstrates that the antibodies disclosed herein show consistent agonist activity in bead-based and plate-based agonist assays.

Figures 8A, 8B:
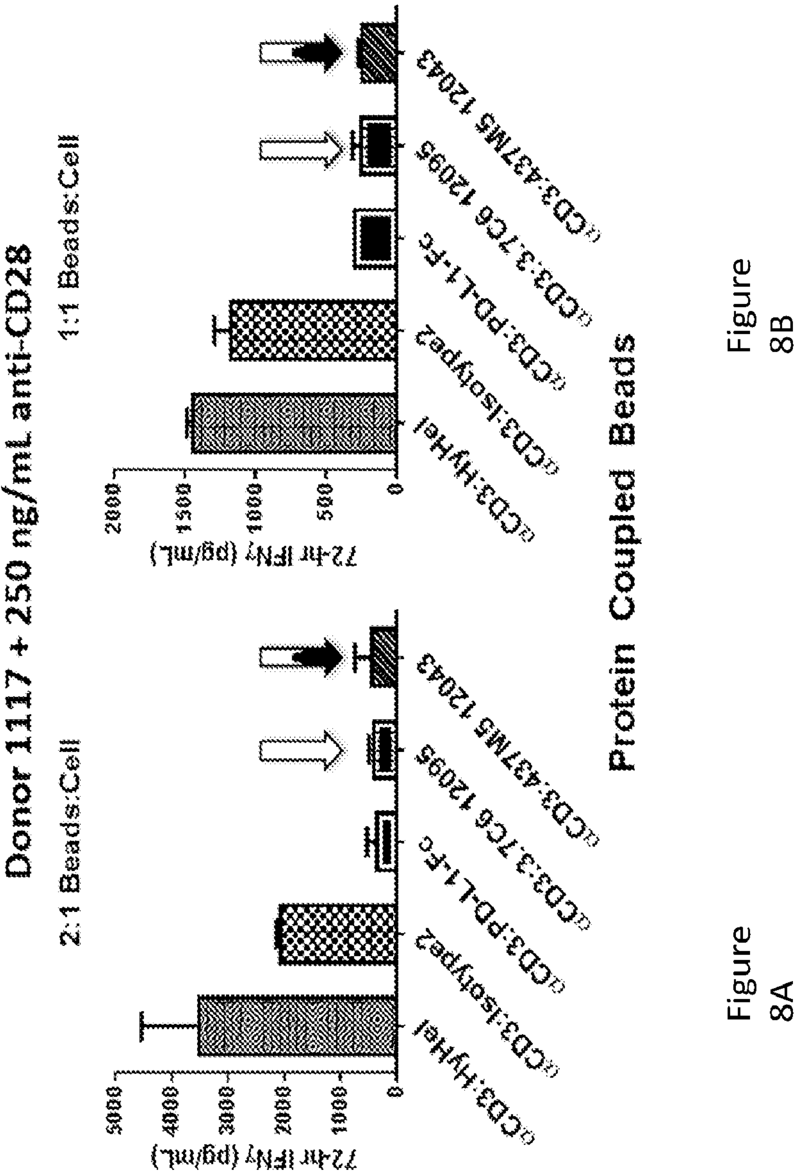
FIG. 8A is a graph depicting the agonist activity performance of anti-PD-1 antibodies in a bead-based $CD4^+$ T cell agonist assay using a 2:1 bead to cell ratio.
FIG. 8B is a graph depicting the agonist activity performance of anti-PD-1 antibodies in a bead-based $CD4^+$ T cell agonist assay using a 1:1 bead to cell ratio.

For bead-based agonist assays Dynabeads® M-280 Tosylactivated (Invitrogen—Life Technologies, Carlsbad, CA) were coupled according to the manufacturer's instructions with anti-CD3 (10 μg), anti-PD-1 or PD-L1-Fc (40 μg), and a negative control antibody binding hen egg lysozyme (50 μg) for a total of 100 μg protein coupled. Extent of bead coupling was quantified by flow cytometry. Primary human peripheral blood $CD4^+$ T cells were prepared using magnetic bead separation ($CD4^+$ T Cell Isolation Kit, Miltenyi Biotec, Auburn, CA) of PBMCs. Purified $CD4^+$ T cells ($1\times10^5$ cells/well) were incubated with different numbers of beads as indicated, (4:1, 2:1, or 1:1 ratios of beads:T cells) in the presence of soluble anti-CD28 (eBioscience; 250 ng/ml, 100 ng/ml or 50 ng/ml as indicated) for 72 hours. Secreted IFNγ in culture supernatants was quantified by ELISA (R&D Systems, Minneapolis, MN). As shown in FIGS. 8A and 8B, and summarized in Table 8, the anti-PD-1 antibodies disclosed herein (437M5-112 and 3.7C6) demonstrated consistent inhibitory (agonist) activity in the bead assay that was comparable to PD-L1-Fc.

Figures 9A, 9B, 9C:
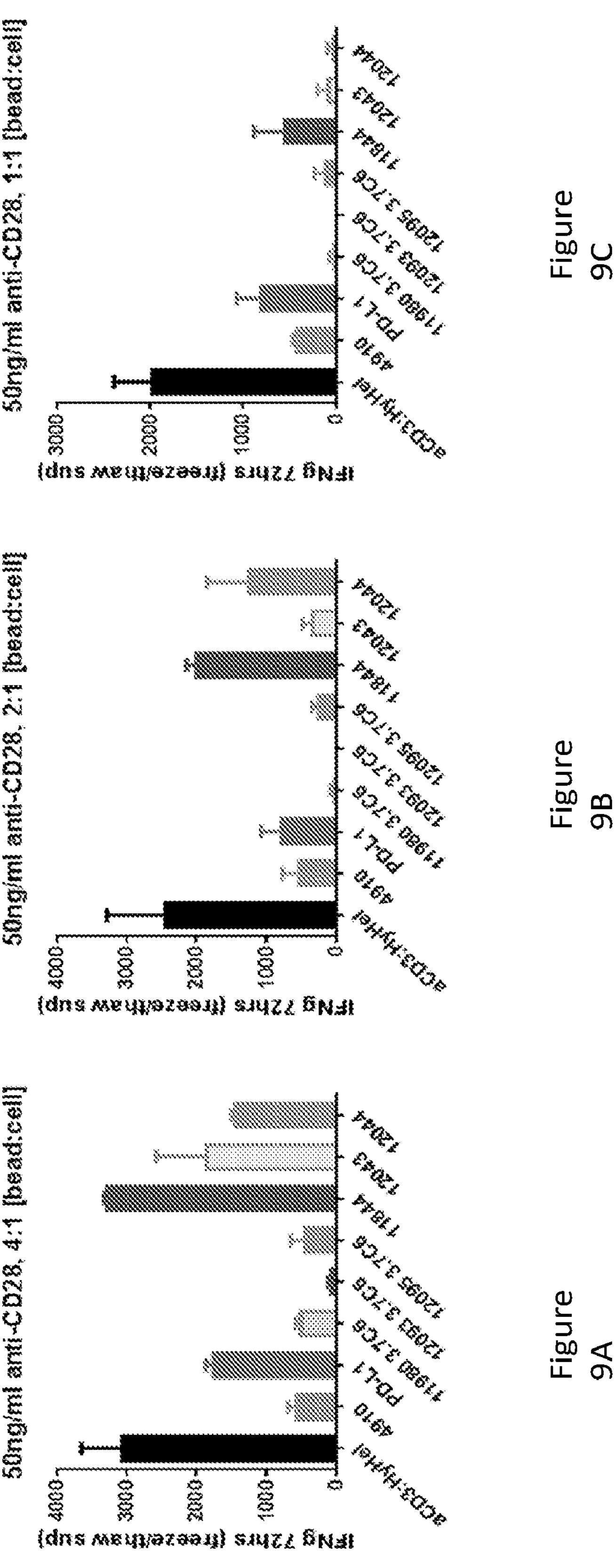
FIG. 9A is a graph depicting the agonist activity performance of anti-PD-1 antibodies in a bead-based $CD4^+$ T cell agonist assay using a 4:1 bead to cell ratio.
FIG. 9B is a graph depicting the agonist activity performance of anti-PD-1 antibodies in a bead-based $CD4^+$ T cell agonist assay using a 2:1 bead to cell ratio.
FIG. 9C is a graph depicting the agonist activity performance of anti-PD-1 antibodies in a bead-based $CD4^+$ T cell agonist assay using a 1:1 bead to cell ratio.
Figure 10A:
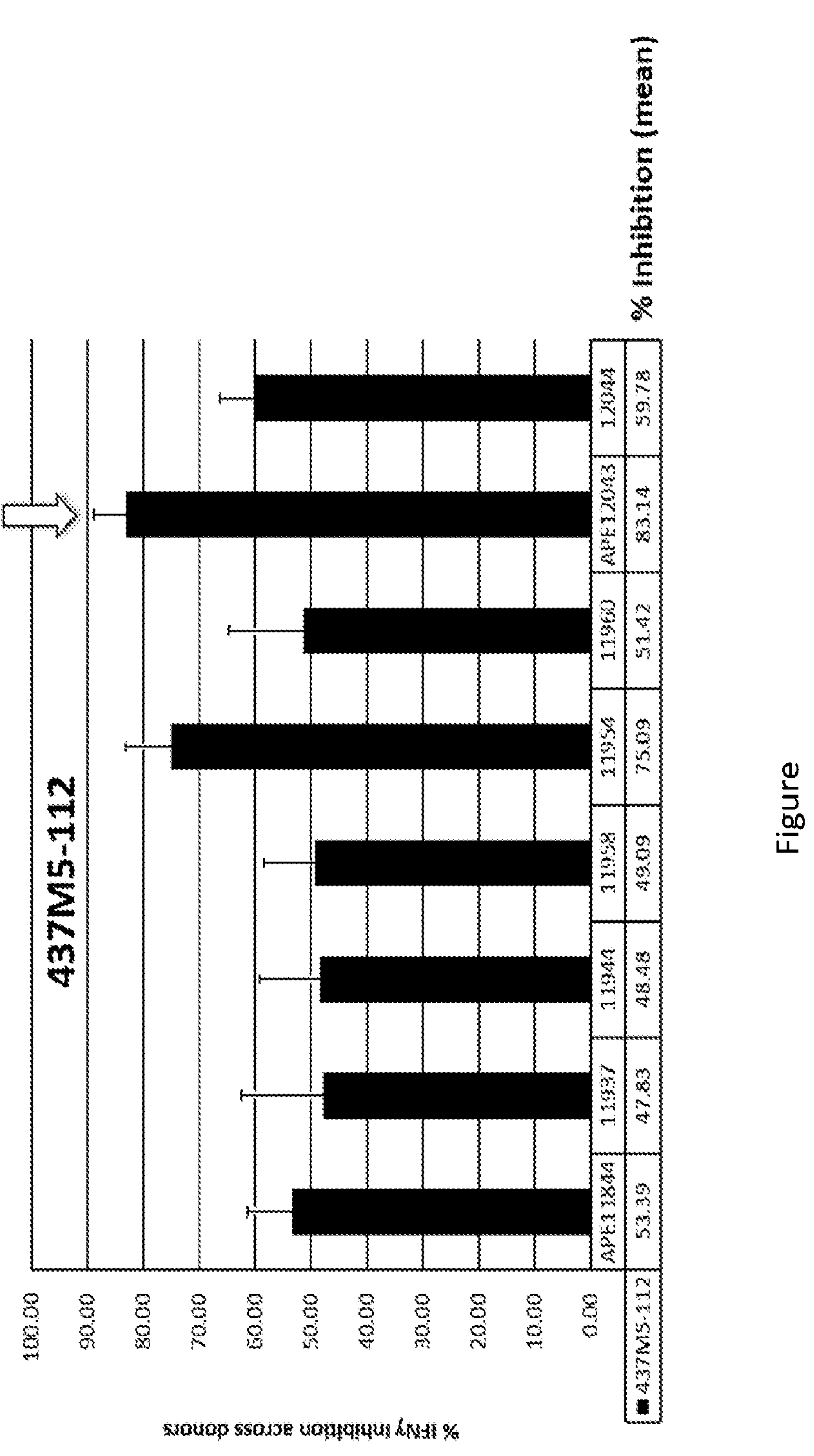
FIG. 10A is a graph depicting the mean % inhibition of IFNγ production across multiple donors in a bead-based $CD4^+$ T cell agonist assay for an anti-PD-1 antibody.
Figure 11B:
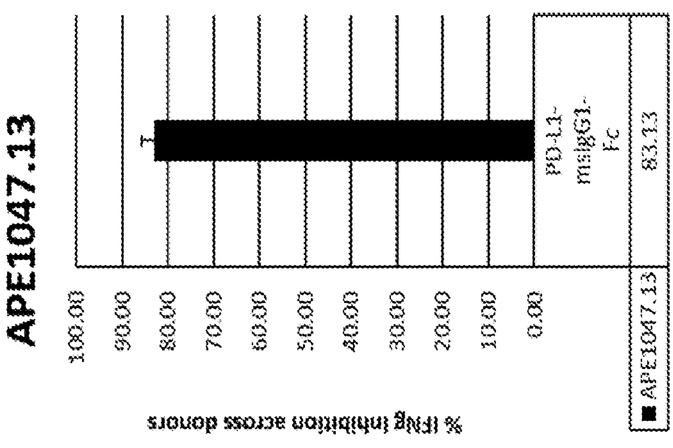
FIG. 11B is a graph depicting the mean % inhibition of IFNγ production across the same donors in a bead-based $CD4^+$ T cell agonist assay for a reference PD-1 agonist, PD-L1-Fc.
Figure 11A:
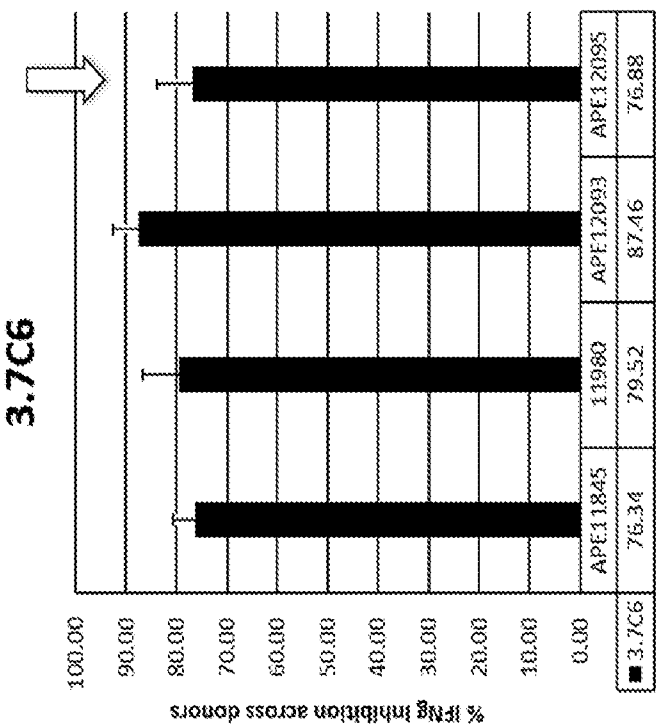
FIG. 11A is a graph depicting the mean % inhibition of IFNγ production across multiple donors in a bead-based $CD4^+$ T cell agonist assay for an anti-PD-1 antibody.

As shown in FIGS. 9A-9C, the 3.7C6 variants APE12093 and APE12095 were the best agonists in the bead-based assay, with stronger inhibition as compared with the PD-L1-Fc. The 437M5-112 variants APE12043 and APE12044 had improved agonist activity compared to the parent antibody APE11844.

TABLE 8

| Candidate Antibody | Number of donors tested | % Inhibition of IFNγ (Mean ± SEM) |
|---|---|---|
| 437M5-112 (APE12043) | 7 | 83 ± 6 |
| 3.7C6 (APE12095) | 6 | 77 ± 7 |
| PD-L1-Fc | 10 | 83 ± 3 |

Inhibition of IFNγ production by the anti-PD-1 antibodies disclosed herein across donors tested in the bead-based agonist assay is shown in FIGS. 10A-10B and FIGS. 11A-11C.

Figure 12A:
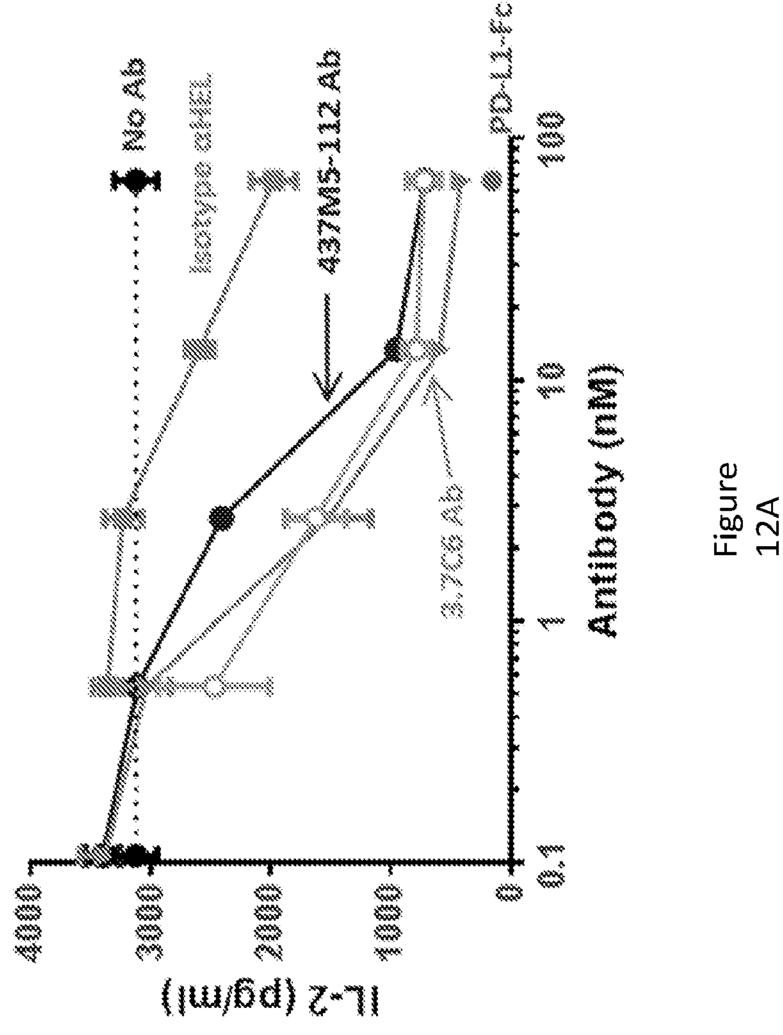
FIG. 12A is a graph depicting the agonist potency of anti-PD-1 antibodies in inhibiting IL-2 production in a plate-based human PBMC agonist assay (donor #747).
Figure 12B:
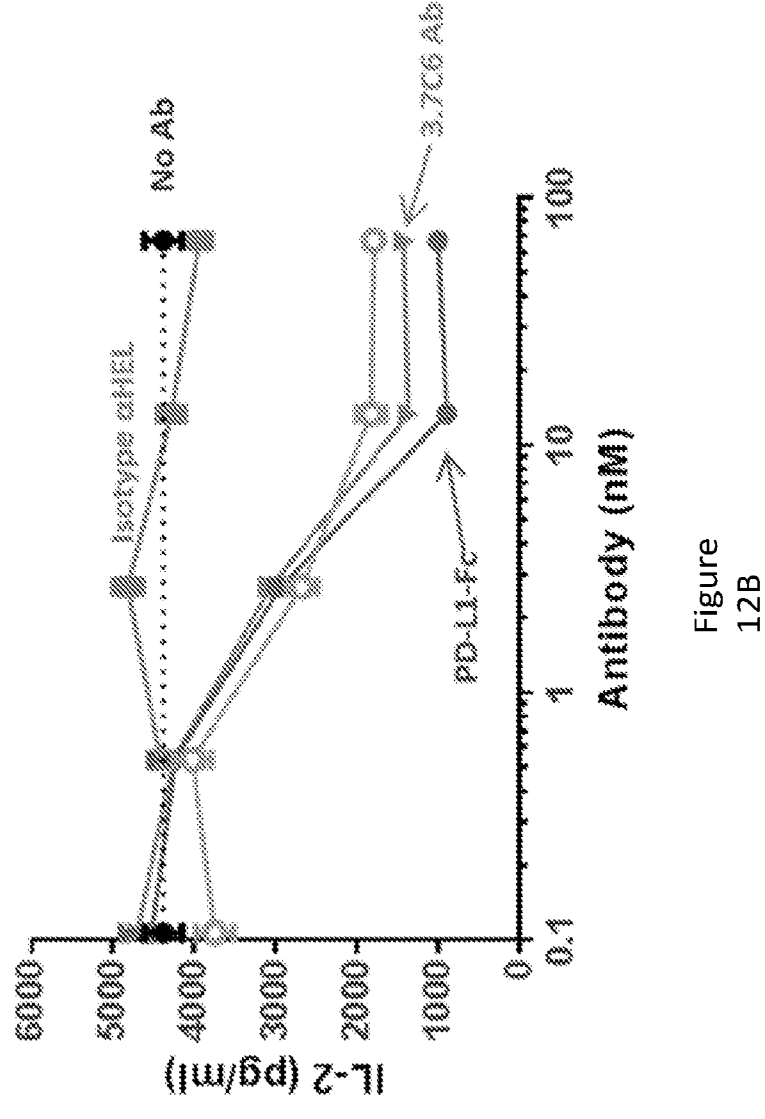
FIG. 12B is a graph depicting the agonist potency of an anti-PD-1 antibody and PD-L1-Fc in inhibiting IL-2 production in a plate-based human PBMC agonist assay (donor #500).
Figure 13A:
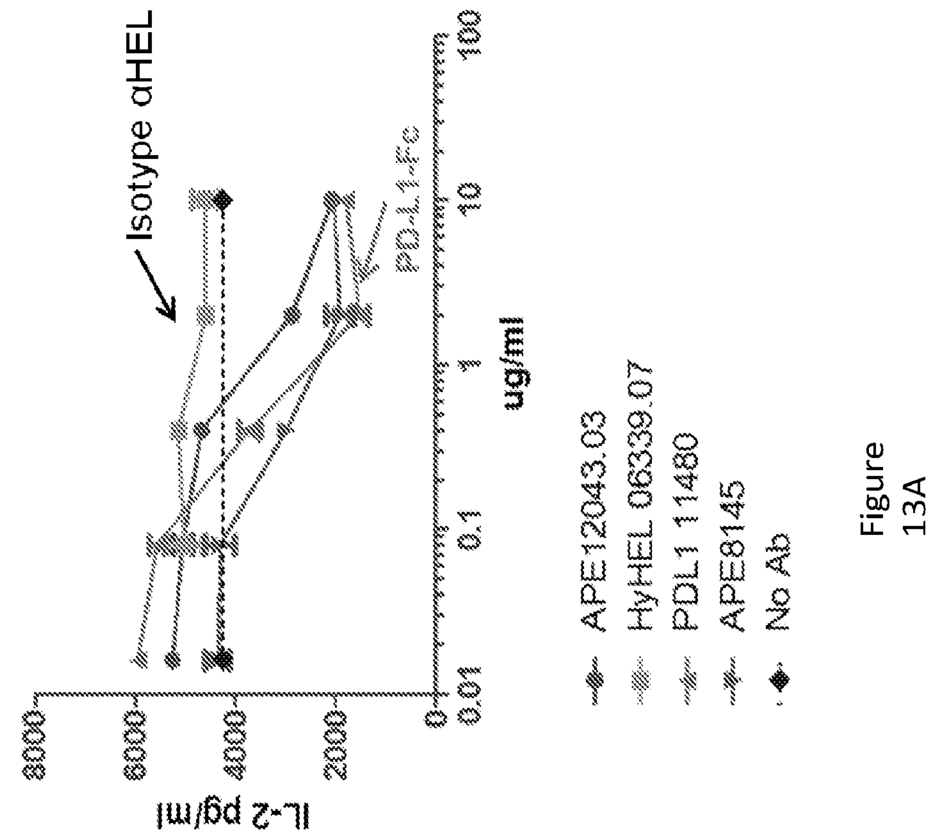
FIG. 13A is a graph depicting the agonist potency of an anti-PD-1 antibody and PD-L1-Fc in inhibiting IL-2 production in a plate-based human PBMC agonist assay (frozen donor #500).
Figure 13B:
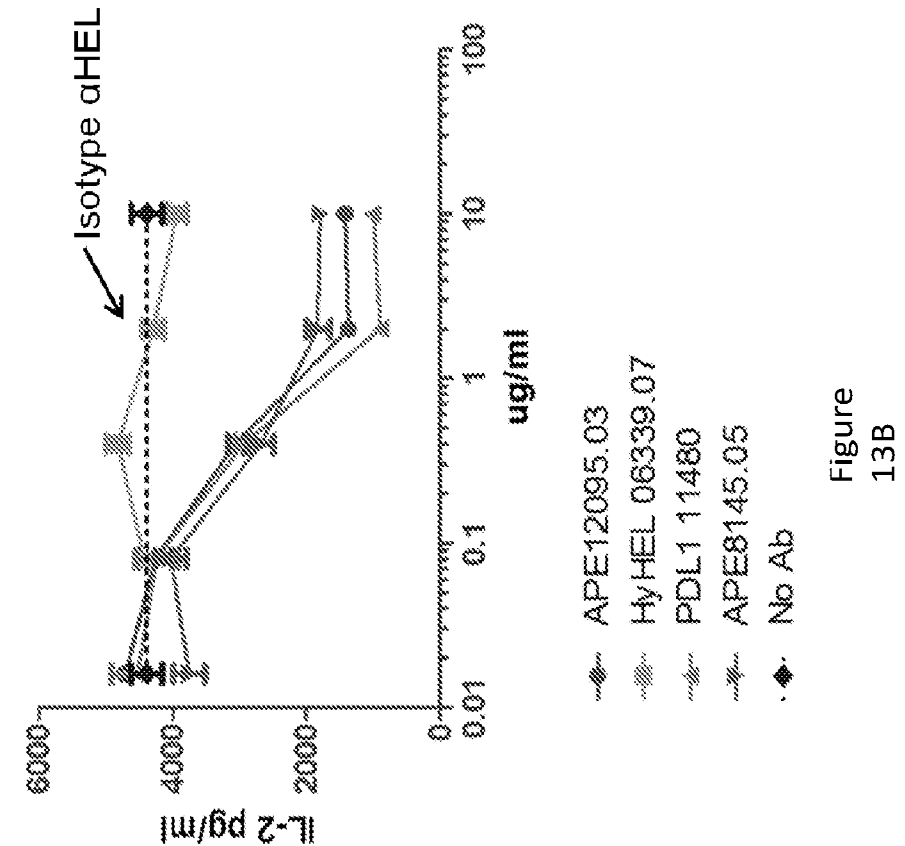
FIG. 13B is a graph depicting the agonist potency of an anti-PD-1 antibody and PD-L1-Fc in inhibiting IL-2 production in a plate-based human PBMC agonist assay (frozen donor #500).
Figure 14A:
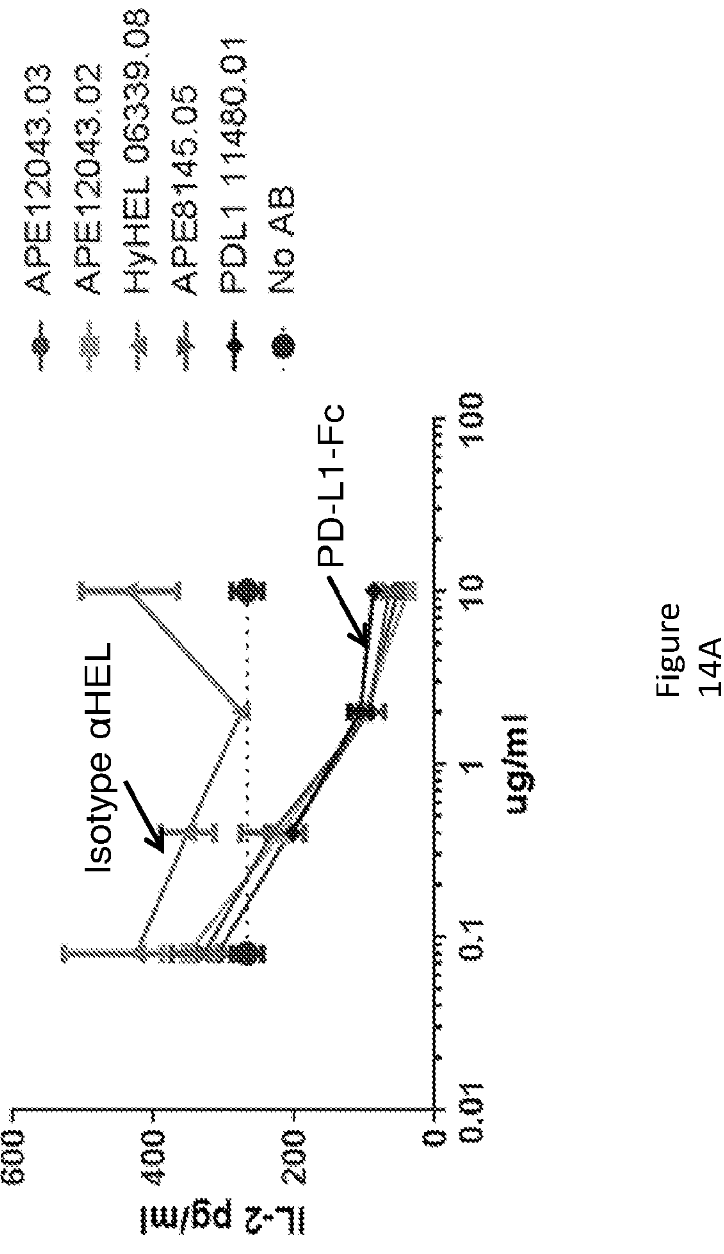
FIG. 14A is a graph depicting the agonist potency of an anti-PD-1 antibody and PD-L1-Fc in inhibiting IL-2 production in a plate-based human PBMC agonist assay (frozen donor #1202).
Figure 14B:
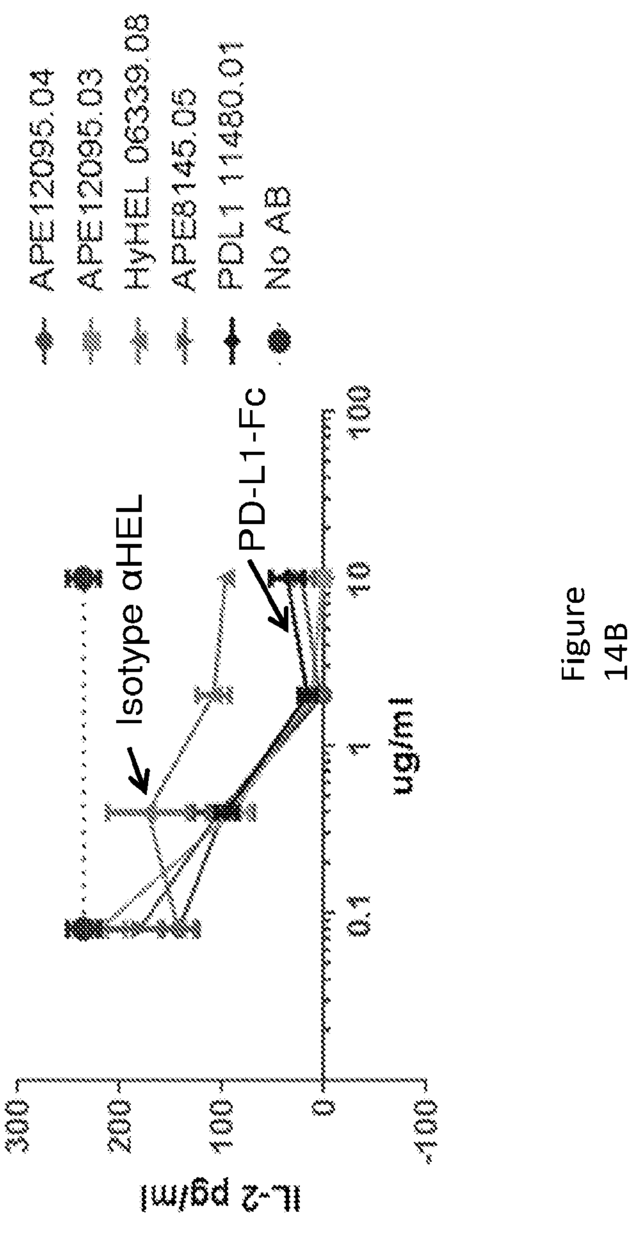
FIG. 14B is a graph depicting the agonist potency of an anti-PD-1 antibody and PD-L1-Fc in inhibiting IL-2 production in a plate-based human PBMC agonist assay (frozen donor #1202).

For plate-based agonist assays 96-well plates were sequentially coated with anti-CD3 (0.3 μg/ml) overnight at 4° C., wells aspirated and washed with PBS, and then subjected to a second coating overnight at 4° C. with various concentrations of anti-PD-1 antibody or PD-L1-Fc as indicated in FIGS. 12-14. Fresh or frozen human PBMCs were cultured in the presence of phytohemagglutinin (PHA; 2 μg/ml) for 48 hours, harvested, washed to remove PHA, and cultured overnight in the presence of IL-2. Cells were harvested, washed and incubated in the anti-CD3/anti-PD-1 coated wells ($1\times10^5$ cells/well) in the presence of human gamma globulin (100 μg/ml) for 48 hours. Secreted IL-2 in culture supernatants was quantified by ELISA (R&D Systems, Minneapolis, MN). Inhibition of IL-2 production by the PD-1 antibodies across three PBMC donors is shown in FIGS. 12A-12B, 13A-13B, and 14A-14B. Inhibition of IL-2 production by the anti-PD-1 antibodies disclosed herein was comparable to that induced by PD-L1-Fc.

Example 5

This example demonstrates that the anti-PD-1 antibodies disclosed herein displayed agonist antibody activity in solution in the presence of blocking anti-PD-L1/anti-PD-L2.

Figure 15A:
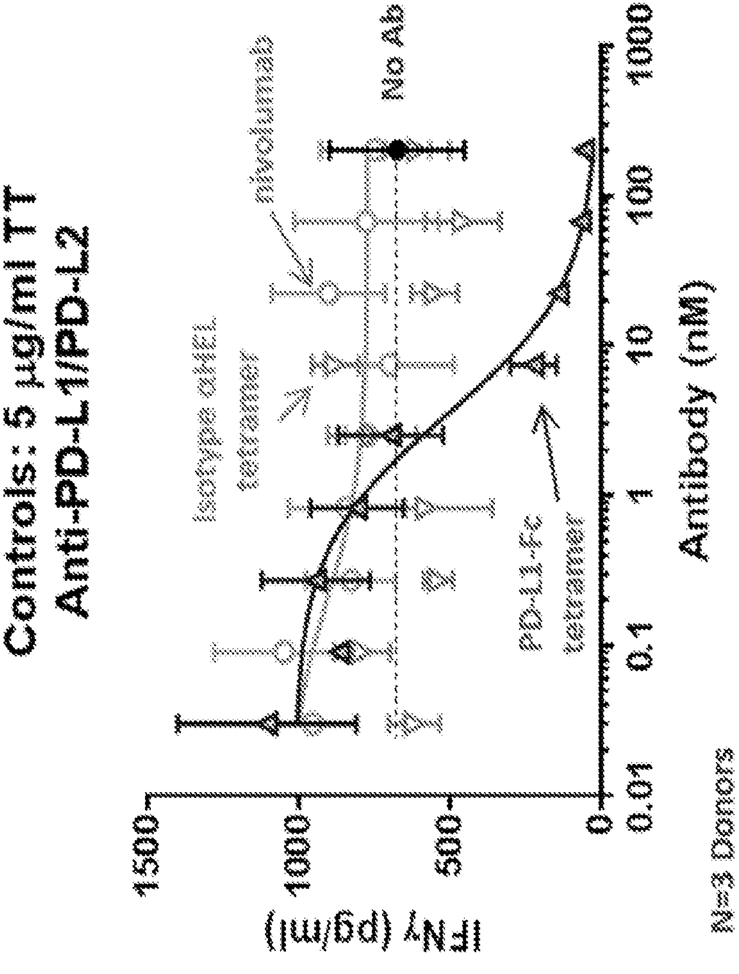
FIG. 15A is a graph depicting the observed agonist activity of a PD-L1-Fc tetramer in a whole human blood tetanus recall assay and lack of agonist activity of nivolumab in the presence of blocking anti-PD-L1/anti-PD-L2.
Figure 15B:
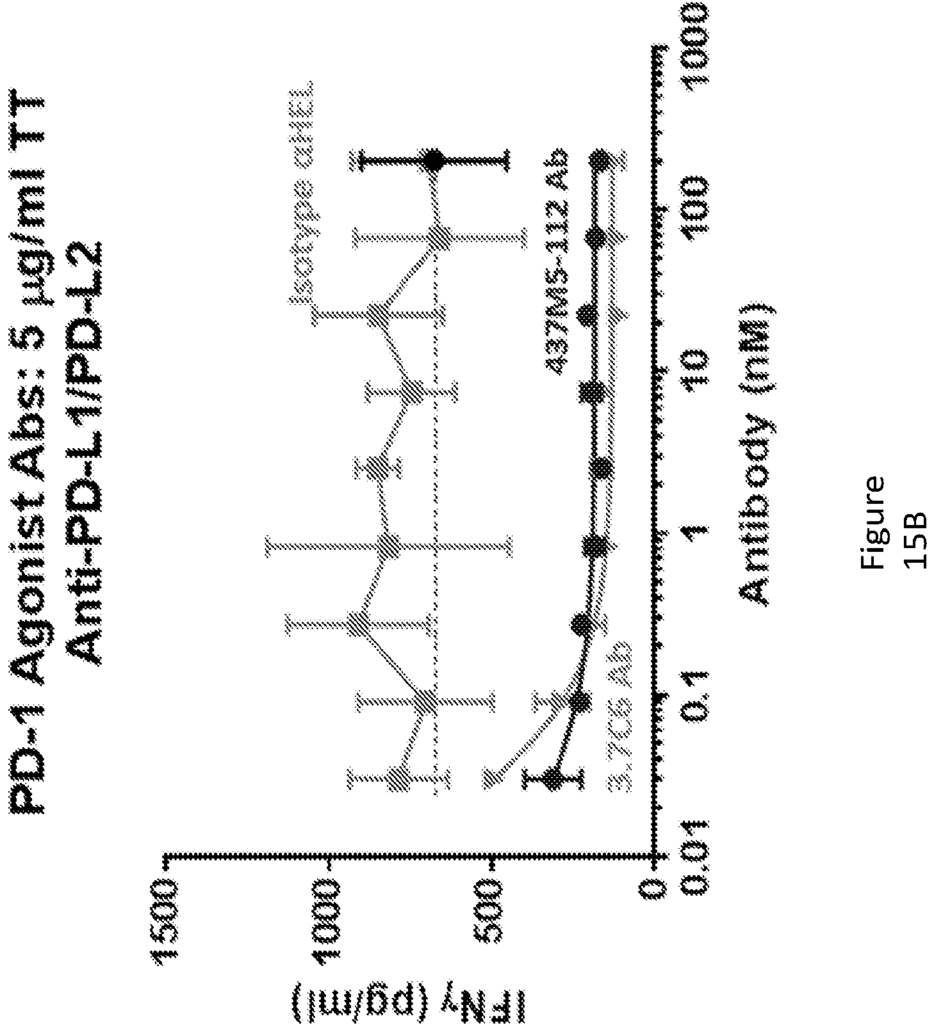
FIG. 15B is a graph depicting the observed agonist activity of PD-1 agonist antibodies in a whole human blood tetanus recall assay in the presence of blocking anti-PD-L1/anti-PD-L2.

Whole blood from tetanus toxoid immunized donors was diluted 1:3 and cultured for 4 days in U-bottom 96-well plates in the presence of tetanus toxoid (Astarte Biologics, Bothell, WA; 5 μg/ml), anti-PD-L1+anti-PD-L2 (BioLegend, San Diego, CA; 2 μg/ml each), and the indicated concentrations of tetramer PD-L1-Fc, anti-PD-1 IgG1 antibodies described herein (3.7C6 APE12095; 437M5-112 APE12043), or control human IgG1. Secreted IFNγ in culture supernatants was quantified by ELISA (R&D Systems, Minneapolis, Minn.). In this tetanus toxoid recall response whole blood assay, potent agonist antibody activity of the anti-PD-1 antibodies described herein was observed in the presence of blocking anti-PD-L1/anti-PD-L2, as shown in FIGS. 15A (positive and negative controls) and 15B (anti-PD-1 antibodies).

Figures 15C, 15D:
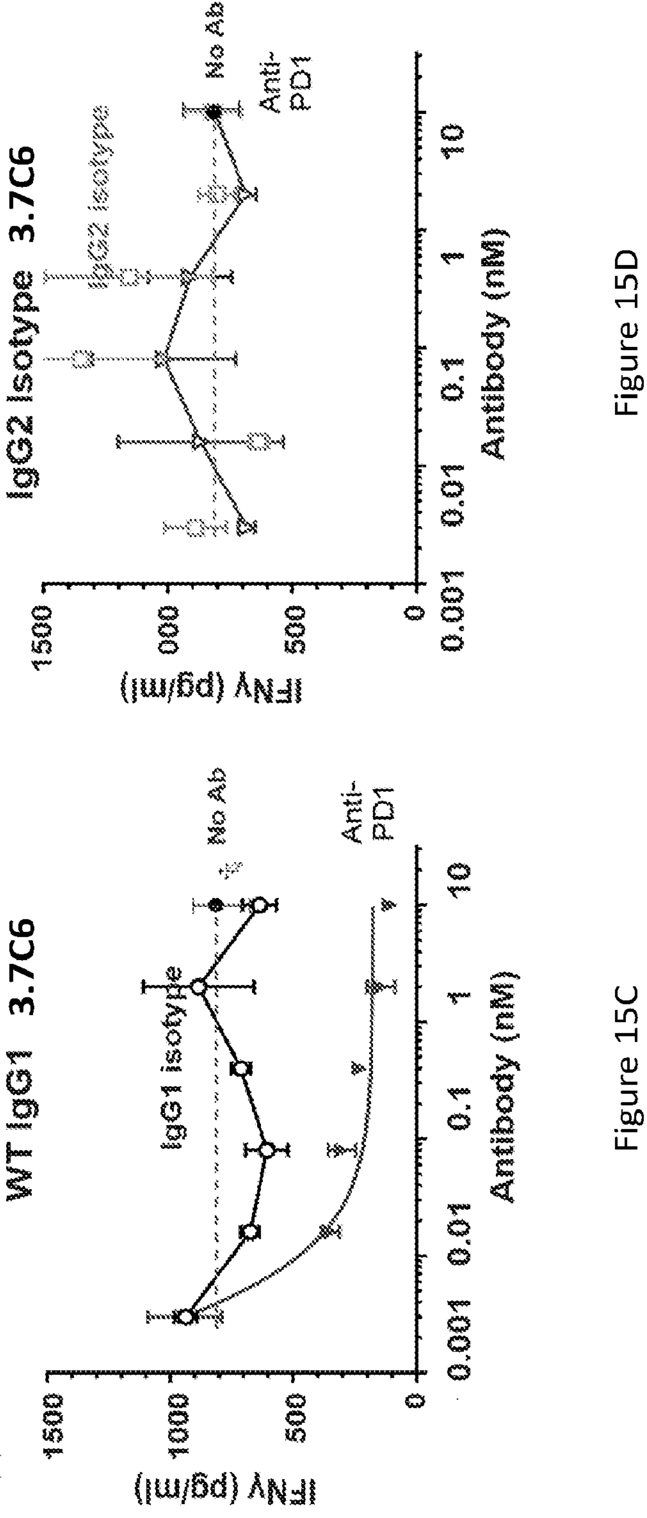
FIG. 15C is a graph depicting the effect of a WT IgG1 anti-PD-1 agonist antibody (closed triangular data points) on IFNγ in a whole human blood tetanus recall assay.
FIG. 15D is a graph depicting the effect of an IgG2 isotype anti-PD-1 antibody (open triangular data points) on IFNγ in a whole human blood tetanus recall assay.

The IgG1 3.7C6 anti-PD-1 antibody was compared to the same antibody prepared as a human IgG2 (FIGS. 15C and 15D). The anti-PD-1 IgG2 version of the antibody had identical activated T cell binding as anti-PD-1 IgG1, but did not show agonist activity. IgG2, IgG4, or IgG1(L234A, L235A) isotypes of the antibody also lacked agonist activity, which demonstrates a requirement for FcγR engagement/antibody clustering for functional agonist activity.

Example 6

This example demonstrates that the anti-PD-1 antibodies provided herein reduce an immune response in whole blood in a concentration-dependent manner.

Human whole blood, stimulated with an appropriate antigen in vitro, will elicit a specific T cell recall immune response when the donor has previously experienced exposure to the antigen of interest. The immune response can be gauged by IFN-γ and IL-17A levels.

Healthy human donors (N=6) were prescreened for in vitro recall responsiveness to the antigen tetanus toxoid, which the donors were likely previously exposed to during the course of common tetanus vaccinations. Whole blood from the donors was cultured for 96 hours in the presence of tetanus toxoid and either anti-PD-1 3.7C6 antibody (APE12890) or an irrelevant human IgG1 isotype control. After 96 hours of culture, supernatant was assayed for the presence of the cytokines IFN-γ and IL-17A using cytokine detection kits (Meso Scale Diagnostics, Rockville, MD). The results are provided in FIGS. 22A and 22B.

All donors responded to tetanus toxoid-specific stimulation by producing significant quantities of IFN-γ and IL-17A, although some donors responded more robustly than others. 3.7C6 antibody reduced secretion of both IFN-γ and IL-17A in a concentration-dependent manner, relative to the IgG1 isotype control antibody, as shown in FIGS. 22A and 22B. The median $IC_{50}$ and mean $IC_{50}$±SD of 3.7C6 in the human whole blood tetanus toxoid recall assay was determined to be 0.053 nM and 0.091±0.115 nM, respectively for IFN-γ inhibition, and 0.097 nM and 0.119±0.098 nM, respectively for IL-17A inhibition.

Example 7

This example demonstrates the binding kinetics (affinities) and thermal stability of the antibodies disclosed herein.

3.7C6 (APE12095.06 and APE12537.01) showed comparable binding kinetics by surface plasmon resonance (SPR) to human and cynomolgus monkey PD-1. The tight binding kinetics approached the limits for the instrument. The SPR data agree well with equilibrium binding affinities for APE12095 determined by kinetic exclusion assay (KinExA®). The final affinity measurements were: KinExA® $K_D$ for human PD-1: 75 pM; and KinExA® $K_D$ for cynomolgus PD-1: 450 pM.

437M5-112 (APE12043.05 and APE12538.01) also showed very comparable binding kinetics by SPR to human and cynomolgus monkey PD-1. The tight binding kinetics approached the limits for the instrument. The SPR data agree well with equilibrium binding affinities for APE12043 determined by KinExA®. The final affinity measurements were: KinExA® $K_D$ for human PD-1: 51 pM; and KinExA® $K_D$ for cynomolgus PD-1: 210 pM. A summary of $K_D$ measurements on the anti-PD-1 antibodies disclosed herein by Surface Plasmon Resonance and KinExA® are set forth in Table 9.

TABLE 9

| Antibody/ Lot | Human PD-1 $K_D$ (SPR) | Cynomolgus PD-1 $K_D$ (SPR) | Human PD-1 $K_D$ (KinExA) | Cynomolgus PD-1 $K_D$ (KinExA) |
|---|---|---|---|---|
| APE12043.05 | 31 pM | 90 pM | | |
| APE12538.01 | 51 pM | 217 pM | | |
| APE12043.04 | | | 51 pM | 210 pM |
| APE12095.06 | 51 pM | 244 pM | | |
| APE12537.01 | 43 pM | 445 pM | | |
| APE12095.04 | | | 75 pM | 450 pM |

The APE12537 antibody binding affinity and thermal stability was compared to that of a similar antibody designated "030-13263/030-13264." APE12537 differed from 030-13263/030-13264 by two mutations in the heavy chain: A52aI and D62Q by Kabat numbering (A53I and D63Q using the positions in the sequence listing). The results, provided in Table 10, show that these mutations increased binding affinity and thermal stability.

TABLE 10

| Antibody | Heavy Chain Variable Region (SEQ ID) | Light Chain Variable Region (SEQ ID) | $K_D$ Human PD-1 (nM) | $K_D$ Cynomolgus PD-1 (nM) | Fab Tm (° C.) |
|---|---|---|---|---|---|
| Mouse chimeric | — | — | 4.3 | n.d. | n.d. |
| 030-13263/ 030-13264 (CDR-grafted) | 43 | 49 | 0.186 | 1.02 ± 0.08 N = 2 | 61.2 ± 0.3 N = 3 |
| APE12537 (CDR-grafted and optimized) | 47 | 49 | 0.060 | 0.64 ± 0.10 N = 2 | 66.1 |

$K_D$ measurements for screening by Surface Plasmon Resonance (SPR) were performed on a Biacore T200 (GE Healthcare Life Sciences, Pittsburgh, PA), and kinetic constants were fit globally using a 1:1 binding model. Biotinylated human or cynomolgus monkey PD-1 extracellular domain monomer was captured at a 1 nM concentration on a Biacore Sensor chip SA (GE Healthcare Life Sciences, Pittsburgh, PA), with a carboxymethylated dextran surface pre-immobilized with streptavidin. The captured antigen level was targeted to yield a low response to prevent avidity effects on the dissociation rate. Tm measurements were determined by fluorescence-based thermal shift and differential scanning calorimetry.

Example 8

This example demonstrates that the anti-PD-1 antibodies disclosed herein show efficacy in vivo in a xenogeneic NSG/Hu-PBMC Graft vs. Host Disease (GvHD) model.

Figure 16A:
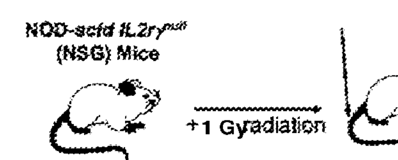
FIG. 16A is a schematic of the xenogeneic NSG/Hu-PBMC mouse model for the Graft vs. Host Disease study described in Example 8, in accordance with embodiments of the invention.
Figure 16B:
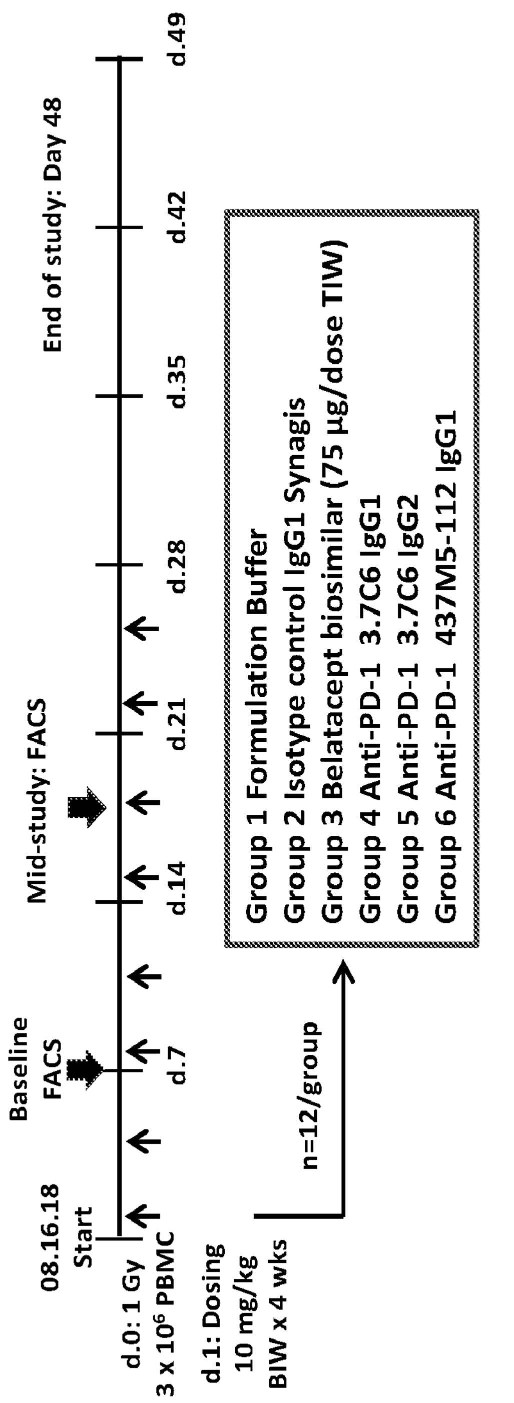
FIG. 16B is a schematic showing the timeline, dosing schedule, and model groups of the NSG/Hu-PBMC Graft vs. Host Disease study described in Example 8, in accordance with embodiments of the invention.

A xenogeneic NSG/Hu-PBMC GvHD model testing the efficacy of the anti-PD-1 antibodies disclosed herein was performed at The Jackson Laboratory JAX® In Vivo Pharmacology Services (Sacramento, CA). NOD-scid IL2r$\gamma^{null}$ (NSG) mice were irradiated with 1 Gy followed by intravenous injection of $3\times10^6$ human PBMCs in each mouse as illustrated in FIG. 16A. Antibodies were dosed intraperitoneally at 10 mg/kg twice weekly for 4 weeks starting the day following PBMC injection, and belatacept biosimilar was dosed intraperitoneally at 75 μg/mouse three times weekly for 4 weeks. Dosing regimens and dose groups in the study are shown in FIG. 16B. Disease was monitored three times weekly by body weight loss, death, and GvHD scores measuring: weight loss, activity, fur texture, paleness, and posture. Animals exhibiting more than 10% body weight loss were disease monitored daily, and animals exhibiting more than 20% body weight loss from starting weight were euthanized.

Figure 16C:
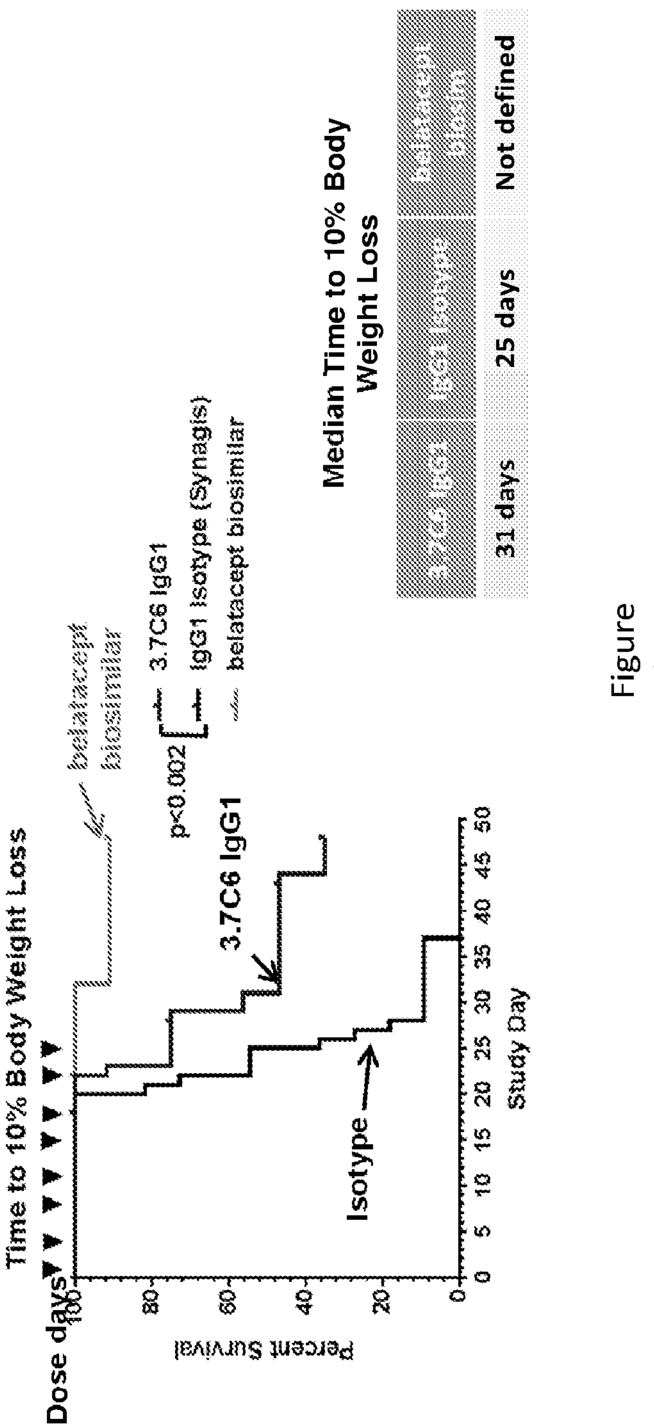
FIG. 16C is a graph depicting the results of the time to ≥10% body weight loss of the NSG/Hu-PBMC Graft vs. Host Disease study in Example 8 for an anti-PD-1 antibody.
Figure 16D:
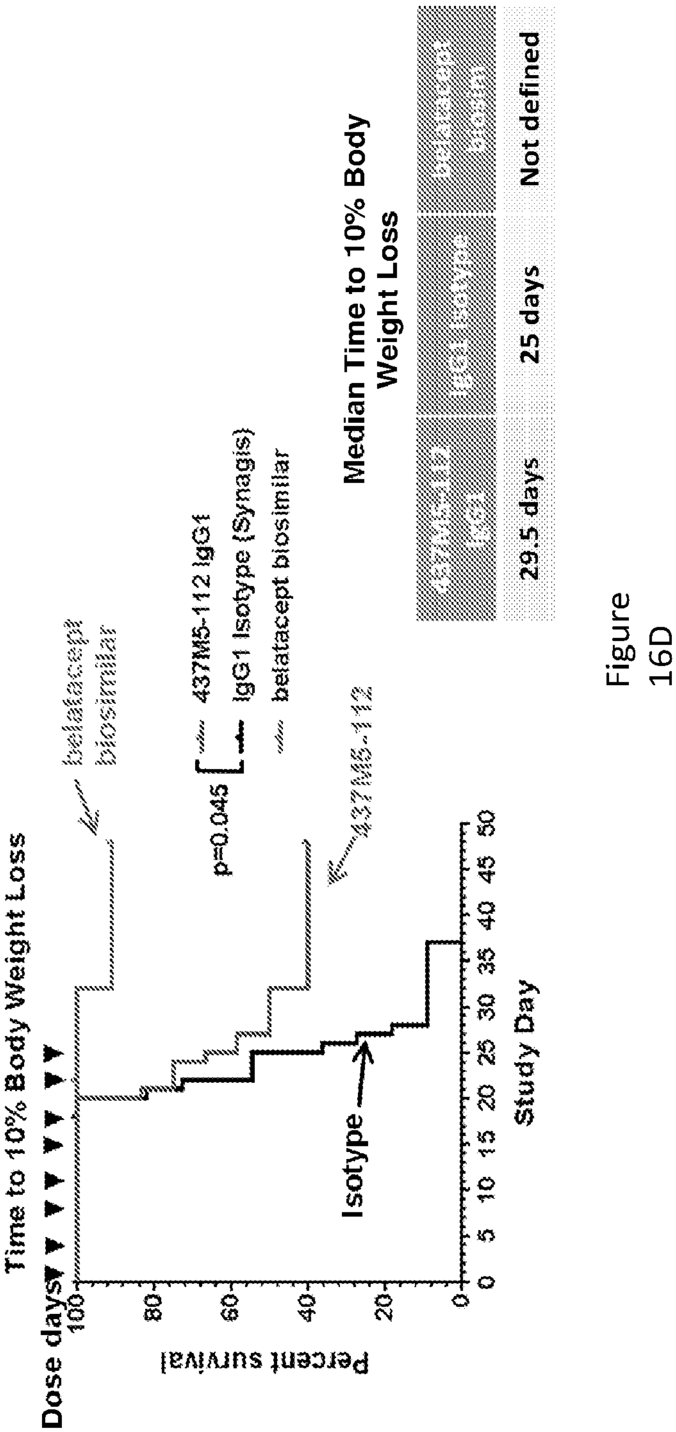
FIG. 16D is a graph depicting the results of the time to ≥10% body weight loss of the NSG/Hu-PBMC Graft vs. Host Disease study in Example 8 for an anti-PD-1 antibody.

The 3.7C6 PD-1 agonist antibody (APE12095) disclosed herein showed statistically significant efficacy vs. isotype control in time to 10% body weight loss (FIG. 16C). The 437M5-112 anti-PD-1 agonist antibody disclosed herein also showed statistically significant efficacy vs. isotype control in time to 10% body weight loss (FIG. 16D). Responses to both anti-PD-1 antibodies were bimodal with a proportion of the animals in each group fully surviving in the study (FIGS. 16C and 16D).

Example 9

This example demonstrates the study design of the cynomolgus monkey single dose Pharmacokinetics and Tolerability study.

The study design of the cynomolgus monkey single dose Pharmacokinetics and Tolerability study is set forth in Table 11. Assessments during the study were as follows:

Clinical Pathology, pre-dose (twice), Days 2, 6, 22, and 35 (Charles River Laboratories (CRL))

Blood FACS panels—major leukocyte populations and T cell subsets, pre-dose (twice), Days 2, 6, 22, and 35 (CRL)

B, T, NK, monocyte

CD4, CD8, T Central Memory, T Effector Memory, PD-1+, activated CD4+ and CD8+, Treg Receptor occupancy, Days 4, 14, 28, 35

PK sample analysis, anti-drug antibody analysis pre-dose & Day 35

Serum cytokine analyses (17-plex: IL-1, IL-1Ra, IL-2, IL-4, IL-5, IL-6, IL-8, IL-10, IL-12p40, IL-13, IL-17a, G-CSF, GM-CSF, IFNγ, MIP1β, MIP1α, TNF-α), pre-dose, 4 h and 24 h, Days 7 and 35

PK parameter analysis using Phoenix® WinNonlin® (Certara, USA).

Figure 17A:
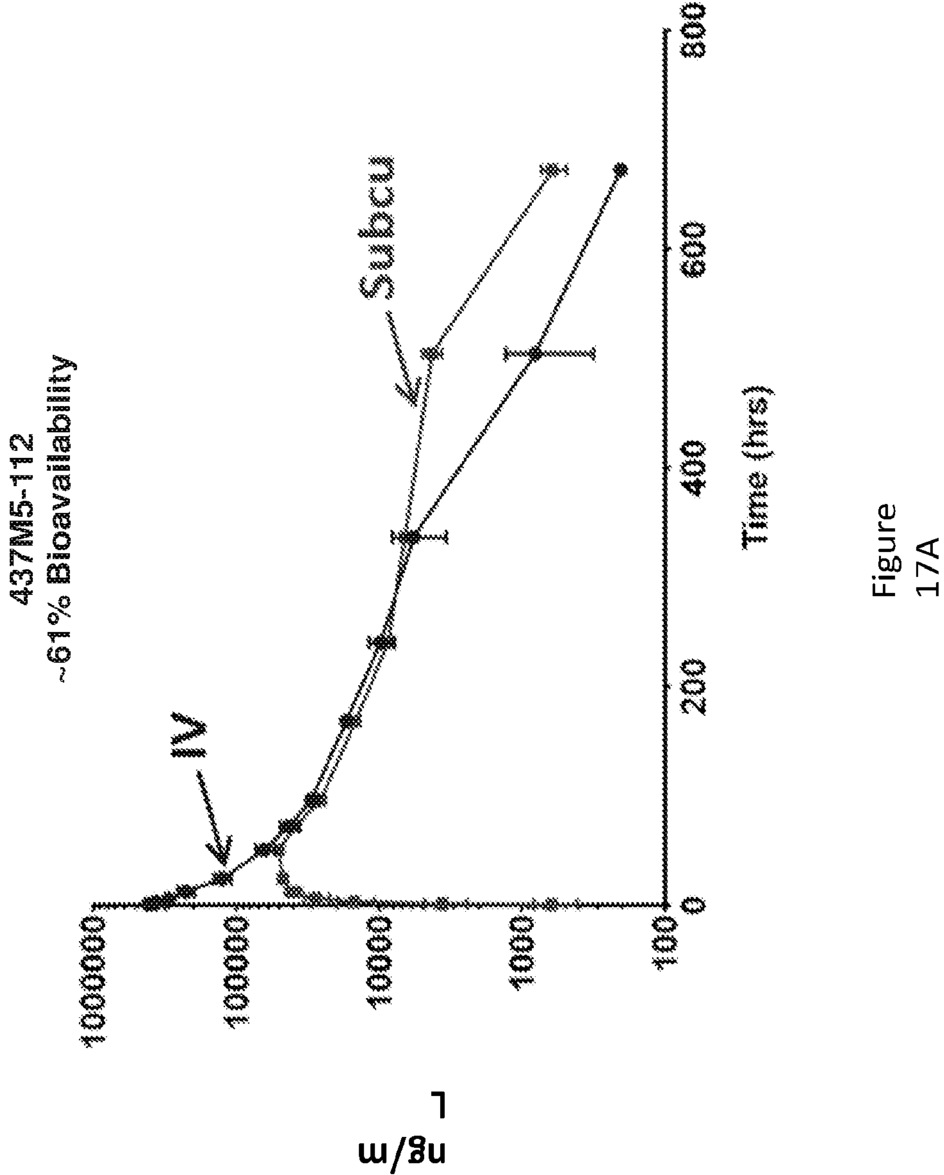
FIG. 17A is a graph depicting the pharmacokinetic properties in cynomolgus monkeys after a 10 mg/kg intravenous or subcutaneous single dose of an anti-PD-1 antibody.
Figure 17B:
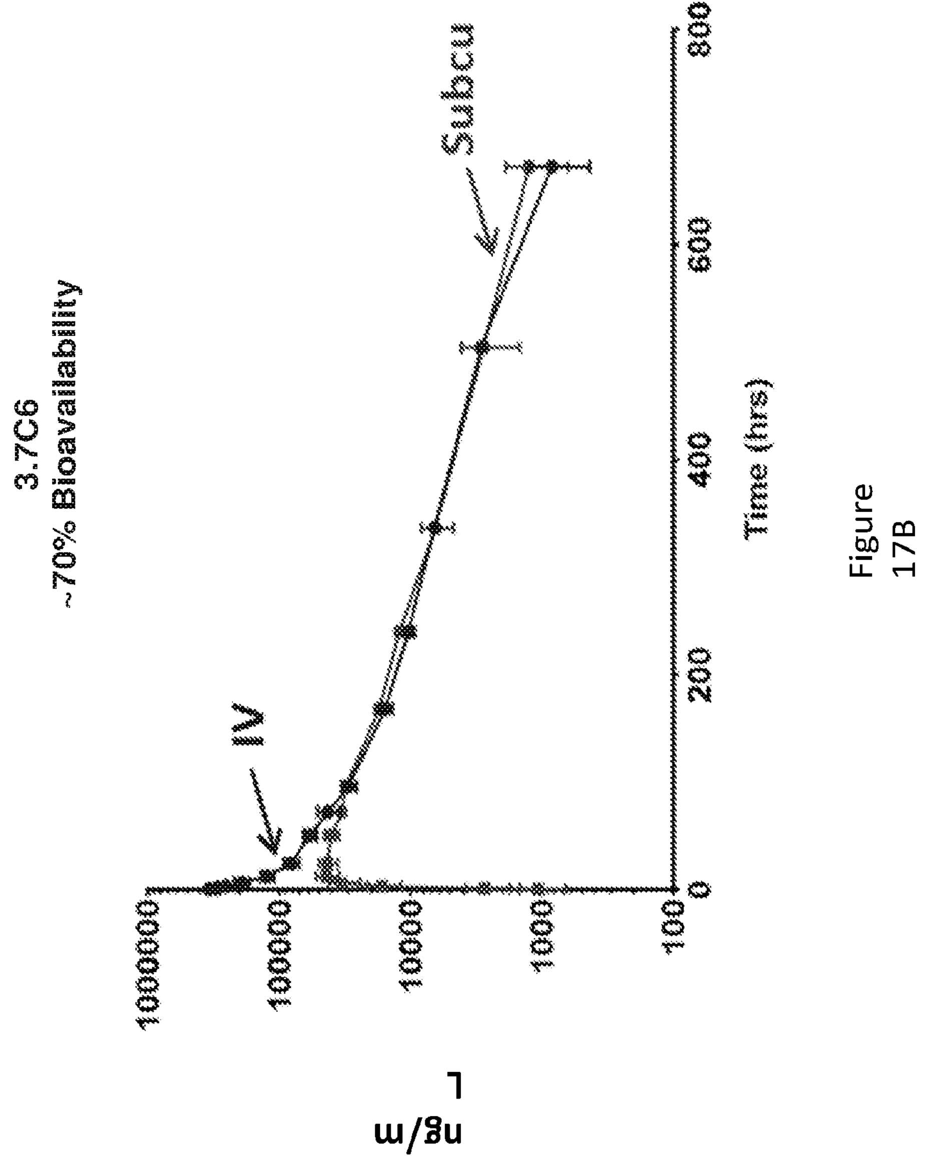
FIG. 17B is a graph depicting the pharmacokinetic properties in cynomolgus monkeys after a 10 mg/kg intravenous or subcutaneous single dose of an anti-PD-1 antibody.

Both PD-1 antibodies showed well-behaved pharmacokinetic properties with detectable drug levels in all animals at day 28 (FIGS. 17A and 17B). The study was completed on day 35. The doses were well-tolerated, with no adverse clinical signs or changes in clinical pathology observed. Results of the study are set forth in Tables 11 and 12.

TABLE 11

Study Design of the Cynomolgus Monkey Single Dose Pharmacokinetics and Tolerability Study.

| Group | Dose (mg/kg) | Number of male animals | Test article | Route of Administration |
|---|---|---|---|---|
| 1 | 10 | 3 | 437M5-112 stable CHO-S pool | Intravenous (IV) |
| 2 | 10 | 3 | 437M5-112 stable CHO-S pool | Subcutaneous (SC) |
| 3 | 10 | 3 | 3.7C6 stable CHO-S pool | Intravenous (IV) |
| 4 | 10 | 3 | 3.7C6 stable CHO-S pool | Subcutaneous (SC) |

TABLE 12

Analysis of Pharmacokinetic Parameters, Cytokine and Anti-Drug Antibody Responses.

| Parameter* | Units | IV (Group 1) | Sc (Group 2) | IV (Group 3) | Sc (Group 4) |
|---|---|---|---|---|---|
| Half-life | hr | 63.1 (11.6) | 91.3 (4.9) | 127.9 (7.4) | 115.2 (57.8) |
| Tmax† | hr | 0.67 (0.29) | 37.67 (22.2) | 0.50 (0) | 28.83 (19.70) |
| Cmax | ng/mL | 417,616 (62,049) | 51,210 (4.163) | 342,115 (31,785) | 46,365 (14,645) |
| C0 | ng/mL | 439,299 (15,116) | | 392234 (36,564) | |
| AUCall | hr* ng/mL | 13,422,916 (2,068,923) | 8,265,256 (353,998) | 12,199,665 (2,639,065) | 8,518,430 (1,899,319) |
| AUCINF_obs | hr* ng/mL | 13,473,226 (2,100,523) | 8,272,411 (357,502) | 12,263,340 (2,686,651) | 8,621,009 (1,985,163) |
| Cavg | ng/mL | 16,043 (2,499) | 9,840 (421) | 14,536 (3,128) | 10,1412 (2,260) |
| CLss or CL/F | mL/hr/kg | 0.753 (0.108) | 1.211 (0.052) | 0.842 (0.163) | 1.22 (0.31) |
| Vz or Vz/F | mL/kg | 69.8 (21.3) | 159.3 (5.7) | 154.3 (22.3) | 185.6 (65.6) |
| Vss_obs | mL/kg | 55.7 (18.9) | | 98.7 (15.4) | |
| F | % | | 61.4 | | 70.3 |

*Mean values (± SD), 3 animals/group.

†Tmax time to Cmax;

Cmax, maximum concentration;

C0, initial concentration;

AUCall, area under the curve to last observation;

AUCINF_obs, AUC to infinity based on last observation;

Cavg, average concentration;

CLss, clearance at steady state;

Vz, terminal phase volume of distribution;

Vss obs, steady-state volume of distribution based on last observation;

F, percent bioavailability.

TABLE 13

Analysis of Anti-Drug Antibody (ADA) Responses and Cytokines

| Animal | Antibody APE12538.01 Cohort | Pre-Dose ADA | Day 36 ADA | Day 36 ADA Titer |
|---|---|---|---|---|
| 1001 | 10 mg/kg IV | Negative | Positive | 320 |
| 1002 | 10 mg/kg IV | Negative | Positive | 80 |
| 1003 | 10 mg/kg IV | Negative | Positive | 320 |
| 2001 | 10 mg/kg SC | Negative | Positive | 20 |
| 2002 | 10 mg/kg SC | Negative | Positive | 320 |
| 2003 | 10 mg/kg SC | Negative | Positive | 20 |
| 3001 | 10 mg/kg IV | Negative | Negative | |
| 3002 | 10 mg/kg IV | Negative | Negative | |
| 3003 | 10 mg/kg IV | Negative | Positive | 64 |
| 4001 | 10 mg/kg SC | Negative | Negative | |
| 4002 | 10 mg/kg SC | Negative | Negative | |
| 4003 | 10 mg/kg SC | Negative | Positive | 128 |

Figure 18A:
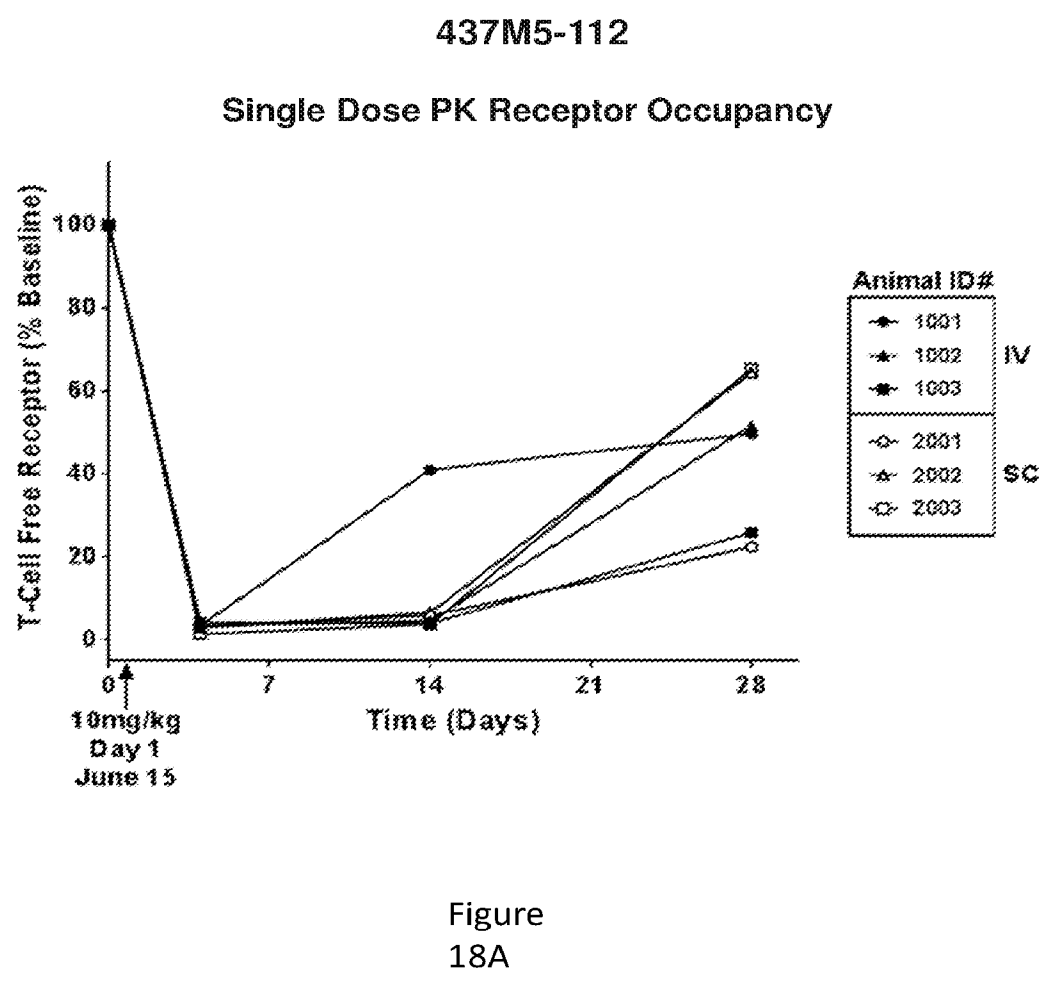

As shown, all 6 animals dosed with Antibody APE12538.01 had measureable/low titer anti-drug antibody at Day 36. Two of 6 animals dosed with Antibody APE12537.01 had measurable/low titer anti-drug antibody at Day 36. There were no meaningful changes in any cytokine evaluated. Further as shown in FIGS. 18A and 18B, sustained receptor occupancy through Day 14 was observed in all animals except #1001 (dosed IV with 437M5-112); some occupancy was found in most animals through Day 28.

Example 10

This example demonstrates that the anti-PD-1 antibody disclosed herein induced recruitment of the phosphatase SHP2 to the PD-1 cytoplasmic domain in PD-1 transfected Jurkat cells.

Figure 19A:
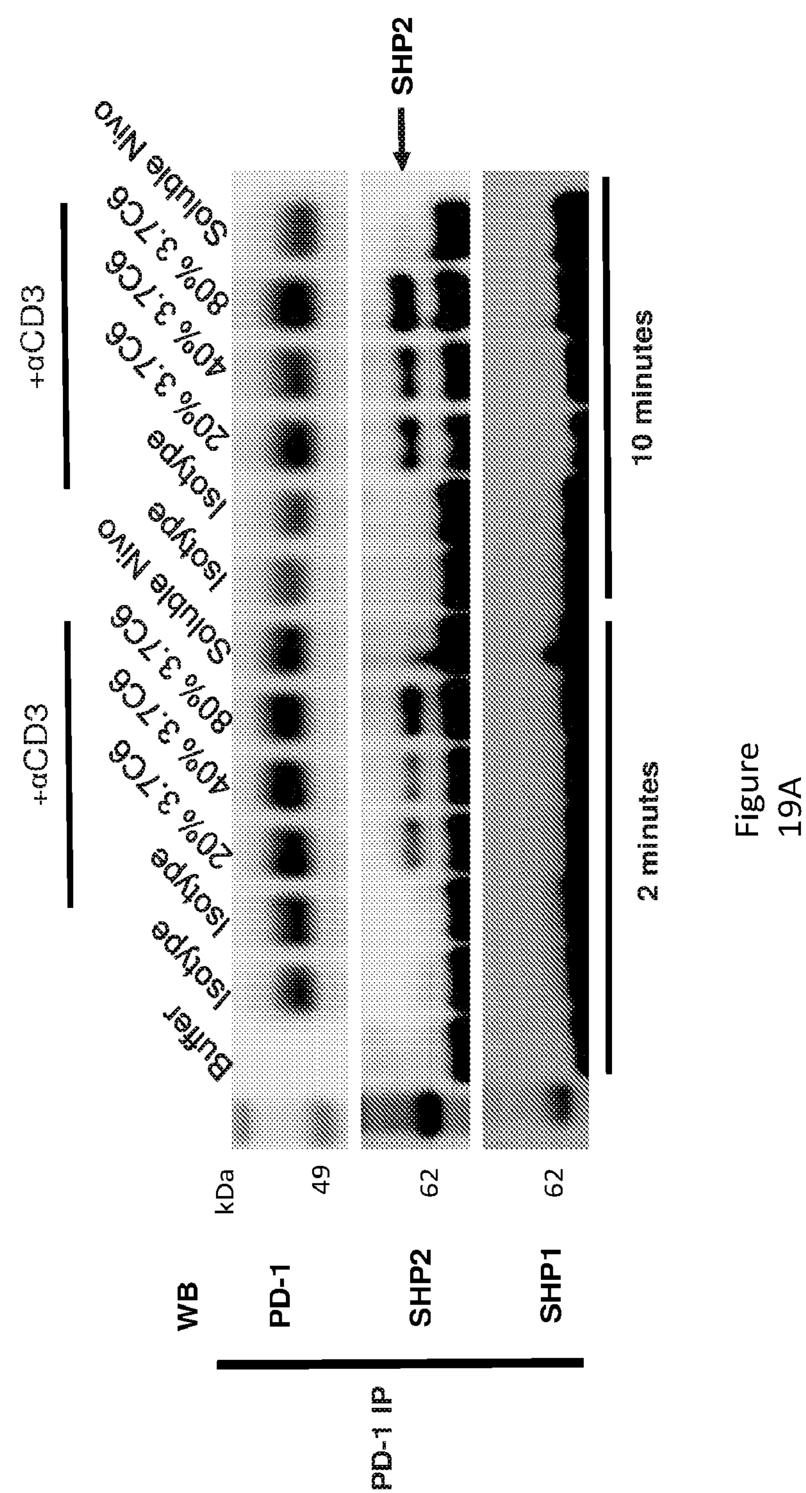
FIG. 19A is an SDS-PAGE gel showing the results of immunoblotting of PD-1 immunoprecipitates with either anti-PD-1 (top), anti-SHP2 (middle), or anti-SHP1 (bottom).
Figure 19B:
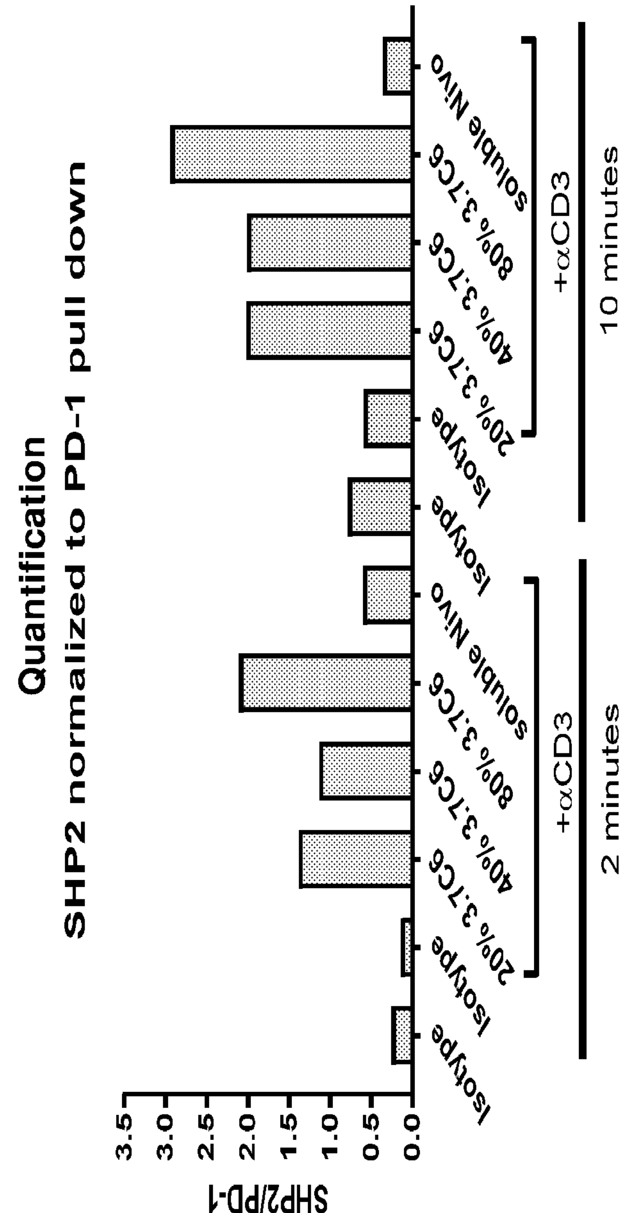
FIG. 19B is a graph depicting the densitometry quantification of the immunoblot shown in FIG. 19A.

Antibody 3.7C6 (APE12890) or a human IgG1 isotype control antibody recognizing hen egg lysozyme and a constant amount of anti-CD3 (UCHT1 clone; BioLegend, San Diego, CA) were coupled to magnetic beads (Dynabeads™ M-280 Tosylated; Invitrogen™/ThermoFisher Scientific). The anti-PD-1 antibody on beads mimics FcγR engagement by the antibody on antigen presenting cells. Stable human PD-1 transfected Jurkat cells were stimulated with the indicated beads for either 2 minutes or 10 minutes, cells lysed, and PD-1 immunoprecipitated by the addition of 3.7C6 coupled beads. Immunoprecipitates were analyzed by SDS-PAGE followed by immunoblotting with either anti-PD-1 (FIG. 19A, top), anti-SHP2 (FIG. 19A, middle), or anti-SHP1 (FIG. 19A, bottom). In this signaling assay, after PD-1 Jurkat cell activation with anti-CD3, the 3.7C6 antibody described herein, but not an isotype control antibody, induced recruitment of the phosphatase SHP2 but not SHP1 to the PD-1 cytoplasmic domain, as shown in FIGS. 19A (immunoblot) and 19B (densitometry quantification of the immunoblot). In the presence of anti-CD3 coated beads, the PD-1 antagonist antibody nivolumab (used at 100 nM in solution) did not induce either SHP2 or SHP1 recruitment to PD-1, as shown in FIGS. 19A-B. No SHP recruitment was found with soluble nivolumab. In combination with T-cell activation and CD28 co-stimulation, antibody 3.7C6 also reduced ZAP70 and LAT phosphorylation (data not shown). Antibody 3.7C6 had no effect on signaling pathways in the absence of T-cell activation.

Example 11

This example demonstrates that the epitope on human PD-1 that is bound by the 3.7C6 antibody disclosed herein is on the opposite face of PD-1 from the PD-L1 binding site.

Hydrogen-deuterium exchange mapping of the peptides on PD-1 bound by the 3.7C6 antibody (APE12537) disclosed herein was performed at Biomotif AB (Danderyd, Sweden) using recombinant human PD-1 monomer. The structure of PD-1 is publically available through the Protein Data Bank (PDB) operated by the National Center for Biotechnology Information (Bethesda, MD) at accession 4ZqK (see, also, Zak, K. M. et al., 2015, Structure 23:2341-2348; and PDB accession 5GGR (see, also, Lee, J. Y. et al., 2016, Nat Commun., 7:13354). One major peptide, labeled "HDX mapped β-hairpin", in FIGS. 20A and 20B, was protected from hydrogen-deuterium exchange by the 3.7C6 antibody. "HDX mapped β-hairpin" was comprised of amino acids 96-110 of PD-1, which amino acids have the sequence RVTQLPNGRDFHMSV. Another major peptide was comprised of amino acids 33-41 of PD-1, which amino acids have the sequence NPPTFSPAL. FIGS. 20A and 20B show a ribbon model of the crystal structure of human PD-1 extracellular domain (black) docked with a space-filling model of the crystal structure of human PD-L1 extracellular binding domain (light gray) (PD-1 and PD-L1 structures from the NCBI PDB). The molecules are oriented with the membrane-proximal region of PD-1 at the bottom left (FIG. 20A), and rotated by 900 showing the membrane-proximal region of PD-1 at the bottom center (FIG. 20B). Human PD-1 monomers containing different sets of mutations in defined surface regions were expressed, and the binding of the 3.7C6 antibody (APE12095) disclosed herein was evaluated by surface plasmon resonance. Mutations in the region labeled "PD-1 triple point mutant" in FIGS. 20A and 20B completely abolished binding of the 3.7C6 antibody disclosed herein. Mutations in the top of the loop labeled "HDX mapped β-hairpin" in FIGS. 20A and 20B did not affect binding of the 3.7C6 antibody disclosed herein. A combination of the hydrogen-deuterium exchange and PD-1 mutational mapping demonstrated that the 3.7C6 PD-1 agonist antibody disclosed herein showed binding to the region delineated in FIG. 20B by the dotted circle, which is on the opposite face of PD-1 from the PD-L1 binding site.

Example 12

This example demonstrates that the anti-PD-1 antibody disclosed herein inhibited production of IFNγ in peripheral blood mononuclear cells (PBMCs) from alopecia areata donors stimulated with keratinocyte peptide antigens.

Alopecia areata is hair loss mediated by the immune system. Hair loss results when immune privilege of the hair follicle is broken down by keratinocyte and melanocyte antigen-specific T cells producing IFNγ. T cells infiltrate hair follicle root sheaths. Activated T cells produce excessive IFNγ. Major histocompatibility complex class I and II molecules are abnormally expressed resulting in subsequent destruction of hair follicle cells and hair loss.

PBMCs were isolated from blood of alopecia areata donors and cultured ($2\times10^5$ cells/well) in plates in the presence of keratinocyte peptide antigens (peptide antigen pools were as described by Wang et al., *J Invest Dermatol.* 2016 August; 136(8):1617-1626), and the indicated concentrations of tetramer PD-L1-IgG1 Fc, IgG1 3.7C6 anti-PD-1 antibody (APE12890), or control IgG1 isotype tetramer, or control IgG1 isotype. After five days, the cells were washed and incubated for an additional 20 hours in an ELISpot plate to detect the number of IFNγ secreting cells. The results from each donor and treatment group were normalized to the untreated wells to allow statistical comparison of the data from 12 donors for treatment and negative controls.

As shown in FIG. 21A, the IgG1 3.7C6 anti-PD-1 antibody as compared to the control IgG1 isotype inhibited IFNγ production in a concentration-dependent manner. As shown in FIG. 21B, the positive control PD-L1-IgG1 Fc tetramer as compared to the IgG1 isotype tetramer inhibited IFNγ production compared to control IgG1 isotype tetramer in a concentration-dependent manner. Both the anti-PD-1 antibody described herein and PD-L1-IgG1 Fc tetramer significantly inhibited the number of IFNγ secreting cells at concentrations at or above 1 nM ($p<0.001$), as shown in FIGS. 21C and 21D.

Example 13

This example demonstrates that the anti-PD-1 antibody disclosed herein inhibited production of IFNγ in peripheral blood mononuclear cells (PBMCs) from alopecia areata donors stimulated with melanocyte peptide antigens.

Alopecia areata is hair loss mediated by the immune system. Hair loss and/or loss of hair pigmentation results when immune privilege of the hair follicle is broken down by keratinocyte and melanocyte antigen-specific T cells producing IFNγ. T cells infiltrate hair follicle root sheaths. Activated T cells produce excessive IFNγ. Major histocompatibility complex class I and II molecules are abnormally expressed resulting in subsequent destruction of hair follicle cells and hair loss. A similar melanocyte-specific T cell response in the skin, results in the destruction of melanocytes in vitiligo.

PBMCs were isolated from blood of alopecia areata donors and cultured (2×105 cells/well) in plates in the presence of melanocyte peptide antigens (peptide antigen pools were as described by Wang et al., J Invest Dermatol. 2016 August 136(8):1617-1626), and the indicated concentrations of tetramer PD-L1-IgG1 Fc, IgG1 3.7C6 anti-PD-1 antibody (APE12890), or control IgG1 isotype tetramer, or control IgG1 isotype. After five days, secreted IFNγ in culture supernatants was quantified by Meso Scale Discovery (Meso Scale Diagnostics, Rockville, MD). The results from each donor and treatment were normalized to the untreated wells to allow statistical comparison of the data from 12 donors for treatment and negative controls. Additionally, after 5 days, the cells were washed and incubated for an additional 20 hours in an ELISpot assay to detect the number of IFNγ secreting cells. The results from each donor and treatment were normalized to the untreated wells to allow statistical comparison of the data from 12 donors for treatment and negative controls. The results are presented in FIGS. 23A-23D.

As shown in FIG. 23A, the IgG1 3.7C6 anti-PD-1 antibody as compared to the control IgG1 isotype inhibited IFNγ production in a concentration-dependent manner. As shown in FIG. 23B the positive control PD-L1-IgG1 Fc tetramer as compared to the IgG1 isotype tetramer inhibited IFNγ production compared to control IgG1 isotype tetramer in a concentration-dependent manner. Both the anti-PD-1 antibody described herein and PD-L1-IgG1 Fc tetramer significantly inhibited IFNγ production at concentrations at or above 100 nM ($p<0.001$). Both the anti-PD-1 antibody described herein and PD-L1-IgG1 Fc tetramer significantly reduced the number of IFNγ secreting cells at concentrations at or above 10 nM ($p<0.001$) as shown in FIGS. 23C and 23D.

Example 14

This example demonstrates that the anti-PD-1 antibody disclosed herein show efficacy in vivo in a xenogeneic NSG/Hu-PBMC Graft v. Host Disease (GvHD) model at a dosage of 3 mg/kg.

A xenogeneic NSG/Hu-PBMC GvHD model testing the efficacy of the anti-PD01 antibody disclosed herein was performed at The Jackson Laboratory, Sacramento, CA). NOD-scid IL2rγ$^{null}$ (NSG) mice were irradiated with 1 Gy followed by intravenous injection of $0.9\times10^7$ human PBMCs in each mouse as illustrated in FIG. 24A. Antibodies were dosed intraperitoneally at 30 mg/kg, 10 mg/kg, or 3 mg/kg twice weekly for 4 weeks starting the day following PBMC injection. A fourth group was dosed with an irrelevant isotype control antibody at 30 mg/kg twice weekly and a fifth group was dosed with CTLA-4-IgG, a known positive control for efficacy in the model, at 75 μg/mouse, three times a week. Dosing regimens and dose groups in the study are shown in FIG. 24B. Disease was monitored three times weekly for by weight loss, death, and GvHD scores measuring: weight loss, activity, fur texture, paleness, and posture. Animals exhibiting more than 10% body weight loss were disease monitored daily, and animals exhibiting more than 20% body weight loss from starting weight were euthanized.

The 3.7C6 PD-1 agonist antibody (APE12890) disclosed herein showed statistically significant efficacy vs. isotype control in survival, increasing median survival time (FIG. 24C). Individual animals' percent of starting body weight over the course of the study are shown in FIGS. 24D, 24E, 24F, 24G, and 24H when dosed with isotype control IgG1 at 30 mg/kg, Anti-PD-1 agonist IgG1 (3.7C6) at 30 mg/kg, Anti-PD-1 agonist IgG1 (3.7C6) at 10 mg/kg, Anti-PD-1 agonist IgG1 (3.7C6) at 3 mg/kg, and CTLA-4-Ig (positive control) at 75 μg/dose, respectively.

There was not a significant difference in survival between the anti-PD-1 agonist IgG1 (3.7C6) 30 mg/kg and anti-PD-1 agonist IgG1 (3.7C6) 3 mg/kg dose groups. This suggests that efficacy in the GvHD model may be obtained at doses less than 3 mg/kg.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A PD-1 binding agent comprising an immunoglobulin heavy chain variable region and an immunoglobulin light chain variable region, wherein the immunoglobulin heavy chain variable region comprises at least the CDR regions of any one of SEQ ID NOs: 43-47 or 61-63, and the immunoglobulin light chain variable region comprises at least the CDR regions of any one of SEQ ID NOs: 48-50.

2. The PD-1 binding agent of claim 1, wherein the PD-1 binding agent comprises the following CDR regions when determined according to Kabat:

CDRH1: SEQ ID NO: 64
CDRH2: SEQ ID NO: 65
CDRH3: SEQ ID NO: 66
CDRL1: SEQ ID NO: 67
CDRL2: SEQ ID NO: 68
CDRL3: SEQ ID NO: 69;

or wherein the PD-1 binding agent comprises the following CDR regions when determined according to IMGT:

CDRH1: SEQ ID NO: 70
CDRH2: SEQ ID NO: 71
CDRH3: SEQ ID NO: 72
CDRL1: SEQ ID NO: 73
CDRL2: SEQ ID NO: 74
CDRL3: SEQ ID NO: 75.

3. The PD-1 binding agent of claim 1, wherein the immunoglobulin heavy chain variable region comprises at least 80% sequence identity to any one of SEQ ID NOs: 43-47 or 61-63, and the immunoglobulin light chain variable region comprises at least 80% sequence identity to SEQ ID NOs: 48-50.

4. The PD-1 binding agent of claim 1, wherein the immunoglobulin heavy chain variable region comprises any one of SEQ ID NOs: 43-47 or 61-63, and the immunoglobulin light chain variable region comprises any one of SEQ ID NOs: 48-50.

5. The PD-1 binding agent of claim 1, wherein the immunoglobulin heavy chain variable region comprises SEQ ID NO: 47, and the immunoglobulin light chain variable region comprises SEQ ID NO: 49.

6. The PD-1 binding agent of claim 1, wherein the immunoglobulin heavy chain variable region comprises SEQ ID NO: 46, and the immunoglobulin light chain variable region comprises SEQ ID NO: 50.

7. The PD-1 binding agent of claim 1, wherein the immunoglobulin heavy chain comprises SEQ ID NO: 51, and the immunoglobulin light chain comprises SEQ ID NO: 52.

8. The PD-1 binding agent of claim 1, wherein the PD-1 binding agent is an antibody, an antibody conjugate, or an antigen-binding fragment thereof.

9. The PD-1 binding agent of claim 1, wherein the PD-1 binding agent is a $F(ab')_2$, Fab', Fab, Fv, scFv, dsFv, or a single chain binding polypeptide.

10. The anti-PD-1 binding agent of claim 1, wherein the PD-1 binding agent comprises an IgG Fc region that binds an Fc receptor on an antigen presenting cell.

11. The PD-1 binding agent of claim 1, wherein the PD-1 binding agent comprises an Fc region of IgG1 or other Fc region that binds an FcγR.

12. The PD-1 binding agent of claim 1, wherein the PD-1 binding agent is an IgG1 antibody.

13. The anti-PD-1 binding agent of claim 2, wherein the PD-1 binding agent comprises an IgG Fc region that binds an Fc receptor on an antigen presenting cell.

14. The PD-1 binding agent of claim 2, wherein the PD-1 binding agent comprises an Fc region of IgG1 or other Fc region that binds an FcγR.

15. The PD-1 binding agent of claim 2, wherein the PD-1 binding agent is an IgG1 antibody.

16. The anti-PD-1 binding agent of claim 5, wherein the PD-1 binding agent comprises an IgG Fc region that binds an Fc receptor on an antigen presenting cell.

17. The PD-1 binding agent of claim 5, wherein the PD-1 binding agent comprises an Fc region of IgG1 or other Fc region that binds an FcγR.

18. A nucleic acid encoding the immunoglobulin heavy chain and/or immunoglobulin light chain of the anti-PD-1 binding agent of claim 1.

19. A nucleic acid encoding the immunoglobulin heavy chain and/or immunoglobulin light chain of the anti-PD-1 binding agent of claim 5.

20. A cell that expresses the anti-PD-1 binding agent of claim 5.

21. A method of preparing the anti-PD-1 binding agent of claim 5, the method comprising expressing a nucleic acid encoding the immunoglobulin heavy chain and a nucleic acid encoding the immunoglobulin light chain in a cell, wherein the immunoglobulin heavy and light chains can be expressed from a single nucleic acid or the immunoglobulin heavy and light chains can be expressed from separate nucleic acids.

22. A pharmaceutical composition comprising (a) anti-PD-1 binding agent of claim 14, and (b) a pharmaceutically acceptable carrier.

23. A pharmaceutical composition comprising (a) anti-PD-1 binding agent of claim 17, and (b) a pharmaceutically acceptable carrier.

24. A pharmaceutical composition comprising (a) anti-PD-1 binding agent of claim 11, and (b) a pharmaceutically acceptable carrier.

* * * * *